United States Patent
Rosen et al.

(10) Patent No.: US 9,481,910 B2
(45) Date of Patent: Nov. 1, 2016

(54) METHODS AND COMPOSITIONS FOR THE DETECTION OF DRUG RESISTANT BRAF ISOFORMS

(75) Inventors: Neal Rosen, Englewood, NJ (US); Poulikos Poulikakos, New York, NY (US); David Solit, New York, NY (US)

(73) Assignee: MEMORIAL SLOAN-KETTERING CANCER CENTER, NY, NY (US)

( * ) Notice: Subject to any disclaimer, the term of this patent is extended or adjusted under 35 U.S.C. 154(b) by 560 days.

(21) Appl. No.: 13/480,050

(22) Filed: May 24, 2012

(65) Prior Publication Data
US 2012/0301878 A1 Nov. 29, 2012

Related U.S. Application Data

(60) Provisional application No. 61/519,593, filed on May 25, 2011.

(51) Int. Cl.
*C12Q 1/68* (2006.01)

(52) U.S. Cl.
CPC ....... *C12Q 1/6886* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 7,625,699 B2 | 12/2009 | Devlin et al. |
| 2013/0217721 A1* | 8/2013 | Lo et al. ................. 514/300 |

OTHER PUBLICATIONS

Seth et al. (Gut, 2009:58, p. 1234-1241, Abstract only).*
Smith et al. (Human Pathology, 2011, 42:500-506).*
Nazarian et al. (Nature, 2010, vol. 468:973-978).*
Flaherty, Keith T., et al , "Inhibition of Mutated, Activated BRAF in Metastatic Melanoma", *The New England Journal of Medicine*, vol. 363(9), pp. 809-819 (2010).

* cited by examiner

*Primary Examiner* — Stephanie K Mummert
(74) *Attorney, Agent, or Firm* — Heslin Rothenberg Farley and Mesiti, PC; Kathy Smith Dias, Esq.

(57) ABSTRACT

The present invention provides methods and compositions for the detection of novel BRAF splice variants that mediate resistance to BRAF and/or pan-RAF inhibitors. In particular, the invention provides PCR primer(s) to be used in the disclosed methods of detection. In some embodiments, the compositions and methods of the present invention are used to predict resistance to BRAF and/or pan-RAF inhibitors in a subject suffering from or suspected of having cancer and further provides alternative treatment strategy(ies) for a subject predicted to be resistant to BRAF and/or pan-RAF inhibitors. In a further embodiment, methods and composition for the identification of novel agents useful to overcome resistance to BRAF and/or pan-RAF inhibitors are disclosed. The present invention also provides isolated polynucleotide sequences of novel 5' BRAF splice variant(s) and proteins produced from such polynucleotide sequences as well as cell line(s) that endogenously or exogenously express the splice variant(s).

7 Claims, 30 Drawing Sheets

SEQUENCE LISTING

<160> NUMBER OF SEQ ID NOS: 21

<210> SEQ ID NO 1
<211> LENGTH: 2949
<212> TYPE: DNA
<213> ORGANISM: Homo sapiens

<400> SEQUENCE: 1

```
cgcctccctt cccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg cgccggcgcc gcggcctctt cggctgcgga     180
ccctgccatt ccggaggagg tgtggaatat caaacaaatg attaagttga cacaggaaca     240
tatagaggcc ctattggaca aatttggtgg ggagcataat ccaccatcaa tatatctgga     300
ggcctatgaa gaatacacca gcaagctaga tgcactccaa caaagagaac aacagttatt     360
ggaatctctg gggaacggaa ctgatttttc tgtttctagc tctgcatcaa tggataccgt     420
tacatcttct tcctcttcta gcctttcagt gctaccttca tctctttcag tttttcaaaa     480
tcccacagat gtggcacgga gcaaccccaa gtcaccacaa aaacctatcg ttagagtctt     540
cctgcccaac aaacagagga cagtggtacc tgcaaggtgt ggagttacag tccgagacag     600
tctaaagaaa gcactgatga tgagaggtct aatcccagag tgctgtgctg tttacagaat     660
tcaggatgga gagaagaaac caattggttg ggacactgat atttcctggc ttactggaga     720
agaattgcat gtgaagtgt tggagaatgt tccacttaca acacacaact ttgtacgaaa     780
aacgttttc accttagcat tttgtgactt ttgtcgaaag ctgcttttcc agggtttccg     840
ctgtcaaaca tgtggttata aatttcacca gcgttgtagt acagaagttc cactgatgtg     900
tgttaattat gaccaacttg atttgctgtt tgtctccaag ttctttgaac accacccaat     960
accacaggaa gaggcgtcct tagcagagac tgccctaaca tctggatcat cccttccgc    1020
accgcctcg gactctattg ggccccaaat tctcaccagt ccgtctcctt caaaatccat    1080
tccaattcca cagcccttcc gaccagcaga tgaagatcat cgaaatcaat ttgggcaacg    1140
agaccgatcc tcatcagctc ccaatgtgca tataaacaca atagaacctg tcaatattga    1200
tgacttgatt agagaccaag gatttcgtgg tgatggagga tcaaccacag gtttgtctgc    1260
tacccccct gcctcattac ctggctcact aactaacgtg aaagccttac agaaatctcc    1320
aggacctcag cgagaaagga gtcatcttc atcctcagaa gacaggaatc gaatgaaaac    1380
acttggtaga cgggactcga gtgatgattg ggagattcct gatgggcaga ttacagtggg    1440
acaaagaatt ggatctggat catttggaac agtctacaag ggaaagtggc atggtgatgt    1500
ggcagtgaaa atgttgaatg tgacagcacc tacacctcag cagttacaag ccttcaaaaa    1560
tgaagtagga gtactcagga aaacacgaca tgtgaatatc ctactcttca tgggctattc    1620
cacaaagcca caactggcta ttgttaccca gtggtgtgag ggctccagct tgtatcacca    1680
tctccatatc attgagacca aatttgagat gatcaaactt atagatattg cacgacagac    1740
tgcacagggc atggattact acacagccaa gtcaatcatc cacagagacc tcaagagtaa    1800
taatatattt cttcatgaag acctcacagt aaaaataggt gattttggtc tagctacagt    1860
```

```
gaaatctcga tggagtgggt cccatcagtt tgaacagttg tctggatcca ttttgtggat    1920
ggcaccagaa gtcatcagaa tgcaagataa aaatccatac agctttcagt cagatgtata    1980
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa agccatgaa gagattaatg gcagagtgcc tcaaaagaa     2160 aagagatgag agaccactct ttccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa cacttgtgtg gttaaagact agatataatt ttttccccaaa   2520 ctaaaattta tacttaacat tggattttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataattt tctataacta tttcttttta    2880
taacaatttg gaaatgtgg atgtctttta tttccttgaa gcaataaact aagtttcttt    2940
ttataaaaa                                                            2949

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
ggctctcggt tataagatgg c                                              21

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
acaggaaacg caccatatcc                                                20

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
ctgccattcc ggaggaggac t                                              21

<210> SEQ ID NO 5
<211> LENGTH: 23
<212> TYPE: DNA
<213> ORGANISM: Artificial Sequence
```

```
<220> FEATURE:
<223> OTHER INFORMATION: Synthetic oligonucleotide

<400> SEQUENCE: 5
ttagttagtg agccaggtaa tga                                              23

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
acaaacagag gacagtggac                                                  20

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
caaacagagg acagtgaaa                                                   19

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
acaggaaacg caccatatcc                                                  20

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
cccggctctc ggttataag                                                   19

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
tcaatcatcc acagagacct c                                                21

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 11
ggatccagac aactgttcaa ac                                               22
```

<210> SEQ ID NO 12
<211> LENGTH: 766
<212> TYPE: PRT
<213> ORGANISM: Homo sapiens

<400> SEQUENCE: 12

Met Ala Ala Leu Ser Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
370                 375                 380

```
Asp Gln Gly Phe Arg Gly Asp Gly Gly Ser Thr Gly Leu Ser Ala
385                 390                 395                 400

Thr Pro Pro Ala Ser Leu Pro Gly Ser Leu Thr Asn Val Lys Ala Leu
        405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
            485                 490                 495

Ala Phe Lys Asn Glu Val Gly Val Leu Arg Lys Thr Arg His Val Asn
        500                 505                 510

Ile Leu Leu Phe Met Gly Tyr Ser Thr Lys Pro Gln Leu Ala Ile Val
    515                 520                 525

Thr Gln Trp Cys Glu Gly Ser Ser Leu Tyr His His Leu His Ile Ile
530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
            565                 570                 575

Leu Lys Ser Asn Asn Ile Phe Leu His Glu Asp Leu Thr Val Lys Ile
        580                 585                 590

Gly Asp Phe Gly Leu Ala Thr Glu Lys Ser Arg Trp Ser Gly Ser His
    595                 600                 605

Gln Phe Glu Gln Leu Ser Gly Ser Ile Leu Trp Met Ala Pro Glu Val
610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
            645                 650                 655

Ser Asn Ile Asn Asn Arg Asp Gln Ile Ile Phe Met Val Gly Arg Gly
        660                 665                 670

Tyr Leu Ser Pro Asp Leu Ser Lys Val Arg Ser Asn Cys Pro Lys Ala
    675                 680                 685

Met Lys Arg Leu Met Ala Glu Cys Leu Lys Lys Lys Arg Asp Glu Arg
690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
            725                 730                 735

Gly Phe Gln Thr Glu Asp Phe Ser Leu Tyr Ala Cys Ala Ser Pro Lys
        740                 745                 750

Thr Pro Ile Gln Ala Gly Gly Tyr Gly Ala Phe Pro Val His
    755                 760                 765

<210> SEQ ID NO 13
<211> LENGTH: 2109
<212> TYPE: DNA
<213> ORGANISM: Homo sapiens
```

<400> SEQUENCE: 13

```
cgcctccctt ccccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg cgccggcgcc gcggcctctt cggctgcgga     180
ccctgccatt ccggaggagg tgtggaatat caaacaaatg attaagttga cacaggaaca     240
tatagaggcc ctattggaca aatttggtgg ggagcataat ccaccatcaa tatatctgga     300
ggcctatgaa gaatacacca gcaagctaga tgcactccaa caaagagaac aacagttatt     360
ggaatctctg gggaacggaa ctgattttc tgtttctagc tctgcatcaa tggataccgt     420
tacatcttct tcctcttcta gcctttcagt gctaccttca tctctttcag ttttcaaaa     480
tcccacagat gtggcacgga gcaaccccaa gtcaccacaa aaacctatcg ttagagtctt     540
cctgcccaac aaacagagga cagtgaaaac acttggtaga cgggactcga gtgatgattg     600
ggagattcct gatgggcaga ttacagtggg acaaagaatt ggatctggat catttggaac     660
agtctacaag ggaaagtggc atggtgatgt ggcagtgaaa atgttgaatg tgacagcacc     720
tacacctcag cagttacaag ccttcaaaaa tgaagtagga gtactcagga aaacacgaca     780
tgtgaatatc ctactcttca tgggctattc cacaaagcca caactggcta ttgttaccca     840
gtggtgtgag ggctccagct tgtatcacca tctccatatc attgagacca aatttgagat     900
gatcaaactt atagatattg cacgacagac tgcacagggc atggattact acacgccaa     960
gtcaatcatc cacagagacc tcaagagaaa taatatatttt cttcatgaag acctcacagt    1020
aaaaataggt gattttggtc tagctacagt gaaatctcga tggagtgggt cccatcagtt    1080
tgaacagttg tctggatcca ttttgtggat ggcaccagaa gtcatcagaa tgcaagataa    1140
aaatccatac agctttcagt cagatgtata tgcatttgga attgttctgt atgaattgat    1200
gactggacag ttaccttatt caaacatcaa caacagggac cagataattt ttatggtggg    1260
acgaggatac ctgtctccag atctcagtaa ggtacggagt aactgtccaa aagccatgaa    1320
gagattaatg gcagagtgcc tcaaaaagaa aagagatgag agaccactct ttccccaaat    1380
tctcgcctct attgagctgc tggcccgctc attgccaaaa attcaccgca gtgcatcaga    1440
accctccttg aatcgggctg gtttccaaac agaggatttt agtctatatg cttgtgcttc    1500
tccaaaaaca cccatccagg caggggata tggtgcgttt cctgtccact gaaacaaatg    1560
agtgagagag ttcaggagag tagcaacaaa aggaaaataa atgaacatat gtttgcttat    1620
atgttaaatt gaataaaata ctctcttttt ttttaaggtg aaccaaagaa cacttgtgtg    1680
gttaaagact agatataatt tttccccaaa ctaaaattta tacttaacat tggattttta    1740
acatccaagg gttaaaatac atagacattg ctaaaaattg gcagagcctc ttctagaggc    1800
tttactttct gttccgggtt tgtatcattc acttggttat tttaagtagt aaacttcagt    1860
ttctcatgca acttttgttg ccagctatca ctacctatgc ctgtgtttgc aggtgagaag    1920
ttggcagtcg gttagcctgg gttagataag gcaaactgaa cagatctaat ttaggaagtc    1980
agtagaattt aataattcta ttattattct taataatttt tctataacta tttctttta    2040
taacaatttg gaaaatgtgg atgtctttta tttccttgaa gcaataaact aagtttcttt    2100
ttataaaaa                                                            2109
```

<210> SEQ ID NO 14
<211> LENGTH: 1947
<212> TYPE: DNA
<213> ORGANISM: Homo sapiens

<400> SEQUENCE: 14

```
cgcctccctt ccccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg cgccggcgcc gcggcctctt cggctgcgga     180
ccctgccatt ccggaggagg acttgattag agaccaagga tttcgtggtg atggaggatc     240
aaccacaggt ttgtctgcta ccccccctgc ctcattacct ggctcactaa ctaacgtgaa     300
agccttacag aaatctccag gacctcagcg agaaaggaag tcatcttcat cctcagaaga     360
caggaatcga atgaaaacac ttggtagacg ggactcgagt gatgattggg agattcctga     420
tgggcagatt acagtgggac aaagaattgg atctggatca tttggaacag tctacaaggg     480
aaagtggcat ggtgatgtgg cagtgaaaat gttgaatgtg acagcaccta cacctcagca     540
gttacaagcc ttcaaaaatg aagtaggagt actcaggaaa cacgacatg tgaatatcct     600
actcttcatg ggctattcca caaagccaca actggctatt gttacccagt ggtgtgaggg     660
ctccagcttg tatcaccatc tccatatcat tgagaccaaa tttgagatga tcaaacttat     720
agatattgca cgacagactg cacagggcat ggattactta cacgccaagt caatcatcca     780
cagagaccct aagagaaata atatatttct tcatgaagac ctcacagtaa aataggtga     840
ttttggtcta gctacagtga aatctcgatg gagtgggtcc catcagtttg aacagttgtc     900
tggatccatt ttgtggatgg caccagaagt catcagaatg caagataaaa atccatacag     960
ctttcagtca gatgtatatg catttggaat tgttctgtat gaattgatga ctggacagtt    1020
accttattca aacatcaaca cagggaccca gataattttt atggtgggac gaggatacct    1080
gtctccagat ctcagtaagg tacggagtaa ctgtccaaaa gccatgaaga gattaatggc    1140
agagtgcctc aaaaagaaaa gagatgagag accactcttt ccccaaattc tcgcctctat    1200
tgagctgctg gcccgctcat tgccaaaaat tcaccgcagt gcatcagaac cctccttgaa    1260
tcgggctggt ttccaaacag aggattttag tctatatgct tgtgcttctc caaaacacc    1320
catccaggca gggggatatg gtgcgttcc tgtccactga aacaaatgag tgagagagtt    1380
caggagagta gcaacaaaag gaaaataaat gaacatatgt ttgcttatat gttaaattga    1440
ataaaatact ctcttttttt ttaaggtgaa ccaaagaaca cttgtgtggt taaagactag    1500
atataatttt tccccaaact aaaatttata cttaacattg gatttttaac atccaagggt    1560
taaaatacat agacattgct aaaaattggc agagcctctt ctagaggctt tactttctgt    1620
tccgggtttg tatcattcac ttggttattt taagtagtaa acttcagttt tcatgcaac    1680
ttttgttgcc agctatcaca tgtccactag ggactccaga agaagaccct acctatgcct    1740
gtgtttgcag gtgagaagtt ggcagtcggt tagcctgggt tagataaggc aaactgaaca    1800
gatctaattt aggaagtcag tagaatttaa taattctatt attattctta ataatttttc    1860
tataactatt tcttttttata acaatttgga aaatgtggat gtcttttatt tccttgaagc    1920
aataaactaa gtttctttt ataaaaa                                          1947
```

<210> SEQ ID NO 15
<211> LENGTH: 2313
<212> TYPE: DNA
<213> ORGANISM: Homo sapiens

<400> SEQUENCE: 15

```
cgcctccctt ccccctcccc gcccgacagc ggccgctcgg gccccggctc tcggttataa      60
gatggcggcg ctgagcggtg gcggtggtgg cggcgcggag ccgggccagg ctctgttcaa     120
```

```
cggggacatg gagcccgagg ccggcgccgg cgccggcgcc gcggcctctt cggctgcgga      180
ccctgccatt ccggaggagg tgtggaatat caaacaaatg attaagttga cacaggaaca      240
tatagaggcc ctattggaca aatttggtgg ggagcataat ccaccatcaa tatatctgga      300
ggcctatgaa gaatacacca gcaagctaga tgcactccaa caaagagaac aacagttatt      360
ggaatctctg gggaacggaa ctgattttc tgtttctagc tctgcatcaa tggataccgt       420
tacatcttct tcctcttcta gcctttcagt gctaccttca tctctttcag ttttcaaaa       480
tcccacagat gtggcacgga gcaaccccaa gtcaccacaa aaacctatcg ttagagtctt      540
cctgcccaac aaacagagga cagtggactt gattagagac caaggatttc gtggtgatgg      600
aggatcaacc acaggtttgt ctgctacccc ccctgcctca ttacctggct cactaactaa      660
cgtgaaagcc ttacagaaat ctccaggacc tcagcgagaa aggaagtcat cttcatcctc      720
agaagacagg aatcgaatga aaacacttgg tagacgggac tcgagtgatg attgggagat      780
tcctgatggg cagattacag tgggacaaag aattggatct ggatcatttg aacagtcta      840
caagggaaag tggcatggtg atgtggcagt gaaaatgttg aatgtgacag cacctacacc      900
tcagcagtta caagccttca aaatgaagt aggagtactc aggaaaacac gacatgtgaa       960
tatcctactc ttcatgggct attccacaaa gccacaactg gctattgtta cccagtggtg     1020
tgagggctcc agcttgtatc accatctcca tatcattgag accaaatttg agatgatcaa     1080
acttatagat attgcacgac agactgcaca gggcatggat tacttacacg ccaagtcaat     1140
catccacaga gacctcaaga gaataatat atttcttcat gaagacctca cagtaaaaat       1200
aggtgatttt ggtctagcta cagtgaaatc tcgatggagt gggtcccatc agtttgaaca     1260
gttgtctgga tccattttgt ggatggcacc agaagtcatc agaatgcaag ataaaaatcc     1320
atacagcttt cagtcagatg tatatgcatt tggaattgtt ctgtatgaat tgatgactgg     1380
acagttacct tattcaaaca tcaacaacag ggaccagata ttttttatgg tgggacgagg     1440
ataccctgtct ccagatctca gtaaggtacg gagtaactgt ccaaaagcca tgaagagatt    1500
aatggcagag tgcctcaaaa agaaaagaga tgagagacca ctctttccc aaattctcgc     1560
ctctattgag ctgctggccc gctcattgcc aaaaaattcac cgcagtgcat cagaaccctc     1620
cttgaatcgg gctggtttcc aaacagagga ttttagtcta tatgcttgtg cttctccaaa     1680
aacacccatc caggcagggg gatatggtgc gtttcctgtc cactgaaaca atgagtgag     1740
agagttcagg agagtagcaa caaaaggaaa ataaatgaac atatgtttgc ttatatgtta     1800
aattgaataa aatactctct tttttttaa ggtgaaccaa agaacacttg tgtggttaaa     1860
gactagatat aattttcccc caaactaaaa tttatactta acattggat tttaacatcc      1920
aagggttaaa atacatagac attgctaaaa attggcagag cctcttctag aggctttact     1980
ttctgttccg ggtttgtatc attcacttgg ttattttaag tagtaaactt cagtttctca     2040
tgcaacttt gttgccagct atcacatgtc cactagggac tccagaagaa gaccctacct      2100
atgcctgtgt ttgcaggtga gaagttggca gtcggttagc ctgggttaga taaggcaaac     2160
tgaacagatc taatttagga agtcagtaga atttaataat tctattatta ttcttaataa     2220
ttttctata actatttctt tttataacaa tttggaaaat gtggatgtct tttattcct     2280
tgaagcaata aactaagttt ctttttataa aaa                                   2313
```

<210> SEQ ID NO 16
<211> LENGTH: 432
<212> TYPE: PRT
<213> ORGANISM: Homo sapiens -continued

<400> SEQUENCE: 16

Met Ala Ala Leu Ser Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Asp Leu
        35                  40                  45

Ile Arg Asp Gln Gly Phe Arg Gly Asp Gly Ser Thr Thr Gly Leu
50                  55                  60

Ser Ala Thr Pro Pro Ala Ser Leu Pro Gly Ser Leu Thr Asn Val Lys
65                  70                  75                  80

Ala Leu Gln Lys Ser Pro Gly Pro Gln Arg Glu Arg Lys Ser Ser Ser
            85                  90                  95

Ser Ser Glu Asp Arg Asn Arg Met Lys Thr Leu Gly Arg Arg Asp Ser
            100                 105                 110

Ser Asp Asp Trp Glu Ile Pro Asp Gly Gln Ile Thr Val Gly Gln Arg
            115                 120                 125

Ile Gly Ser Gly Ser Phe Gly Thr Val Tyr Lys Gly Lys Trp His Gly
            130                 135                 140

Asp Val Ala Val Lys Met Leu Asn Val Thr Ala Pro Thr Pro Gln Gln
145                 150                 155                 160

Leu Gln Ala Phe Lys Asn Glu Val Gly Val Leu Arg Lys Thr Arg His
            165                 170                 175

Val Asn Ile Leu Leu Phe Met Gly Tyr Ser Thr Lys Pro Gln Leu Ala
            180                 185                 190

Ile Val Thr Gln Trp Cys Glu Gly Ser Ser Leu Tyr His His Leu His
            195                 200                 205

Ile Ile Glu Thr Lys Phe Glu Met Ile Lys Leu Ile Asp Ile Ala Arg
            210                 215                 220

Gln Thr Ala Gln Gly Met Asp Tyr Leu His Ala Lys Ser Ile Ile His
225                 230                 235                 240

Arg Asp Leu Lys Ser Asn Asn Ile Phe Leu His Glu Asp Leu Thr Val
            245                 250                 255

Lys Ile Gly Asp Phe Gly Leu Ala Thr Val Lys Ser Arg Trp Ser Gly
            260                 265                 270

Ser His Gln Phe Glu Gln Leu Ser Gly Ser Ile Leu Trp Met Ala Pro
            275                 280                 285

Glu Val Ile Arg Met Gln Asp Lys Asn Pro Tyr Ser Phe Gln Ser Asp
290                 295                 300

Val Tyr Ala Phe Gly Ile Val Leu Tyr Glu Leu Met Thr Gly Gln Leu
305                 310                 315                 320

Pro Tyr Ser Asn Ile Asn Asn Arg Asp Gln Ile Ile Phe Met Val Gly
            325                 330                 335

Arg Gly Tyr Leu Ser Pro Asp Leu Ser Lys Val Arg Ser Asn Cys Pro
            340                 345                 350

Lys Ala Met Lys Arg Leu Met Ala Glu Cys Leu Lys Lys Lys Arg Asp
            355                 360                 365

Glu Arg Pro Leu Phe Pro Gln Ile Leu Ala Ser Ile Glu Leu Leu Ala
            370                 375                 380

Arg Ser Leu Pro Lys Ile His Arg Ser Ala Ser Glu Pro Ser Leu Asn
385                 390                 395                 400

```
Arg Ala Gly Phe Gln Thr Glu Asp Phe Ser Leu Tyr Ala Cys Ala Ser
                405                 410                 415

Pro Lys Thr Pro Ile Gln Ala Gly Gly Tyr Gly Ala Phe Pro Val His
            420                 425                 430
```

<210> SEQ ID NO 17
<211> LENGTH: 374
<212> TYPE: PRT
<213> ORGANISM: Homo sapiens

<400> SEQUENCE: 17

```
Met Ala Ala Leu Ser Gly Gly Gly Gly Ala Glu Pro Gly Gln
1               5                   10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Lys Thr
            35                  40                  45

Leu Gly Arg Arg Asp Ser Ser Asp Asp Trp Glu Ile Pro Asp Gly Gln
50                  55                  60

Ile Thr Val Gly Gln Arg Ile Gly Ser Gly Ser Phe Gly Thr Val Tyr
65                  70                  75                  80

Lys Gly Lys Trp His Gly Asp Val Ala Val Lys Met Leu Asn Val Thr
                85                  90                  95

Ala Pro Thr Pro Gln Gln Leu Gln Ala Phe Lys Asn Glu Val Gly Val
            100                 105                 110

Leu Arg Lys Thr Arg His Val Asn Ile Leu Leu Phe Met Gly Tyr Ser
        115                 120                 125

Thr Lys Pro Gln Leu Ala Ile Val Thr Gln Trp Cys Glu Gly Ser Ser
130                 135                 140

Leu Tyr His His Leu His Ile Ile Glu Thr Lys Phe Glu Met Ile Lys
145                 150                 155                 160

Leu Ile Asp Ile Ala Arg Gln Thr Ala Gln Gly Met Asp Tyr Leu His
                165                 170                 175

Ala Lys Ser Ile Ile His Arg Asp Leu Lys Ser Asn Asn Ile Phe Leu
            180                 185                 190

His Glu Asp Leu Thr Val Lys Ile Gly Asp Phe Gly Leu Ala Thr Val
        195                 200                 205

Lys Ser Arg Trp Ser Gly Ser His Gln Phe Glu Gln Leu Ser Gly Ser
210                 215                 220

Ile Leu Trp Met Ala Pro Glu Val Ile Arg Met Gln Asp Lys Asn Pro
225                 230                 235                 240

Tyr Ser Phe Gln Ser Asp Val Tyr Ala Phe Gly Ile Val Leu Tyr Glu
                245                 250                 255

Leu Met Thr Gly Gln Leu Pro Tyr Ser Asn Ile Asn Asn Arg Asp Gln
            260                 265                 270

Ile Ile Phe Met Val Gly Arg Gly Tyr Leu Ser Pro Asp Leu Ser Lys
        275                 280                 285

Val Arg Ser Asn Cys Pro Lys Ala Met Lys Arg Leu Met Ala Glu Cys
290                 295                 300

Leu Lys Lys Lys Arg Asp Glu Arg Pro Leu Phe Pro Gln Ile Leu Ala
305                 310                 315                 320

Ser Ile Glu Leu Leu Ala Arg Ser Leu Pro Lys Ile His Arg Ser Ala
                325                 330                 335

Ser Glu Pro Ser Leu Asn Arg Ala Gly Phe Gln Thr Glu Asp Phe Ser
            340                 345                 350
```

```
Leu Tyr Ala Cys Ala Ser Pro Lys Thr Pro Ile Gln Ala Gly Gly Tyr
            355                 360                 365

Gly Ala Phe Pro Val His
    370

<210> SEQ ID NO 18
<211> LENGTH: 554
<212> TYPE: PRT
<213> ORGANISM: Homo sapiens

<400> SEQUENCE: 18

Met Ala Ala Leu Ser Gly Gly Gly Gly Gly Ala Glu Pro Gly Gln
1               5                  10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Asp Leu Ile Arg Asp Gln Gly Phe
                165                 170                 175

Arg Gly Asp Gly Gly Ser Thr Thr Gly Leu Ser Ala Thr Pro Pro Ala
            180                 185                 190

Ser Leu Pro Gly Ser Leu Thr Asn Val Lys Ala Leu Gln Lys Ser Pro
        195                 200                 205

Gly Pro Gln Arg Glu Arg Lys Ser Ser Ser Ser Glu Asp Arg Asn
210                 215                 220

Arg Met Lys Thr Leu Gly Arg Arg Asp Ser Ser Asp Asp Trp Glu Ile
225                 230                 235                 240

Pro Asp Gly Gln Ile Thr Val Gly Gln Arg Ile Gly Ser Gly Ser Phe
                245                 250                 255

Gly Thr Val Tyr Lys Gly Lys Trp His Gly Asp Val Ala Val Lys Met
            260                 265                 270

Leu Asn Val Thr Ala Pro Thr Pro Gln Gln Leu Gln Ala Phe Lys Asn
        275                 280                 285

Glu Val Gly Val Leu Arg Lys Thr Arg His Val Asn Ile Leu Leu Phe
    290                 295                 300

Met Gly Tyr Ser Thr Lys Pro Gln Leu Ala Ile Val Thr Gln Trp Cys
305                 310                 315                 320

Glu Gly Ser Ser Leu Tyr His His Leu His Ile Ile Glu Thr Lys Phe
                325                 330                 335

Glu Met Ile Lys Leu Ile Asp Ile Ala Arg Gln Thr Ala Gln Gly Met
            340                 345                 350
```

```
Asp Tyr Leu His Ala Lys Ser Ile Ile His Arg Asp Leu Lys Ser Asn
            355                 360                 365

Asn Ile Phe Leu His Glu Asp Leu Thr Val Lys Ile Gly Asp Phe Gly
        370                 375                 380

Leu Ala Thr Val Lys Ser Arg Trp Ser Gly His Gln Phe Glu Gln
385                 390                 395                 400

Leu Ser Gly Ser Ile Leu Trp Met Ala Pro Glu Val Ile Arg Met Gln
                405                 410                 415

Asp Lys Asn Pro Tyr Ser Phe Gln Ser Asp Val Tyr Ala Phe Gly Ile
            420                 425                 430

Val Leu Tyr Glu Leu Met Thr Gly Gln Leu Pro Tyr Ser Asn Ile Asn
        435                 440                 445

Asn Arg Asp Gln Ile Ile Phe Met Val Gly Arg Gly Tyr Leu Ser Pro
450                 455                 460

Asp Leu Ser Lys Val Arg Ser Asn Cys Pro Lys Ala Met Lys Arg Leu
465                 470                 475                 480

Met Ala Glu Cys Leu Lys Lys Lys Arg Asp Glu Arg Pro Leu Phe Pro
                485                 490                 495

Gln Ile Leu Ala Ser Ile Glu Leu Leu Ala Arg Ser Leu Pro Lys Ile
            500                 505                 510

His Arg Ser Ala Ser Glu Pro Ser Leu Asn Arg Ala Gly Phe Gln Thr
        515                 520                 525

Glu Asp Phe Ser Leu Tyr Ala Cys Ala Ser Pro Lys Thr Pro Ile Gln
            530                 535                 540

Ala Gly Gly Tyr Gly Ala Phe Pro Val His
545                 550

<210> SEQ ID NO 19
<211> LENGTH: 496
<212> TYPE: PRT
<213> ORGANISM: Homo sapiens

<400> SEQUENCE: 19

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
        50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Lys Thr Leu Gly Arg Asp Ser
                165                 170                 175
```

-continued

Ser Asp Asp Trp Glu Ile Pro Asp Gly Gln Ile Thr Val Gly Gln Arg
            180                 185                 190

Ile Gly Ser Gly Ser Phe Gly Thr Val Tyr Lys Gly Lys Trp His Gly
        195                 200                 205

Asp Val Ala Val Lys Met Leu Asn Val Thr Ala Pro Thr Pro Gln Gln
    210                 215                 220

Leu Gln Ala Phe Lys Asn Glu Val Gly Val Leu Arg Lys Thr Arg His
225                 230                 235                 240

Val Asn Ile Leu Leu Phe Met Gly Tyr Ser Thr Lys Pro Gln Leu Ala
                245                 250                 255

Ile Val Thr Gln Trp Cys Glu Gly Ser Ser Leu Tyr His His Leu His
            260                 265                 270

Ile Ile Glu Thr Lys Phe Glu Met Ile Lys Leu Ile Asp Ile Ala Arg
        275                 280                 285

Gln Thr Ala Gln Gly Met Asp Tyr Leu His Ala Lys Ser Ile Ile His
    290                 295                 300

Arg Asp Leu Lys Ser Asn Asn Ile Phe Leu His Glu Asp Leu Thr Val
305                 310                 315                 320

Lys Ile Gly Asp Phe Gly Leu Ala Thr Val Lys Ser Arg Trp Ser Gly
                325                 330                 335

Ser His Gln Phe Glu Gln Leu Ser Gly Ser Ile Leu Trp Met Ala Pro
            340                 345                 350

Glu Val Ile Arg Met Gln Asp Lys Asn Pro Tyr Ser Phe Gln Ser Asp
        355                 360                 365

Val Tyr Ala Phe Gly Ile Val Leu Tyr Glu Leu Met Thr Gly Gln Leu
    370                 375                 380

Pro Tyr Ser Asn Ile Asn Asn Arg Asp Gln Ile Ile Phe Met Val Gly
385                 390                 395                 400

Arg Gly Tyr Leu Ser Pro Asp Leu Ser Lys Val Arg Ser Asn Cys Pro
                405                 410                 415

Lys Ala Met Lys Arg Leu Met Ala Glu Cys Leu Lys Lys Lys Arg Asp
            420                 425                 430

Glu Arg Pro Leu Phe Pro Gln Ile Leu Ala Ser Ile Glu Leu Leu Ala
        435                 440                 445

Arg Ser Leu Pro Lys Ile His Arg Ser Ala Ser Glu Pro Ser Leu Asn
    450                 455                 460

Arg Ala Gly Phe Gln Thr Glu Asp Phe Ser Leu Tyr Ala Cys Ala Ser
465                 470                 475                 480

Pro Lys Thr Pro Ile Gln Ala Gly Gly Tyr Gly Ala Phe Pro Val His
                485                 490                 495

<210> SEQ ID NO 20
<211> LENGTH: 139
<212> TYPE: DNA
<213> ORGANISM: Homo sapiens

<400> SEQUENCE: 20
gatggcggcg ctgagcggtg gcggtggtgg cggcgcggag ccgggccagg ctctgttcaa    60
cggggacatg gagcccgagg ccggcgccgg cgccggcgcc gcggcctctt cggctgcgga   120
ccctgccatt ccggaggag                                                139

<210> SEQ ID NO 21
<211> LENGTH: 987
<212> TYPE: DNA
<213> ORGANISM: Homo sapiens

```
<400> SEQUENCE: 21
aaaacacttg gtagacggga ctcgagtgat gattgggaga ttcctgatgg gcagattaca        60
gtgggacaaa gaattggatc tggatcattt ggaacagtct acaagggaaa gtggcatggt       120
gatgtggcag tgaaaatgtt gaatgtgaca gcacctacac ctcagcagtt acaagccttc       180
aaaaatgaag taggagtact caggaaaaca cgacatgtga atatcctact cttcatgggc       240
tattccacaa agccacaact ggctattgtt acccagtggt gtgagggctc cagcttgtat       300
caccatctcc atatcattga gaccaaattt gagatgatca aacttataga tattgcacga       360
cagactgcac agggcatgga ttacttacac gccaagtcaa tcatccacag agacctcaag       420
agtaataata tatttcttca tgaagacctc acagtaaaaa taggtgattt tggtctagct       480
acagtgaaat ctcgatggag tgggtcccat cagtttgaac agttgtctgg atccattttg       540
tggatggcac cagaagtcat cagaatgcaa gataaaaatc catacagctt tcagtcagat       600
gtatatgcat ttggaattgt tctgtatgaa ttgatgactg gacagttacc ttattcaaac       660
atcaacaaca gggaccagat aattttatg gtgggacgag gatacctgtc tccagatctc       720
agtaaggtac ggagtaactg tccaaaagcc atgaagagat taatggcaga gtgcctcaaa       780
aagaaaagag atgagagacc actctttccc caaattctcg cctctattga gctgctggcc       840
cgctcattgc caaaaattca ccgcagtgca tcagaaccct ccttgaatcg ggctggtttc       900
caaacagagg attttagtct atatgcttgt gcttctccaa aaacacccat ccaggcaggg       960
ggatatggtg cgtttcctgt ccactga                                           987
```

METHODS AND COMPOSITIONS FOR THE DETECTION OF DRUG RESISTANT BRAF ISOFORMS

CROSS-REFERENCE TO RELATED APPLICATIONS

This application claims priority from U.S. Provisional Application No. 61/519,593 filed May 25, 2011, the contents of which are hereby incorporated by reference in their entirety into the present disclosure.

SEQUENCE LISTING

This application contains a Sequence Listing, created on Apr. 24, 2012; the file, in ASCII format, is designated 3314020A_Sequence Listing_ST25.txt and is 38.3 kilobytes in size. The sequence listing file is hereby incorporated by reference in its entirety into the application.

FIELD OF THE INVENTION

This invention relates generally to splice variants of the BRAF gene and in particular to BRAF splice variants that correlate with resistance to inhibition of activated BRAF. The invention further relates to methods for detecting the presence of gene products of BRAF splice variants.

BACKGROUND OF INVENTION

The v-raf murine sarcoma viral oncogene homolog B1, also known as NS7; BRAF1; RAFB1; B-RAF1; FLJ95109; MGC126806; MGC138284; or BRAF, (as used herein, "BRAF"), is a serine/threonine protein kinase that plays a critical role in the MAP Kinase/ERK signaling pathway which mediates physiological cell functions such as growth and differentiation. Aberrant activation of MAP Kinase/ERK signaling can result in the development and progression of multiple types of cancer. As such, the components of the MAP Kinase/ERK signaling pathway are considered attractive therapeutic targets for cancer treatment. In particular, activating mutations in BRAF have been shown to occur in ~80% of melanoma, ~50% of papillary thyroid cancer, and 10% of colon cancers with an overall occurrence in ~8% in all types of cancer. SEQ ID NO 1 displays the full length mRNA Homo sapiens BRAF mRNA and is from Genebank accession number NM_004333.4. In BRAF, the single nucleotide substitution at nucleotide position 1798 (T→A, thymine to adenine) produces an amino acid substitution at amino acid position 600 (V→E, valine to glutamate) in the catalytic kinase domain resulting in constitutive activation of BRAF (as used herein "V600E" or "BRAF (V600E)"). The V600E mutation accounts for ~90% of all activating BRAF mutations.

Given the importance of activated BRAF and, in particular, BRAFV600E in cancer progression, there has been much effort to develop both pan-RAF and selective BRAF inhibitors as potential therapeutics; multiple agents are currently undergoing clinical evaluation including GSK218436, ARQ 736, PLX3603, PLX4032 (also known as vemurafenib, RG7204 or RO5185426 and herein referred to as "PLX4032"), BMS908662, RAF265, XL281, and BAY 43-9006. Clinical results have shown that tumors harboring activating BRAF mutations show remarkable response, including delay in progression and/or tumor regression, to treatment with such pan-RAF and selective BRAF inhibitors. Despite the initial response to such treatment, the majority of the patients develop resistance to treatment with such pan-RAF and/or BRAF inhibitors within 2-18 months. Preliminary in vitro and animal model experiments have suggested that such acquired resistance can arise from activating mutations in the MAP Kinase/ERK signaling pathway upstream RAS or downstream MEK and from activation of parallel signaling pathways. However, it is still not clear if all cases of resistance are mediated by such mechanisms nor is it clear if such mechanisms are clinically relevant. To date, no compensatory mutations in BRAF itself have been shown to drive said resistance.

Therefore there is a need in the art for further evaluating the mechanism of acquired resistance and to validate such mechanisms in the clinical setting. This will allow more complete diagnostic tests to be developed in order to stratify patients for treatment and will provide an opportunity to better tailor treatment strategies in the resistant patient. Further, there is a need in the art for novel second-line therapeutics to treat patients who become resistant to treatment with pan-RAF and/or BRAF inhibitor(s) and exhibit progression or relapse despite an initial response to BRAF inhibition.

SUMMARY OF THE INVENTION

The present invention is based on the identification of novel 5' BRAF splice variants in tumor cells and cell lines that are resistant to BRAF inhibitors. The splice variants are the results of splicing events in which exons or portions thereof of the regulatory domain of BRAF are lost.

In one aspect, therefore, the invention relates to purified polypeptides comprising the amino acid sequence of a BRAF(V600E) splice variant. These include splice variants in which all or some portion of exons 2-10 have been deleted. Included are BRAF(V600E) splice variants containing a deletion of exons 2-10, exons 4-10, exons 2-8, exons 4-8, etc. Polypeptides of the BRAF(V600E) splice variants disclosed herein will therefore, contain a deletion of amino acids encoded by the deleted exons. These include without limitation those having the amino acid sequence of any of SEQ ID NOS: 16-19, for example.

In a related aspect, the invention relates to isolated nucleic acids that encode the BRAF(V600E) splice variant polypeptides disclosed herein. Nucleic acids disclosed herein include: a nucleic acid having the nucleotide sequence of BRAF(V600E) in which exons 2-10 of BRAF(V600E) are deleted, giving rise to a splice variant in which exon 1 is joined to exons 11-18 of BRAF(V600E); a nucleic acid having the nucleotide sequence of BRAF(V600E) in which exons 2-8 have been deleted, giving rise to a splice variant in which exon 1 is joined to exons 9-18 of BRAF(V600E); a nucleic acid having the nucleotide sequence of BRAF (V600E) in which exons 4-8 are deleted, giving rise to a splice variant in which exons 1-3 are joined to exons 11-18 of BRAF(V600E); a nucleic acid having the nucleotide sequence of BRAF(V600E) in which exons 2-8 have been deleted giving rise to a splice variant in which exons 1-3 are joined to exons 9-18 of BRAF(V600E); and so on. The nucleotide sequences of some embodiments of splice variants disclosed herein are set forth in SEQ ID NOS: 13-15.

In yet another related aspect, the invention relates to vectors comprising the nucleic acids disclosed herein as well as cells that have been transfected with these vectors to express the BRAF(V600E) splice variants. Isolated cells that endogenously express the BRAF(V600E) splice variants disclosed herein are also encompassed by the invention. These include, for example, SKMEL-239 clones C1-05.

In another aspect, the invention relates to synthetic oligonucleotides that hybridize under stringent conditions to a gene product encoded by the BRAF(V600E) splice variants. These oligonucleotides find use as primers and probes for techniques such as PCR and microarray technology for the detection, identification and characterization of BRAF (V600E) splice variants in a sample. Oligonucleotides that specifically hybridize to a region of exon 1 of BRAF (V600E) (SEQ ID NO: 20), a region of exons 11-18 (SEQ ID NO: 21) and/or to new splice junctions (e.g. 1-11, 1-9, 3-11 and 3-9) created by the deletion of one or more exons (e.g., SEQ ID NOS: 4, 6, 7) are advantageous. Synthetic oligonucleotides may be from about 10-30 nucleotides in length; in some embodiments, synthetic oligonucleotides are about 18-21 nucleotides in length. In other embodiments, a synthetic oligonuceotide that hybridizes to a nucleic acid comprising the nucleotide sequence of SEQ ID NO: 7 plus 0 to 12 contiguous nucleotides of SEQ ID NO: 13 flanking SEQ ID NO: 7 may be useful as a 3-11 Splice junction primer, a synthetic oligonuceotide that hybridizes to a nucleic acid comprises the nucleotide sequence of SEQ ID NO: 4 plus 0 to 12 contiguous nucleotides of SEQ ID NO: 14 flanking SEQ ID NO: 4 may be useful as a 1-9 Splice junction primer and a synthetic oligonuceotide that hybridizes to a nucleic acid comprising the nucleotide sequence of SEQ ID NO: 6 plus 0 to 12 contiguous nucleotides of SEQ ID NO: 15 flanking SEQ ID NO: 6 may be useful as a 3-9 Splice junction primer.

In a related aspect, the invention relates to methods for detecting BRAF(V600E) splice variants in a sample using primers and/or probes disclosed herein. In one embodiment, the method comprises contacting a sample with primers or probes that are specific for a gene product of one or more BRAF(V600E) splice variants. Gene products include mRNA, cDNA and protein. Primer pairs of the invention may include a primer pair comprising a first primer with the nucleotide sequence of SEQ ID NO: 4 and a second primer with the nucleotide sequence of SEQ ID NO: 5; a primer pair comprising a first primer with the nucleotide sequence of SEQ ID NO: 6 and a second primer with the nucleotide sequence of SEQ ID NO: 5; a primer pair comprising a first primer with the nucleotide sequence of SEQ ID NO: 7 and a second primer with the nucleotide sequence of SEQ ID NO: 8 and the like. A primer set for the detection of multiple variants includes a primer pair for each variant.

In general, oligonucleotides of the invention may be used in pairs of forward and reverse primers and in sets of pairs that are able to detect multiple variants in accordance with methods well known to those of skill in the art. Accordingly they may be employed in the detection of BRAF(V600E) variants using any method known to the skilled artisan for analyzing gene products.

In another related aspect, the invention relates to a method of detecting a variant form of BRAF mRNA, the method comprising (a) combining a sample possibly containing a variant form of BRAF cDNA selected from the group consisting of a BRAF(V600E) gene product comprising exons 1 and 9-18 of BRAF(V600E) DNA;

a BRAF(V600E) gene product comprising exons 1-3 and 9-18 of BRAF(V600E) DNA; and a BRAF(V600E) gene product comprising exons 1-3 and 11-18 of BRAF(V600E) DNA with: (i) a forward primer capable of hybridizing to an exon 1-9 splice junction (SEQ ID NO: X) of the cDNA encoding the variant BRAF; and a reverse primer that is at least 10 nucleotides long and corresponds to a sequence from BRAF exons 11-18; (ii) a forward primer capable of hybridizing to an exon 3-9 splice junction (SEQ ID NO: X) of the cDNA encoding the variant BRAF; and a reverse primer that is at least 10 nucleotides long and corresponds to a sequence from BRAF exons 11-18; or (iii) a forward primer capable of hybridizing to an exon 3-11 splice junction (SEQ ID NO: X) of the cDNA encoding the variant BRAF and a reverse primer that is at least 10 nucleotides long and corresponds to a sequence from BRAF exons 11-18; or a combination of (i), (ii), and (iii). The method further comprises combining the sample with reagents for PCR to form a mixture and subjecting the mixture to thermocycling, and determining the absence or the presence of the cDNA corresponding to at least a portion of the variant form of BRAF mRNA in the thermocycled mixture, wherein the presence of the cDNA indicates that the sample comprises a variant form of BRAF. In one embodiment, detection of three variants is desired.

In another aspect, the invention also relates to a method of detecting a variant form of BRAF comprising:

(a) combining a sample with:

(i) a first primer capable of hybridizing under stringent conditions to an exon 1-9 splice junction of a nucleic acid encoding a BRAF (V600E) variant; and a second primer that hybridizes to a sequence from exons 11-18 of BRAF(V600E);

(ii) a third primer capable of hybridizing under stringent conditions to an exon 3-9 splice junction of a nucleic acid encoding a BRAF (V600E) variant; and a fourth primer that hybridizes to a sequence from exons 11-18 of BRAF(V600E);

(iii) a fifth primer capable of hybridizing under stringent conditions to an exon 3-11 splice junction of a nucleic acid encoding a BRAF(V600E) variant and a sixth primer that hybridizes to a sequence from exons 11-18 of BRAF(V600E); or (iv) any combination of (i), (ii), and (iii); and (b) combining the sample with reagents for PCR to form a mixture and subjecting the mixture to thermocycling, and determining the absence or the presence of a nucleic acid corresponding to at least a portion of the variant form of BRAF mRNA in the thermocycled mixture, wherein the presence of the nucleic acid indicates that the sample comprises a variant form of BRAF.

In a related aspect, therefore, the present invention provides a kit comprising at least one PCR primer as described herein. Such kit can further comprise reagents required for PCR and instructions for practicing the methods of the present invention.

In yet another related aspect, the invention relates to a gene expression panel or array for detecting a splice variant of BRAF, wherein the panel or array comprises probes capable of detecting splice junctions of BRAF.

In another aspect, the compositions of the invention can be used to perform a method to determine the resistance of a cell or tissue to a BRAF inhibitor, the method comprising (a) contacting a sample containing a gene product isolated from said cell or tissue with a detectable primer/probe of the invention that binds to a splice variant of BRAF(V600E); and (b) measuring the amount of detectable primer/probe to determine the presence in said sample of a BRAF(V600E) splice variant, wherein the presence of said splice variant indicates that the cell or tissue is resistant to the BRAF inhibitor.

In a related aspect, the invention relates to an in vitro method for monitoring vemurafenib treatment in an subject, the method comprising:

(a) contacting a gene expression product from a melanoma cell or tumor sample from the subject with a detectable probe or primer that can hybridize to a BRAF(V600E) splice variant in said sample;

(b) measuring the amount of detectable probe or primer in said sample to determine the presence of said BRAF (V600E) splice variant, wherein the presence of said BRAF(V600E) splice variant indicates that the cell or tumor is resistant to vemurafenib. The BRAF(V600E) variant may have a nucleotide sequence selected from SEQ ID NO: 13, SEQ ID NO: 14 and SEQ ID NO: 15.

In yet another aspect, the invention provides a cell-based method of screening a test compound for use as a RAS-independent RAF inhibitor, said method comprising:

(a) contacting a cell comprising a BRAF(V600E) splice variant with said test compound under conditions suitable for cell growth;

(b) measure the amount of cell growth and/or cell death of cells grown in the presence and absence of the test compound;

(c) compare the amount of cell growth and/or cell death of cells grown in the presence and absence of the test compound, wherein increased cell death and/or decreased cell growth in the presence of said test compound indicates that said test compound has RAS-independent BRAF inhibitory activity.

In yet another related aspect, the invention relates to a method of screening a test compound for use as a RAS-independent BRAF inhibitor, said method comprising:

(a) contacting a sample that comprises BRAF(V600E) splice variant polypeptides with said test compound;

(b) measuring the amount of dimerization of said BRAF (V600E) splice variant polypeptides in said sample in the presence and absence of the test compound;

(c) compare the amount of dimerization in the presence and absence of the test compound, wherein a decrease in dimerization in the presence of said test compound compared with the amount of dimerization in the absence of said test compound indicates that said test compound has RAS-independent BRAF inhibitory activity. The measuring step may be performed using an assay selected from the group consisting of western blot, immunoprecipitation, Förster resonance energy transfer (FRET), or bimolecular fluorescence complementation. (BiFC).

DESCRIPTION OF THE DRAWINGS

FIG. 1A shows IC50 curves for the SKMEL-239 parental cell line and five PLX4032-resistant clones treated with PLX4032 for 5 days.

FIG. 1B shows the effects of 2 µM PLX4032 at various time points on ERK signaling in parental (Par) and resistant clones (C1-5).

FIG. 1C shows a Western blot for components of the ERK and AKT signaling pathways in parental and resistant clones treated with 2 µM PLX4032 for 24 hours.

FIG. 1D shows the dose-response of pMEK and pERK downregulation at 1 hour to increasing concentrations of PLX4032 in parental and two representative resistant clones (C3 and C5).

FIG. 1E shows a graphic representation of the chemiluminescent signal intensities from 1D and determination of IC50s for inhibition of MEK phosphorylation by PLX4032 in the parental and C3 and C5 clones.

FIG. 2A shows the PCR analysis of BRAF in cDNA from parental (P) and C3 cells. PCR primers of the present invention [SEQ ID NOS 2 and 3] were used to amplify the BRAF gene. Sequencing of the 1.7 kb product expressed in the C3 clone, but not in parental cells, revealed an in frame deletion of five exons (exons 4-8) in cis with the V600E mutation resulting in the creation of a novel splice junction joining exon 3 and exon 9 (referred to herein as the "3_9 splice junction"). The expected protein product from the 1.7 kb mRNA has 554 amino acids and a predicted molecular weight of 61 kd.

FIG. 2B. Full length wild-type BRAF and the novel 1.7 kb/61 kd splice variant of BRAF(V600E) lacking exons 4-8 (referred to herein as "p61 BRAF(V600E)") were cloned into a pcDNA3.1 vector with a FLAG tag at the C-terminus and expressed in 293H cells. The effect of PLX4032 (2 µM for 1 hour) on ERK signaling in the 293H cells expressing p61 BRAF(V600E) was analyzed by Western blot for pMEK and pERK.

FIG. 2C. To compare levels of dimerization, 293H cells co-expressing FLAG tagged and c-terminal V5-tagged p61BRAF(V600E), full length BRAF(V600E) and the corresponding dimerization-deficient mutants p61 BRAF (V600E/R509H) and BRAF(V600E/R509H) were lysed followed by immunoprecipitation with FLAG antibody. Western blots with V5 or FLAG antibodies were performed as indicated.

FIG. 2D shows a comparison of MEK/ERK activation and sensitivity of ERK signaling to 2 µM PLX4032 treatment for 1 hour in 293H cells expressing either Flag-tagged BRAF(V600E) or the dimerization mutant Flag-tagged BRAF(V600E/R509H).

FIG. 2E. Constructs expressing V5-tagged BRAF (V600E), p61 BRAF(V600E) or the dimerization mutant p61 BRAF(V600E/R509H) were transfected into 293H cells and treated with 2 µM PLX4032 for 1 hour.

FIG. 3A. PCR analysis of cDNA derived from tumor samples using PCR primers of the present invention [SEQ ID NOS 2 and 3]. In samples with only one band (full-length BRAF), the inventors of the present invention detected both BRAF(V600E) and wild-type BRAF (bands 1+2). In resistant tumor samples expressing shorter transcripts, the shorter transcript was a splice variant of BRAF(V600E) (bands 3, 4, 5). The figure shows samples from three patients with acquired resistance to PLX4032: pre- and post-treatment samples from patient I and post-treatment samples from patients II and III. A tumor sample from a patient with de novo resistance to PLX4032 (patient IV) is also shown.

FIG. 3B. Representative Sanger sequencing trace showing the novel BRAF splice junction joining exon 3 and exon 11 (referred to herein as the "3_11 splice junction") (i.e. novel 5' BRAF splice variant with deletion of exons 4-10) in the tumor sample obtained at the time of acquired resistance from patient I, compared to the full-length transcript derived from the pre-treatment sample from the same patient.

FIG. 3C shows the exon organization of the novel 5' BRAF splice variants found in tumors from three patients that relapsed on PLX4032. The variant from patient II was identical to the one identified in the C1, C3 and C4 PLX4032-resistant SKMEL-239 clones.

In the context of low RAS activity, the N' terminal regulatory domain(s) of BRAF prevents dimerization and thus BRAF(V600E) exists predominantly as a monomer. Deletion of the RAS binding domain allows p61 BRAF (V600E) to dimerize even in the setting of low RAS activity. Under these conditions, drug binding promotes the active state of p61 BRAF(V600E), stabilizing in trans the active state of the non-drug-bound protomer within the dimer. The mechanism is reminiscent of the phenomenon of transactivation in the wild-type BRAF context, but with RAF kinase already in a highly active state, further induction of ERK signaling does not occur. The result is a failure of the RAF inhibitor to downregulate ERK signaling.

Figure 5A:
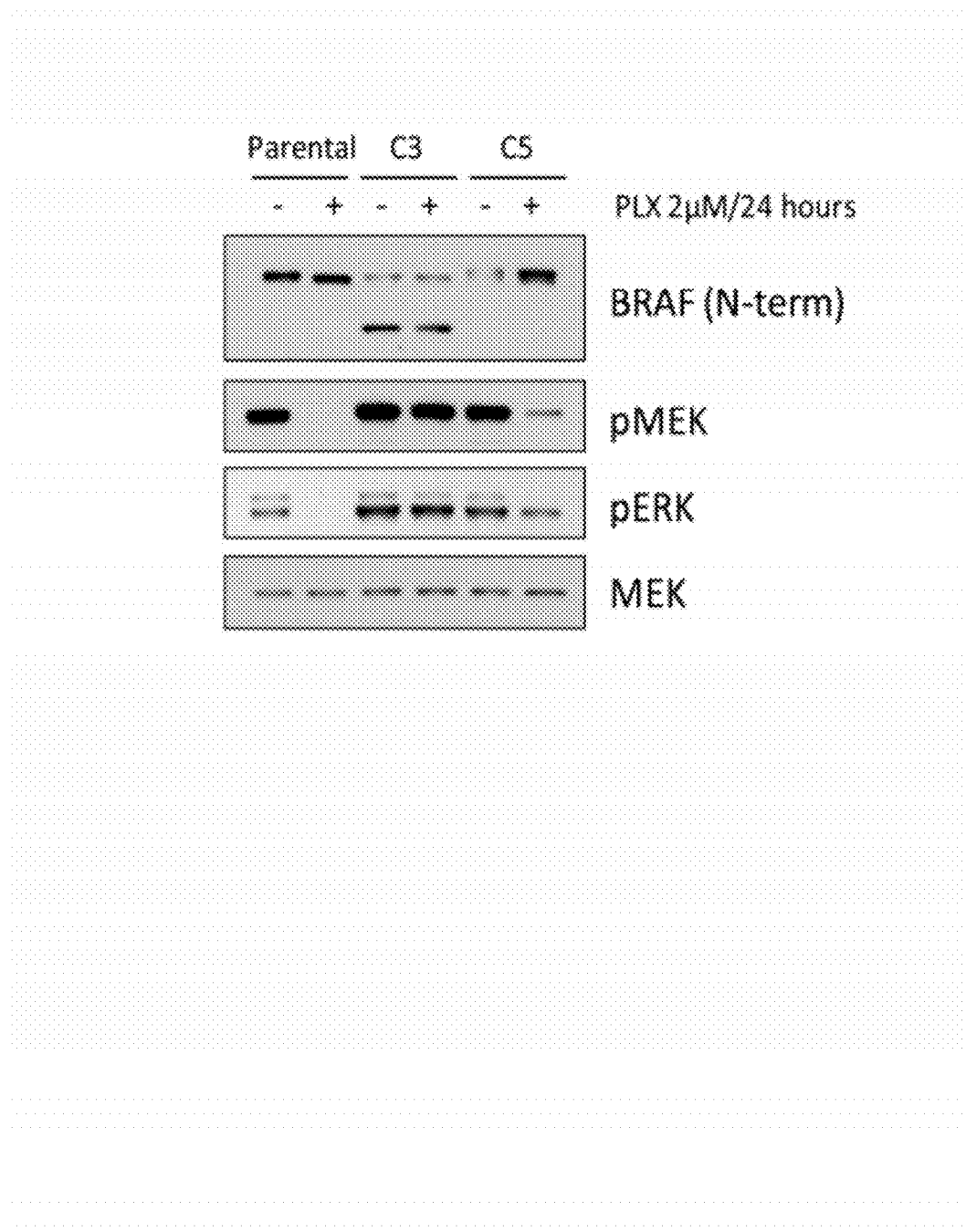
Figure 5B:
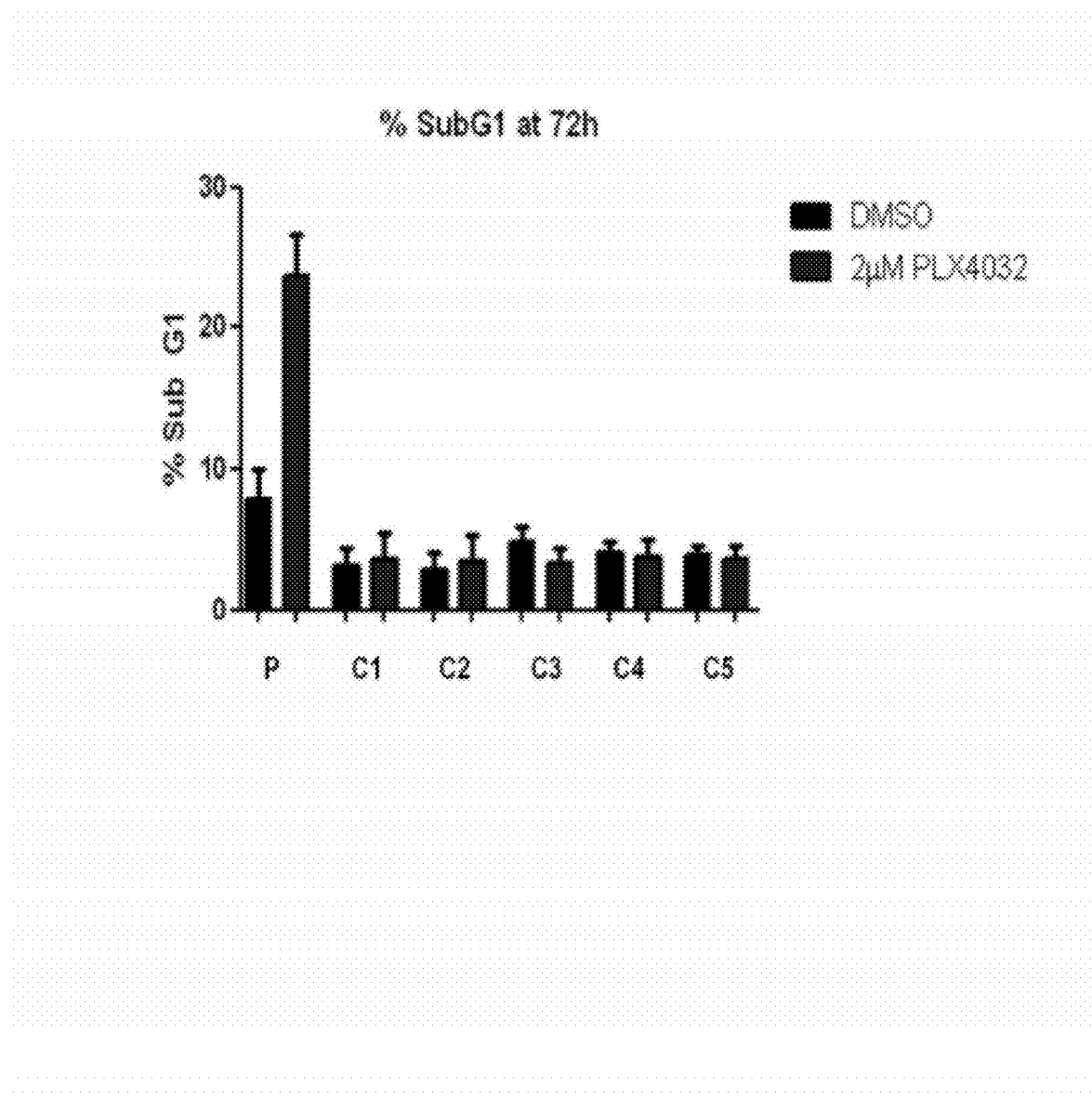

FIGS. 5A-5B shows the effects of PLX4032 on ERK pathway activation and survival in parental SKMEL-239 cells and the PLX4032-resistant clones.

FIG. 5A shows immunoblots of BRAF, phosphorylated MEK and ERK and total MEK. Cells were treated with 2 µM PLX4032 for 24 hours. B. PLX4032 induced cell death in parental SKMEL-239 cells but not in the five resistant clones as measured by accumulation of a sub-G1 peak by FACS analysis.

Figure 6A:
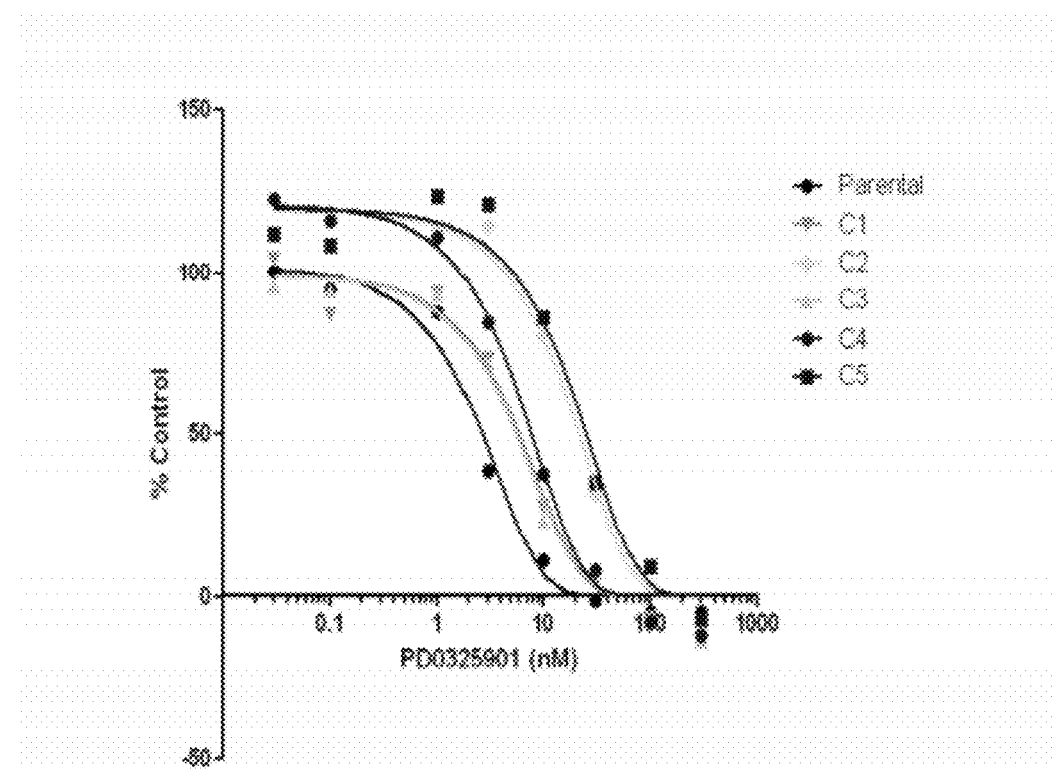
Figure 6B:
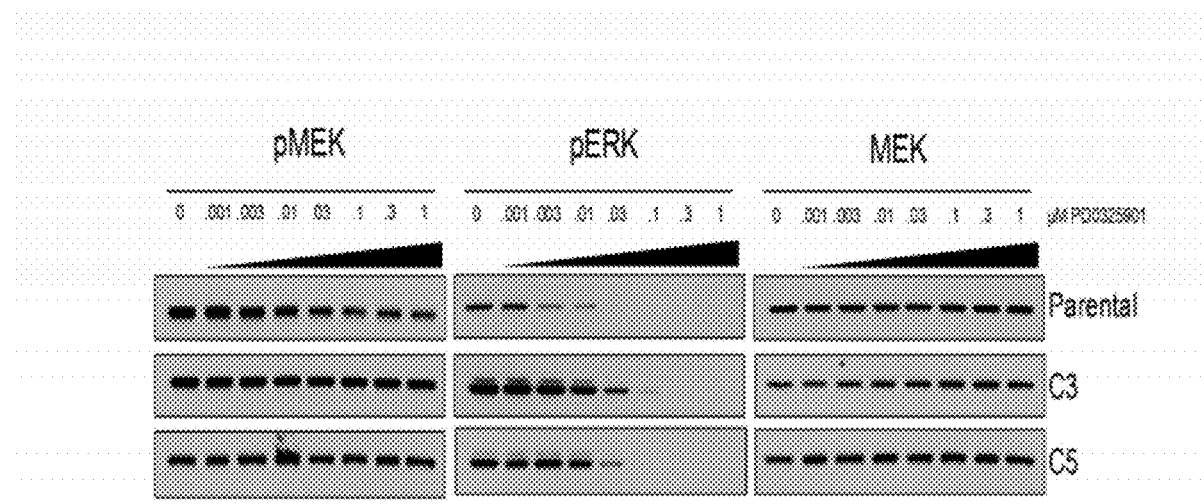

FIGS. 6A-6B shows that PLX4032-resistant cells are sensitive to MEK inhibition.

FIG. 6A shows IC50 (nM) curves following treatment of parental SKMEL-239 cells and the five PLX4032-resistant cell lines with the MEK inhibitor PD0325901 for 5 days.

FIG. 6B shows the dose-response of pMEK and pERK inhibition to increasing concentrations of the MEK inhibitor PD0325901 in parental and two representative resistant clones (C3 and C5).

Figure 7A:
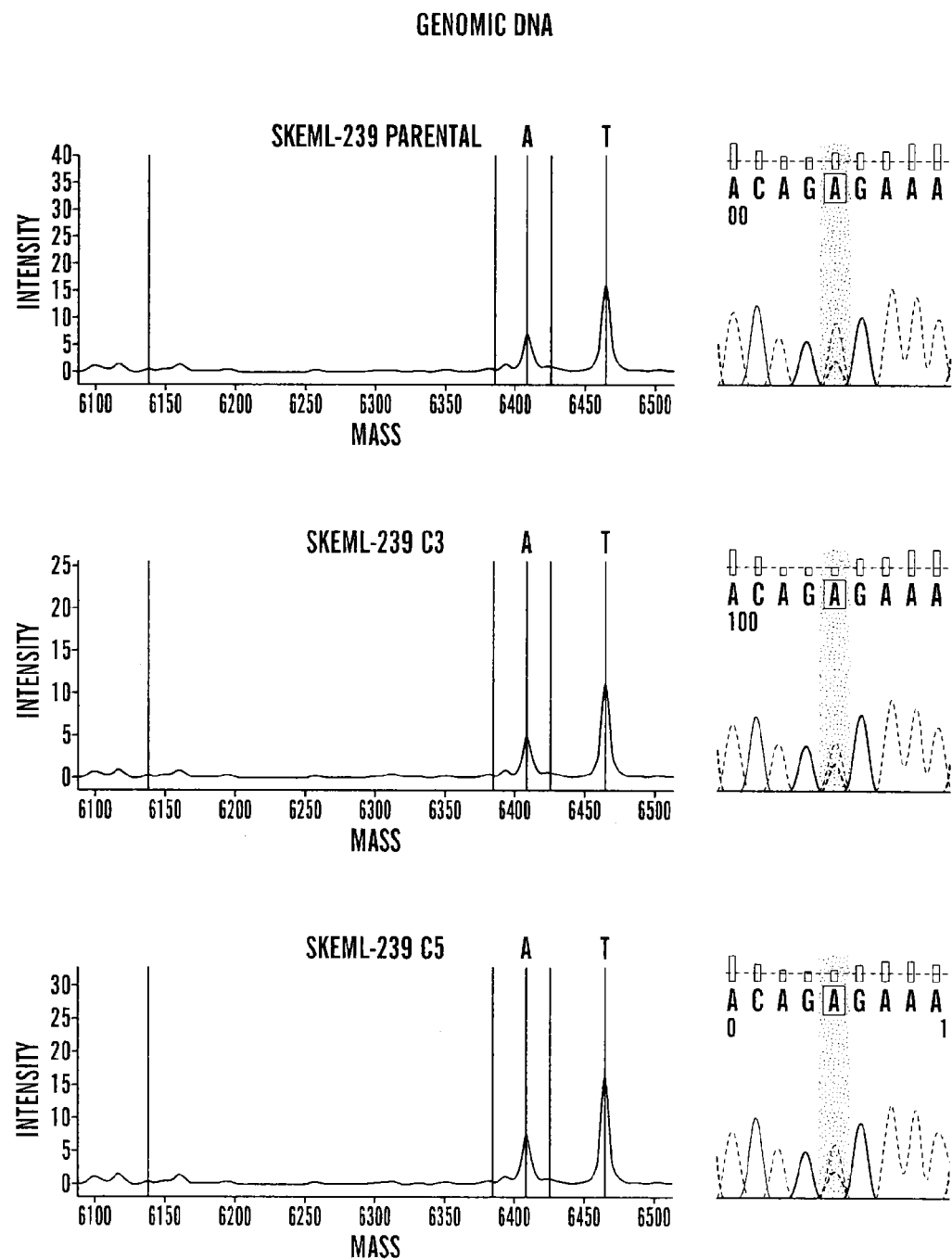
Figure 7B:
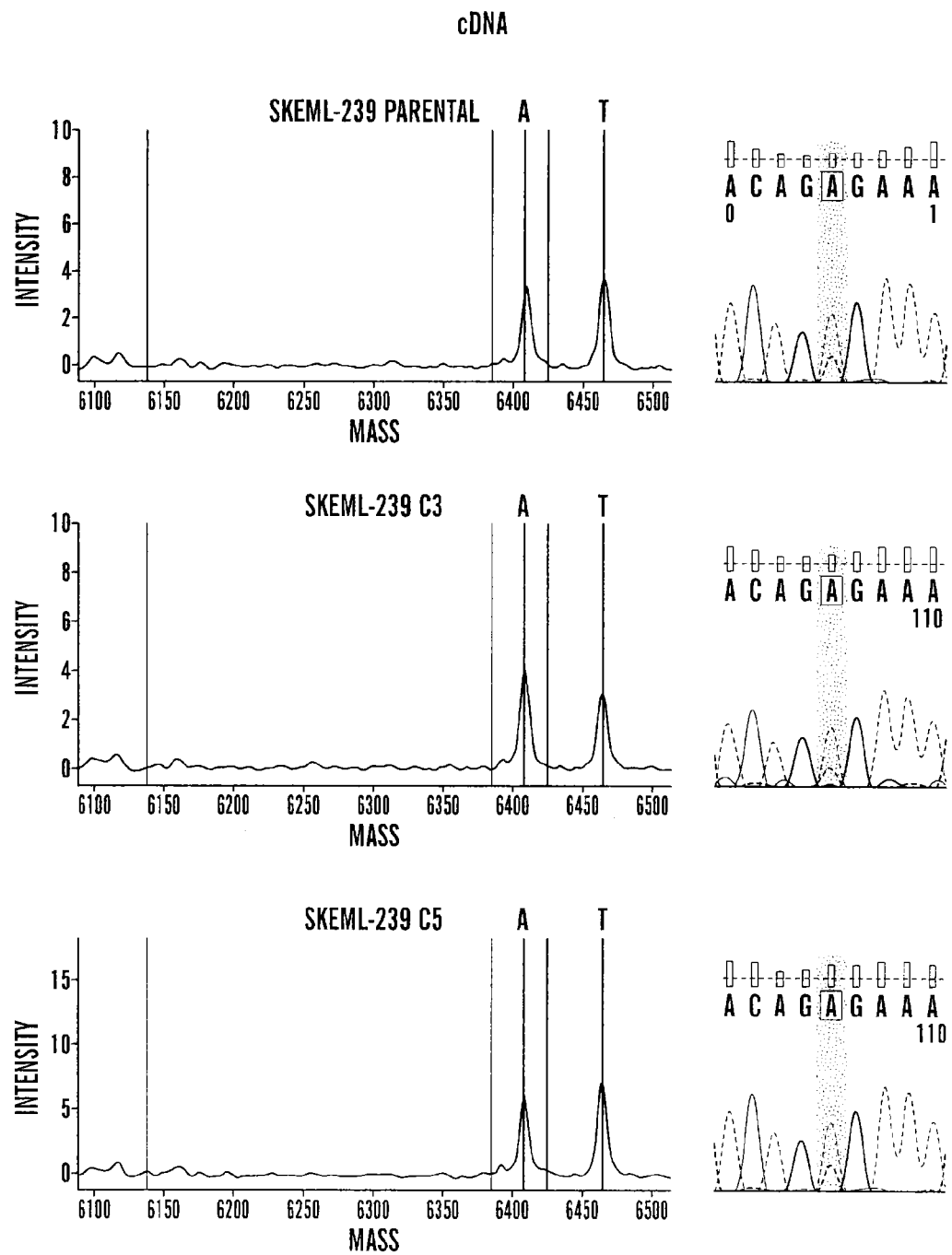

FIG. 7 shows the results of Sanger sequencing and Sequenom traces from genomic DNA (A) and cDNA (B) showing that the parental SKMEL-239 cells and the C3 and C5 clones express the BRAF(V600E) mutant.

Figure 8:
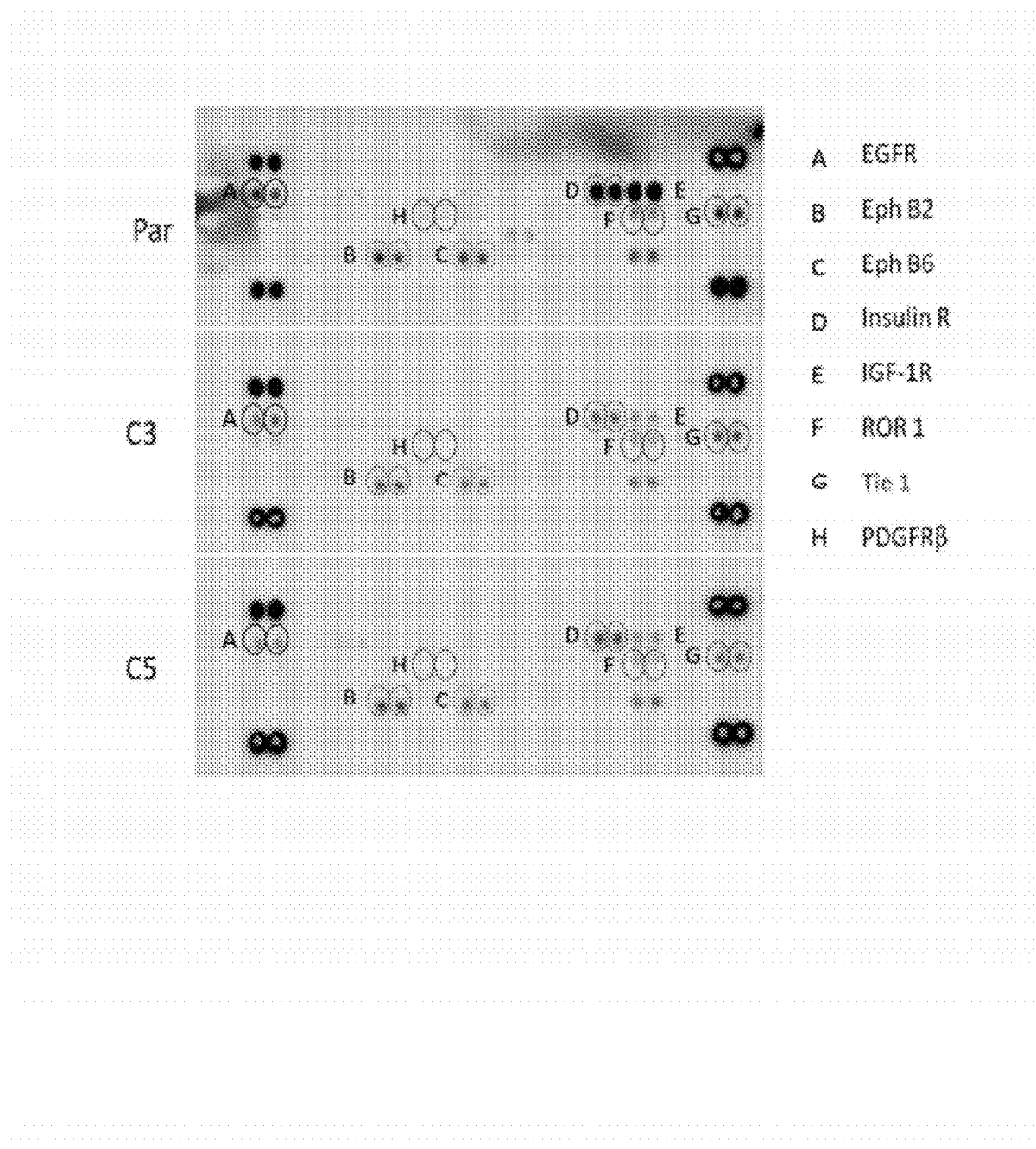

FIG. 8 shows the results from a phospho-tyrosine array showing RTK activity in the parental SKMEL-239 cells and the C3 and C5 resistant clones showing that PLX4032-resistant SKMEL-239 clones maintain a similar global receptor tyrosine kinase ("RTK") activation state as the parental SKMEL-239.

Figure 9:
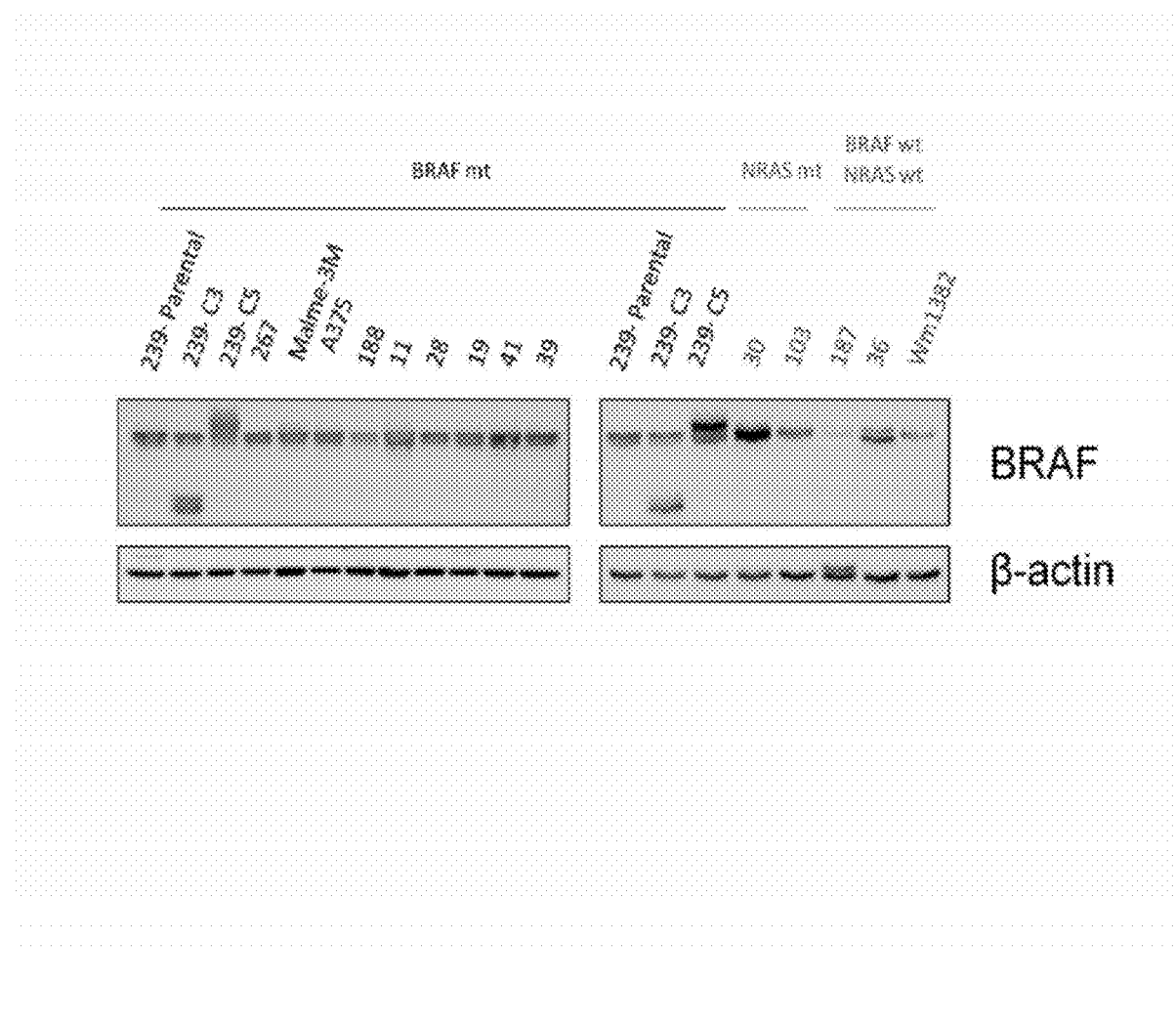

FIG. 9 shows an immunoblot for BRAF using an N-terminal directed antibody showing p61BRAF(V600E) in the C3 clones but not in a panel of 15 PLX4032 treatment naïve melanoma cell lines. The BRAF and NRAS status of the cell lines is as indicated, showing that p61 BRAF(V600E) is not detected by western blot in a panel of PLX4032 treatment-naïve melanoma cell lines.

Figure 10:
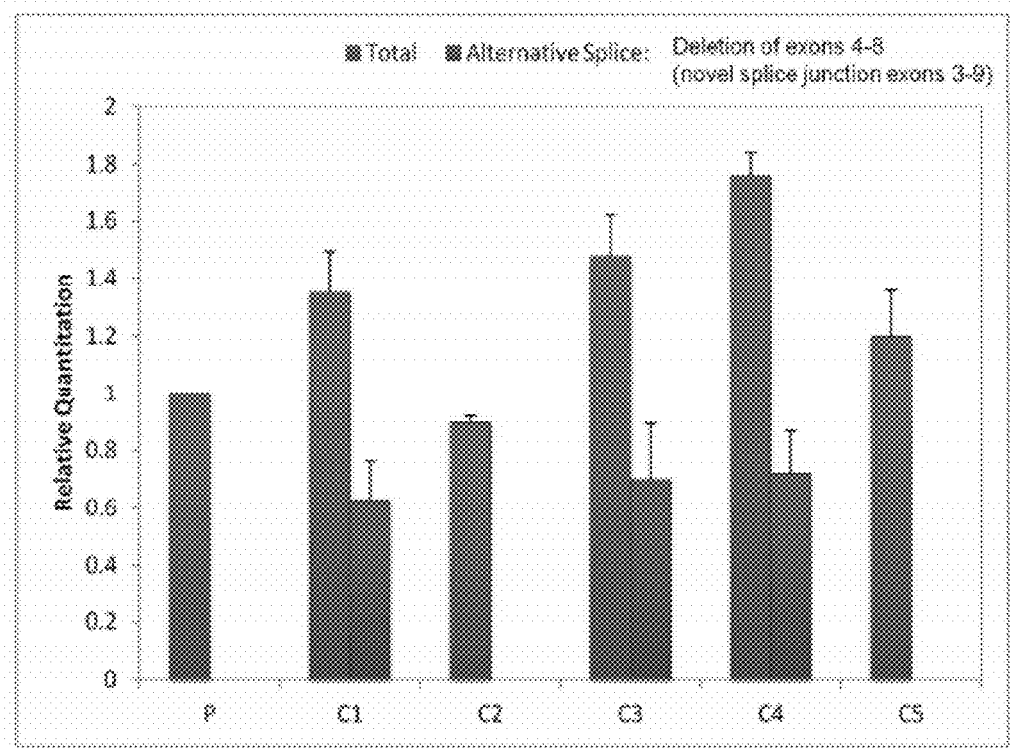

FIG. 10 shows the quantitation of the transcript encoding p61 BRAF(V600E) in the parental and PLX4032-resistant clones.

RNA was extracted from the indicated cell lines and qPCR was carried out on reverse transcription products (cDNA). The PCR primers of the present invention were used to measure total BRAF [SEQ ID NOS 10 and 11] and p61BRAF(V600E) [SEQ ID NOS 6 and 5]. Relative quantification is shown as fold-change of signal compared to the total amount of BRAF in the SKMEL-239 parental cell line. The amount of p61 BRAF(V600E) in the parental, C2 and C5 cell lines, was below the lower limit of detection. The plot represents the mean of three independent experiments and error bars represent standard deviation.

Figure 11A:
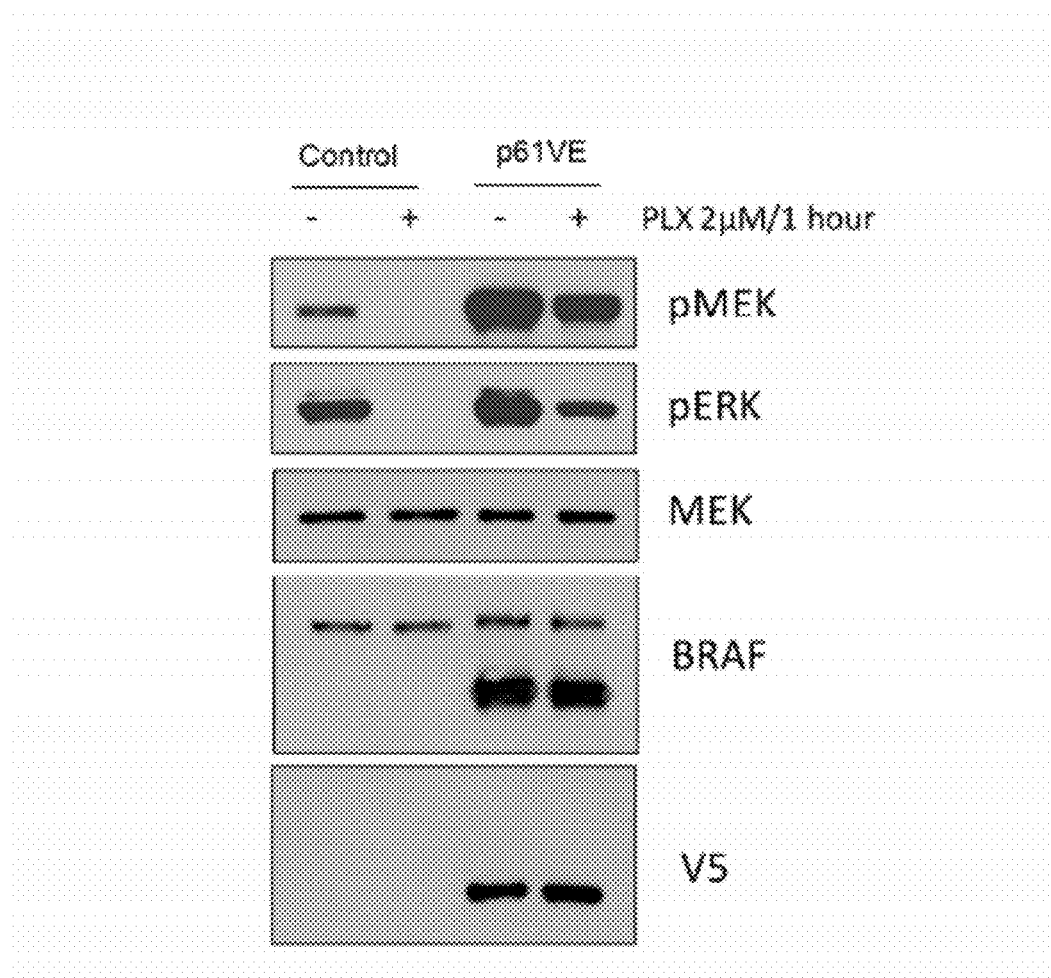
Figure 11B:
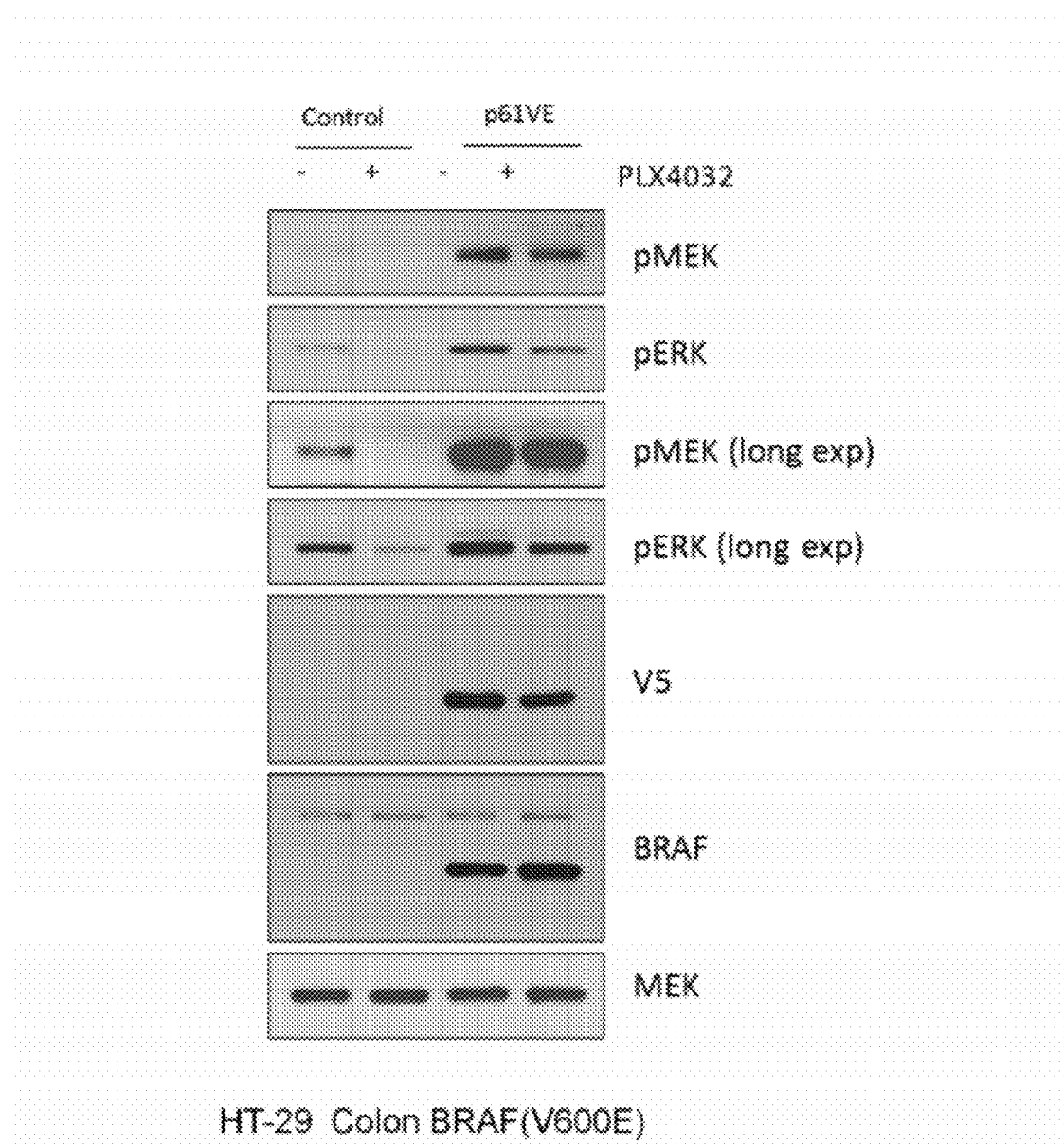

FIG. 11A-11B show that ectopic expression of p61BRAF (V600E) in melanoma and colon cancer cell lines results in resistance to PLX4032.

FIG. 11A shows ectopic expression of p61 BRAF(V600E) in parental SKMEL-239 cells which endogenously expresses BRAF(V600E) and analysis of the effects of PLX4032 on inhibition of ERK signaling at 1 hour post PLX4032 treatment.

FIG. 11B shows ectopic expression of p61 BRAF(V600E) in HT-29 colon cancer cell line which endogenously expresses BRAF(V600E) and analysis of the effects of PLX4032 on inhibition of ERK signaling at 1 hour post PLX4032 treatment.

Figure 12:
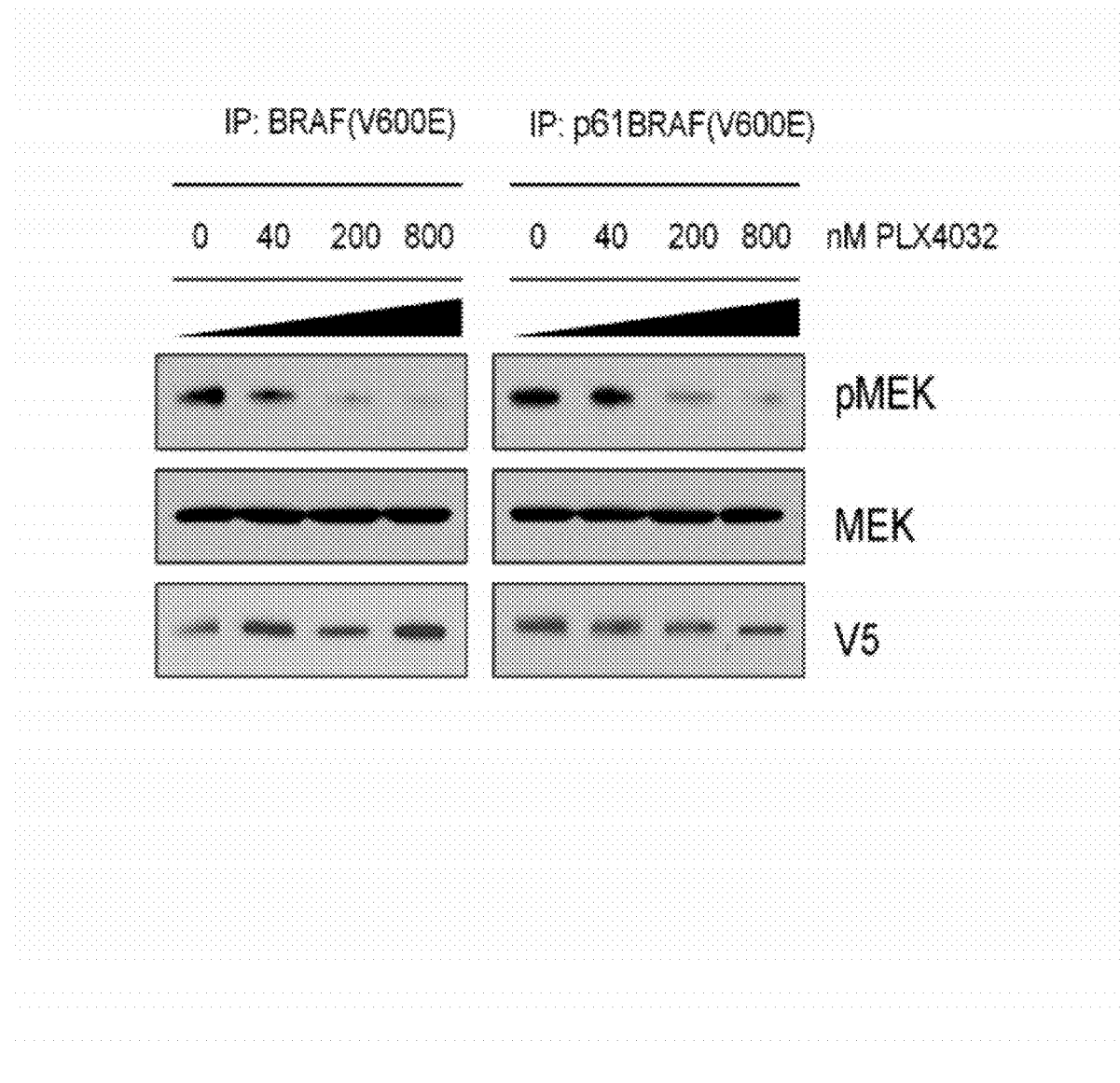

FIG. 12 shows that p61 BRAF(V600E) kinase activity can be inhibited in vitro by PLX4032 indicating p61 BRAF (V600E) is capable of binding PLX4032.

V5-tagged full length BRAF(V600E) or V5-tagged p61 BRAF(V600E) were ectopically expressed in 293H cells. 24 hours later, cells were harvested, lysed and BRAF was immunoprecipitated using a V5 antibody. Immunocomplexes were subjected to a kinase assay in the presence of the indicated concentrations of PLX4032 with recombinant inactive MEK (K97R) as substrate. Kinase activity was estimated by western blot for pMEK.

Figure 13:
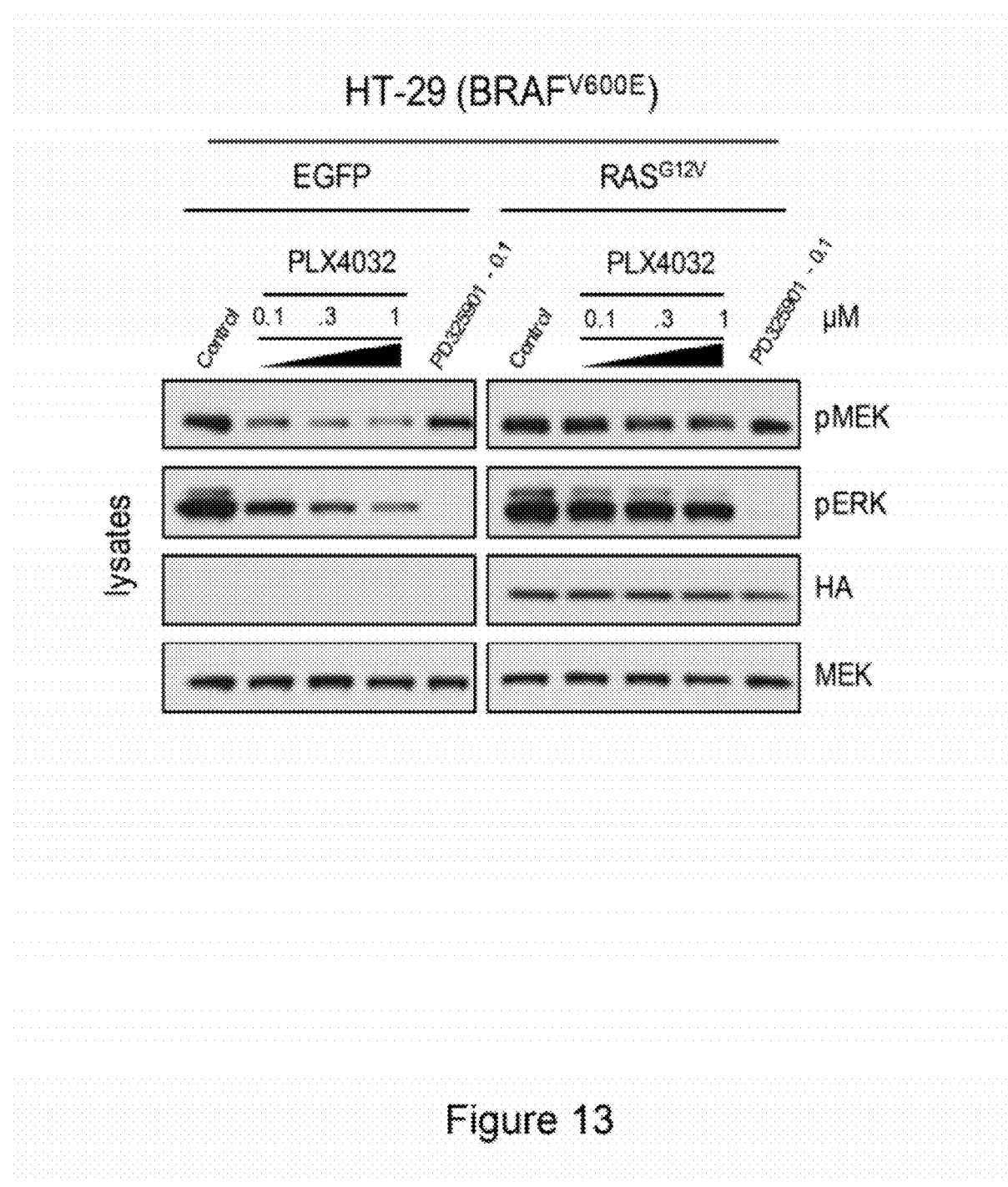

FIG. 13 shows the results of transfection of HT-29 cells (colorectal; BRAF(V600E)) with EGFP or HA-tagged NRAS(G12V) and subsequent treatment with PLX4032 at various concentrations for 1 h. The results indicate that expression of active RAS in BRAF(V600E) expressing cells renders MEK/ERK insensitive to RAF inhibitor.

Figure 14:
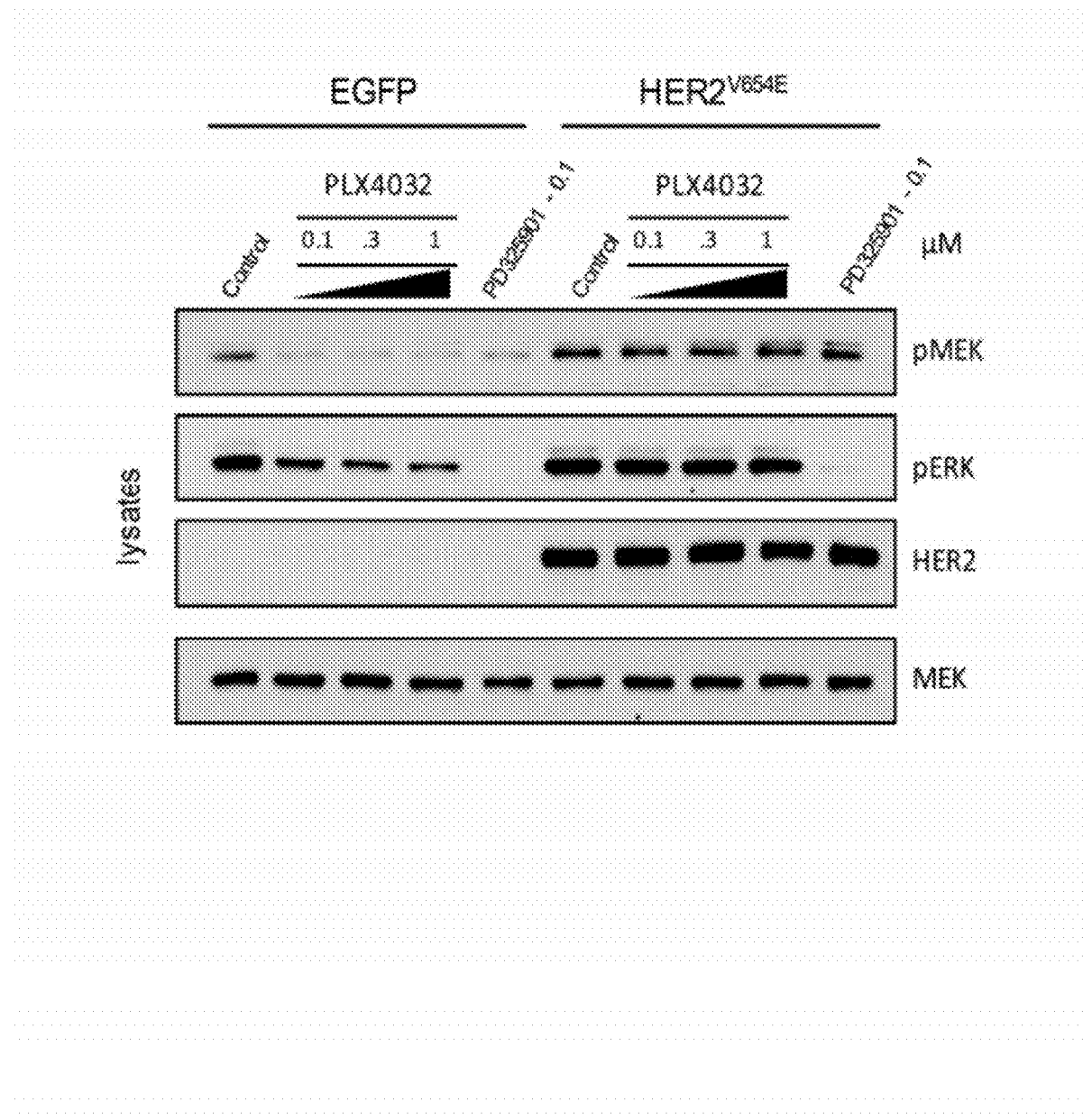

FIG. 14 shows the results of transfection of HT-29 cells (colorectal; BRAF(V600E)) with EGFP or mutationally activated HER2 (V654E) and subsequent treatment with PLX4032 at various concentrations for 1 h. The results indicate that expression of active HER2 in BRAF(V600E) expressing cells renders MEK/ERK insensitive to RAF inhibitor.

Figure 15:
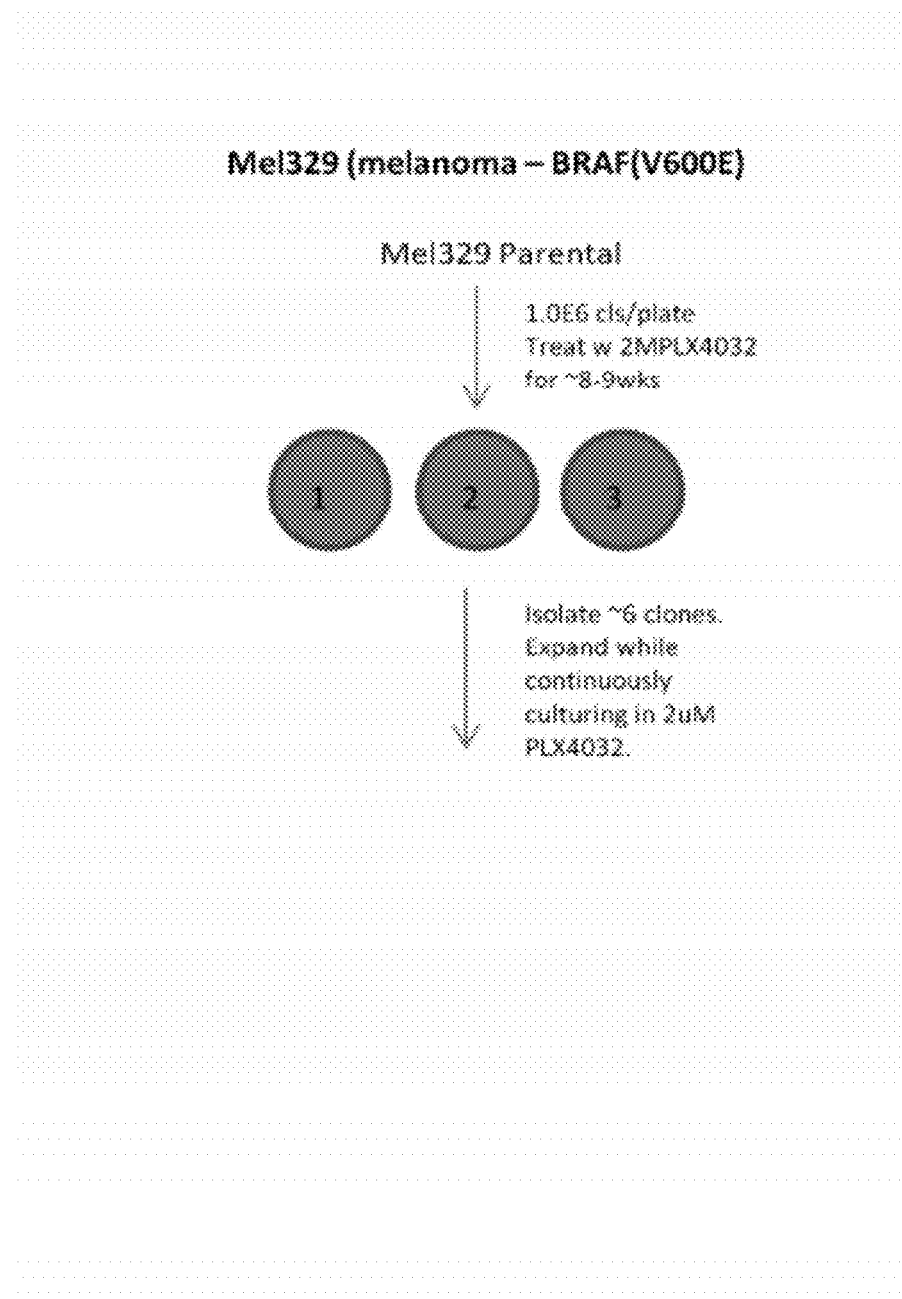

FIG. 15 is a schematic showing the strategy employed to identify new mechanisms of resistance to vemurafenib. Cell lines resistant to the drug were generated by exposing the BRAF-mutant (V600E) melanoma cell line SKMEL-239 to a high dose of vemurafenib (2 µM). After approximately 2 months of continuous drug exposure, vemurafenib-resistant cell populations were isolated and propagated for further analysis.

Figure 16:
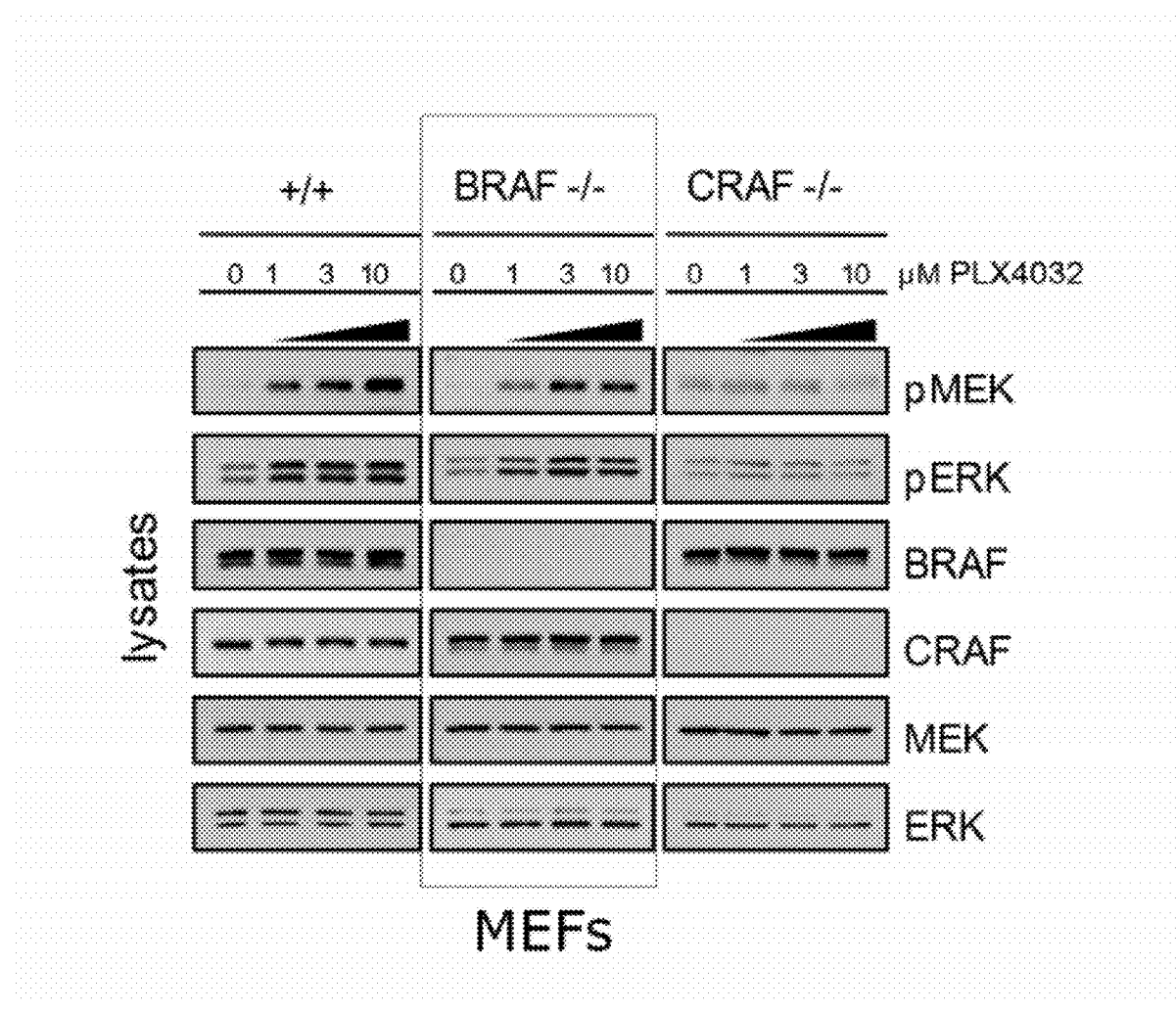

FIG. 16 shows the results of wild-type (+/+), BRAF knockout (BRAF−/−) or CRAF knockout (CRAF−/−) MEFs treated with the indicated concentrations of PLX4032 for 1 h. The results indicate that MEK/ERK activation does not require BRAF.

DETAILED DESCRIPTION OF THE INVENTION

All publications, patents and other references cited herein are incorporated by reference in their entirety into the present disclosure.

In practicing the present invention, many conventional techniques in molecular biology are used, which are within the skill of the ordinary artisan. These techniques are described in greater detail in, for example, Molecular Cloning: a Laboratory Manual 3rd edition, J. F. Sambrook and D. W. Russell, ed. Cold Spring Harbor Laboratory Press 2001; "Oligonucleotide Synthesis" (M. J. Gait, ed., 1984); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988). The contents of these references and other references containing standard protocols, widely known to and relied upon by those of skill in the art, including manufacturers' instructions are hereby incorporated by reference as part of the present disclosure.

As used herein, "cancer" refers to cells or tissues that have characteristics such as uncontrolled proliferation, immortality, metastatic potential, increased anti-apoptotic activity, etc. Some non-limiting examples of cancer include melanoma, colon cancer, lung cancer, breast cancer, pancreatic cancer, glioblastoma, sarcoma, leukemia, blood cancers, etc. As used herein, "tumor" refers to a group of cancer cells or tissues within a subject.

As used herein, a "subject" refers to any animal (e.g. a mammal), including, but not limited to, humans, non-human primates, companion animals, rodents, and the like. Typically, the terms "subject" and "patient" are used interchangeably herein, particularly in reference to a human subject.

As used herein, "response" refers to the outcome when a cell or subject is contacted with an agent (e.g. the cell or subject responds to such agent). A response can be favorable (e.g. desired) or unfavorable (e.g. undesired). By way of non-limiting example, a favorable response can be inhibition of cell growth when a cell is contacted with a particular agent and an unfavorable response can be the accelerated growth of a tumor when a patient with a tumor is contacted with a particular agent.

As used herein, "agent" refers to a substance that elicits a response from a cell or subject when said cell or subject is contacted with an agent. An agent can be a small molecule, a peptide, an antibody, a natural product, a nucleic acid, a chemical, etc. In some cases, an agent can be a composition used in the treatment of, or used to treat, a subject. An "inhibitor" is an agent that interferes with the normal function of a polypeptide, cell, subject, etc.

As used herein, "inhibition" or "to inhibit" means to reduce a function of a polypeptide, cell or subject in response to an agent (e.g. an inhibitor) relative to such function of said polypeptide, cell or subject in the absence of such agent.

As used herein, "treatment" or to "treat" means to address a disease in a subject and includes preventing the disease, delaying the onset of disease, delaying the progression of the disease, eradicating the disease (e.g. causing regression of the disease), etc.

As used herein, "resistance" refers to a lack of response of a cell to an agent to which the cell used to respond (e.g. the cell is "resistant to" such agent). In the context of a patient, "resistance" refers to lack of response of a patient to an agent to which said patient used to respond. Resistance can be acquired (e.g. develops over time) or inherent or de novo (e.g. a cell or subject never responds to an agent to which other similar cells or subjects would respond). By way of non-limiting example, a subject is said to be resistant to treatment when such subject no longer responds to such treatment (e.g. the initial treatment of a subject with an agent results in delay of disease progression, but then such disease progresses even if said subject is still treated with such agent, the subject therefore becomes resistant, or develops resistance to, to said agent, etc.)

As used herein, "nucleotide" refers to a nucleoside (e.g. a monosaccharide linked in glycosidic linkage to a purine (adenine (A) or guanine (G)) or pyrimidine (thymine (T), cytosine (C) or uracil (U)) base with at least one phosphate group linked, typically at a 3' or a 5' position (for pentoses) of the saccharide, but can be at alternative positions of the saccharide. The naturally occurring nucleotides are A, G, T, C, and U, but non-natural, artificial, and modified nucleotides are known in the art. A nucleotide can also be referred to as a "base" or "base pair".

As used herein, "polynucleotide" refers to a molecule comprised of multiple nucleotides linked in sequential fashion. A modification or derivative of naturally occurring nucleotides may occur at any sequential position in an oligonucleotide or a polynucleotide. The order in which the nucleotides are linked is typically referred to as the "nucleic acid sequence" or "DNA sequence" or "RNA sequence." Polynucleotides can be any number of nucleotides in length (e.g. anywhere from ~20 nucleotides to tens of thousands of nucleotides or more). Polynucleotides of shorter length (e.g. ~10-50 nucleotides) are typically referred to as "oligonucleotides" or "oligos."

As used herein, "gene" refers to a polynucleotide nucleic acid sequence (e.g. DNA) that comprises coding sequences necessary for the production of a polypeptide or precursor including both the full length coding sequence as well as any portion(s) of the coding sequence sufficient to produce a polypeptide, or portions thereof, with at least a portion of the functional property(ies) of the full length polypeptide. A "gene" can further include the nucleotide sequences that are upstream (e.g. 5') or downstream (e.g. 3') to the coding sequences. Such upstream and downstream sequences generally contain regulatory elements necessary for the transcription of the gene and subsequent translation of the mRNA polynucleotide and generally do not contain sequences which are translated and included in a polypeptide or precursor. Such sequences are generally referred to as the "untranslated region" or "UTR." A "gene" can encompass both the cDNA and genomic forms of a gene. The genomic form of a gene contains the coding regions of the gene (e.g. as used herein an "exon") interrupted with non-coding regions commonly referred to as introns, intervening regions, or intervening sequences (as used herein "intron"). Exons are typically numbered sequentially from the 5' end of a gene. Introns are typically removed from the nuclear or primary transcript by a mechanism called "splicing" and are absent in the messenger RNA (mRNA) transcript that is translated into the functional polypeptide. As used herein a "splice junction" refers to the boundary between two exons following the removal of intron(s) by splicing. Typical splicing of a gene will create splice junctions between sequential exons of a gene (e.g. splice junctions between exon 1 and exon 2, exon 2 and exon 3, exon 3 and exon 4, . . . etc.). In some cases, splicing will create splice junctions between non-sequential exons of a gene (e.g. splice junctions between exon 1 and exon 5, exon 5 and exon 10, etc) resulting in removal, or deletion, from the resulting mRNA of both the non-coding introns and coding exons, or portions thereof, that are located between the two exons that flank the splice junction (e.g. removal of exons 2, 3, and 4 or exons 6, 7, 8, and 9, of the above example). This process is typically referred to as "alternative splicing" with the resulting mRNA being referred to as an "alternative splice variant" or "splice variant." The polypeptide translated from such alternatively spliced mRNA may also be referred to as a "splice variant" or simply "variant." See FIG. 2A for a schematic representation of both typical splicing and alternative splicing of the BRAF mRNA. Alternative splicing can produce an in-frame mRNA splice variant, meaning translation of the mRNA results in a stable polypeptide with functionality; the functionality of such resulting polypeptide may or may not be different than that of a polypeptide translated from the normally spliced mRNA. However, alternative splicing can also produce an out-of-frame mRNA splice variant, meaning translation of the mRNA results in a truncated unstable polypeptide. Alternative splicing can occur under normal physiological conditions or aberrant conditions. The novel 5' splice variants of the present invention include any BRAF mRNA that has deletion of at least one exon, at least two exons, at least three exons, at least four exons, at least five exons, at least six exons, at least seven exons, at least eight exons, at least nine exons, or at least 10 exons, of any of the exons between exon 1 and the exon(s) coding the catalytic domain of BRAF mRNA (~exon 11), whereby the BRAF polypeptide translated from such 5' splice variant has increased ability to form RAS-independent dimers and becomes resistant to BRAF and/or pan-RAF inhibitors. Such splice variants can also include deletion of exon 1. In one embodiment of the present invention, said novel 5' splice variant comprises deletions of exons 4-10 of BRAF mRNA. In another embodiment of the present invention, said novel 5' splice variant comprises deletions of exons 4-8 of BRAF mRNA. In yet another embodiment of the present invention, said novel splice variant comprises deletions of exons 2-8 of BRAF mRNA. Alterations to a gene, cDNA, mRNA, RNA, etc are herein referred to as "genetic alterations"

As used herein, the term "polymerase chain reaction" ("PCR") refers to the methods described in U.S. Pat. Nos. 4,683,195, 4,683,202, and 4,965,188 which describe a method for increasing the concentration of a segment of a target nucleotide sequence (a "template"). This process for amplifying the template consists of introducing a large excess of two oligonucleotide primers (a "PCR primer pair") to the DNA mixture containing the desired template, followed by a precise sequence of thermal cycling in the presence of a DNA polymerase. The two primers of the PCR primer pair are complementary to their respective strands of the double stranded template. The mixture is denatured and the primers then annealed to their complementary sequences within the template. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence (an "amplicon" or "PCR product" or "amplification product"). The cycling conditions are dependent on the template sequence and the primer design. Standard cycling conditions are known in the art and can be optimized by one skilled in the art. The length of the amplicon of the template is determined by the relative positions of the two primers of the PCR primer pair with respect to each other, and therefore, this length is a controllable parameter. In addition to genomic DNA, any oligonucleotide or polynucleotide sequence (e.g. cDNA etc.) can be amplified with the appropriate PCR primer pairs.

As used herein, the term "primer" or "PCR primer" refers to an oligonucleotide that is complementary to a particular nucleic acid sequence of a template and is capable of acting as a point of initiation of extension with a polymerase under suitable PCR conditions and when used in suitable PCR primer pairs, will produce an amplicon of the target. The primer is preferably single stranded but can also be double stranded. If double stranded, the primer is first treated to separate its strands before being used to prepare extension products. Preferably, the primer is an oligodeoxyribonucleotide. The exact number of nucleotides in the primers will depend on many factors, including temperature, source of primer and the use of the method. The PCR primers of the present invention have about 20 nucleotides but can contain more or less. In addition, the PCR primers of the present invention can have any number of nucleotides substituted from those listed in SEQ ID NOS 2-11 including 1 nucleotide substituted, 2 nucleotides substituted, 3 nucleotides substituted, 4 nucleotides substituted, 5 nucleotides substituted, etc. up to 50% (or more) of the original nucleotide sequence listed in SEQ ID NOS 2-11 as long as such substituted PCR primer provides the desired amplicon under suitable PCR conditions. Methods for the design and synthesis of PCR primers are readily known in the art and any such method of synthesis is sufficient for production of the PCR primer(s) of the present invention.

As used herein, the terms "reverse-transcriptase" and "RT-PCR" refer to a type of PCR where the starting material is mRNA. The starting mRNA is enzymatically converted to complementary DNA or "cDNA" using a reverse transcriptase enzyme. The cDNA is then used as a template for a PCR reaction.

As used herein, the term "real-time PCR" or "quantitative PCR" or "qPCR" refers to measuring changes in mRNA for determination of levels of specific DNA or RNA sequences in tissue samples. It is based on detection of a fluorescent signal produced proportionally during amplification of a PCR product.

As used herein, "complement" and "complementary" refers to two sequences whose bases form complementary base pairs, base by base. By way of non-limiting example, for naturally occurring bases, adenine (A) is complementary to thymine (T) and uridine (U) whereas guanine (G) is complementary to cytosine (C). Two nucleotides that are complementary to each other will "hybridize" or "anneal" to each other under suitable conditions.

As used herein, "sequencing" or "sequence analysis" refers to the determination of the nucleotide sequence of a polynucleotide fragment. Multiple methods of sequencing are readily known to those in the art and include, without limitation, chain terminator sequencing methodologies such as Sanger sequencing as well as paired end sequencing methodologies such as Illumina, SOLiD or other next generation sequencing methodologies under development. In one embodiment of the present invention, sequencing is performed using the Sanger method.

As used herein, "detection" or "detecting" etc. refers to measuring the presence of one or more of the novel 5' splice variant(s) of the present invention. Multiple methods of detection are readily known to those in the art and can be used to measure the presence of the novel 5' splice variant(s) of the present invention and include, without limitation, PCR, sequencing, Northern blotting, 5' RACE, immunohistochemistry, Western blot, etc. In one embodiment of the present invention, PCR is used to detect such novel 5' splice variant(s) using the PCR primer(s) described herein. In another embodiment, PCR is used to detect such novel 5' splice variant(s) using the PCR primer pair wherein the first primer of said PCR primer pair binds to a region surrounding and including the novel splice junction of said novel 5' splice variant, or portions thereof, and the second primer of said PCR primer pair binds any region on the opposite strand to which said first primer binds whereby said PCR primer pair is effective to provide an amplicon that includes said novel splice junction and wherein said PCR primer pair fails to provide an amplicon that lacks said novel splice junction; such novel splice junction being 5' to exon(s) that encode the catalytic domain of BRAF.

As used herein, "sample" refers to a subject, cell, or tissue and is meant to include a specimen or culture obtained from any source, in particular as a biological sample. Biological samples may be obtained from subjects (including humans) and encompass fluids, solids, gases, tissues, cells, and bones. Such biological samples can be obtained by methods readily known in the art including, without limitation, biopsy, surgery, etc. In one embodiment of the present invention, such sample is obtained from a subject by biopsy of a subject's tumor.

As used herein, "kit" refers to a diagnostic kit useful for detecting the novel 5' splice variant(s) of the present invention in a human subject. In one embodiment, such kit comprises vessel(s) containing the compositions necessary to practice the methods of the present invention and include at least one PCR primer pair useful for the detection of such novel 5' splice variants and a carrier to compartmentalize such vessels. Such embodiment further includes a positive control comprising a polynucleotide sequence of BRAF containing the novel 5' splice variant detected by said PCR primer pair and a negative control comprising a polynucleotide sequence of BRAF that does not contain said novel 5' splice variant detected by said PCR primer pair. Such embodiment further includes reagents necessary for PCR analysis. Such embodiment further includes instructions. As used herein "kit" also refers to a screening kit useful for identifying agents useful in the treatment of cells and/or subjects resistant to treatment with BRAF and/or pan-RAF inhibitors as well as agents useful for disrupting RAS-independent BRAF dimers.

RAF inhibitors have remarkable clinical activity in mutant BRAF melanomas but that activity is limited by acquisition of resistance to the drugs.

Identification of Splice Variants of BRAF(V600E)

BRAF mRNA is comprised of 18 exons and the starting and ending nucleotides of each exon, using the sequence numbering of Genebank accession number NM_004333, are described in Table 1. The regulatory domains of BRAF are located in the more 5' exons, or portions thereof, (e.g. exons ~1-10) while the catalytic and kinase domains are located in the more 3' exons, or portions thereof, (e.g. exons ~11-18).

TABLE 1

Starting and ending nucleotide of exons of BRAF

| Exon Number | Start Nucleotide-End Nucleotide |
|---|---|
| 1 | 1-199 |
| 2 | 200-301 |
| 3 | 302-565 |
| 4 | 566-669 |
| 5 | 670-772 |
| 6 | 773-921 |
| 7 | 922-1041 |
| 8 | 1042-1201 |
| 9 | 1202-1238 |
| 10 | 1239-1375 |
| 11 | 1376-1493 |
| 12 | 1494-1578 |
| 13 | 1579-1755 |
| 14 | 1756-1802 |
| 15 | 1803-1921 |
| 16 | 1922-2053 |
| 17 | 2054-2088 |
| 18 | 2189-2947 |

Unique splice variants of BRAF were identified, each of which lacked exons, or portions thereof, of the regulatory domain(s) of BRAF which lie 5' to the catalytic kinase domain: e.g., deletion of exons 4-10, deletion of exons 4-8, and deletion of exons 2-8 etc. The present disclosure results from the observation that patients with tumors that express one of these BRAF splice variant(s) are resistant to therapeutic intervention with BRAF and/or pan-RAF inhibitors. That is, patients with tumors that express a variant form of BRAF containing a deletion of any exon(s), or portions thereof, within the 5' regulatory domain(s) of BRAF, which increase RAS-independent dimerization of BRAF, will be resistant, or develop resistance, to therapeutic intervention with BRAF and/or pan-RAF inhibitors. The identification of these splice variants, therefore, provides, among other things, a method to monitor a patient who is undergoing treatment with a BRAF inhibitor for the development of resistance to the inhibitor by assaying a tumor cell from the patient to detect the presence of a BRAF splice variant described herein.

The present invention further describes compositions and methods to identify novel agents that are useful to overcome resistance to therapeutic intervention with BRAF and/or pan-RAF inhibitors using cell lines that, endogenously or ectopically, express the novel 5' BRAF splice variants described herein and/or isolated polynucleotides of the novel 5' BRAF splice variants described (and proteins translated therefrom).

Detection of BRAF Splice Variants

Figure 2A:
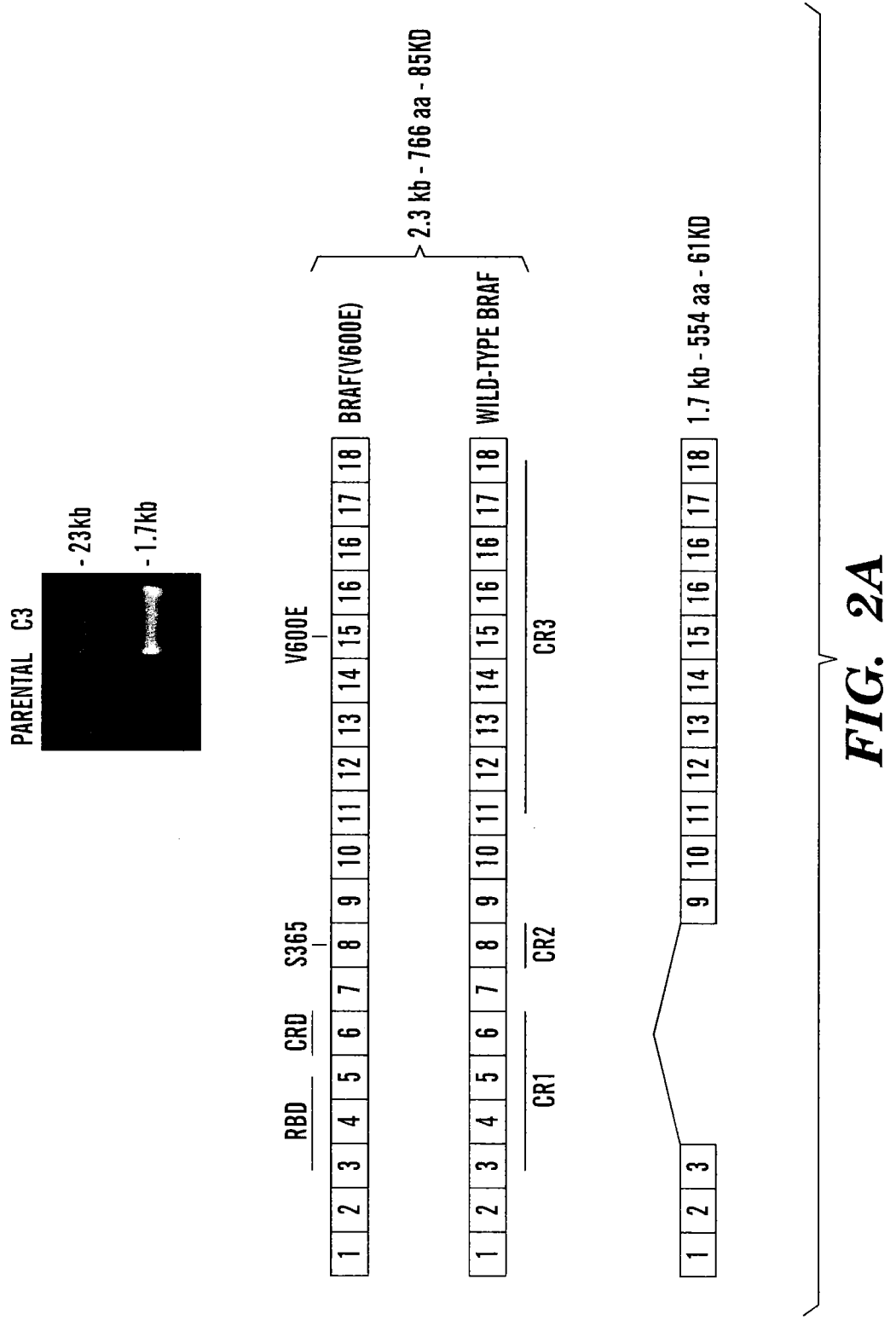
FIGS. 2A-2E shows a newly identified BRAF(V600E) variant that lacks exons 4-8 and is resistant to the RAF inhibitor PLX4032.

The splice variants identified herein are the result of a deletion of 5' exons, or portions thereof, of the regulatory domain of BRAF including those exons, or portions thereof, encoding conserved region 1 (as used herein "CR1") and conserved region 2 (as used herein "CR2") of BRAF, which include domains critical for BRAF activation, most notably, the RAS-binding domain (as used herein "RBD") and the cysteine-rich domain (as used herein "CRD") (FIG. 2A).

Figure 3A:
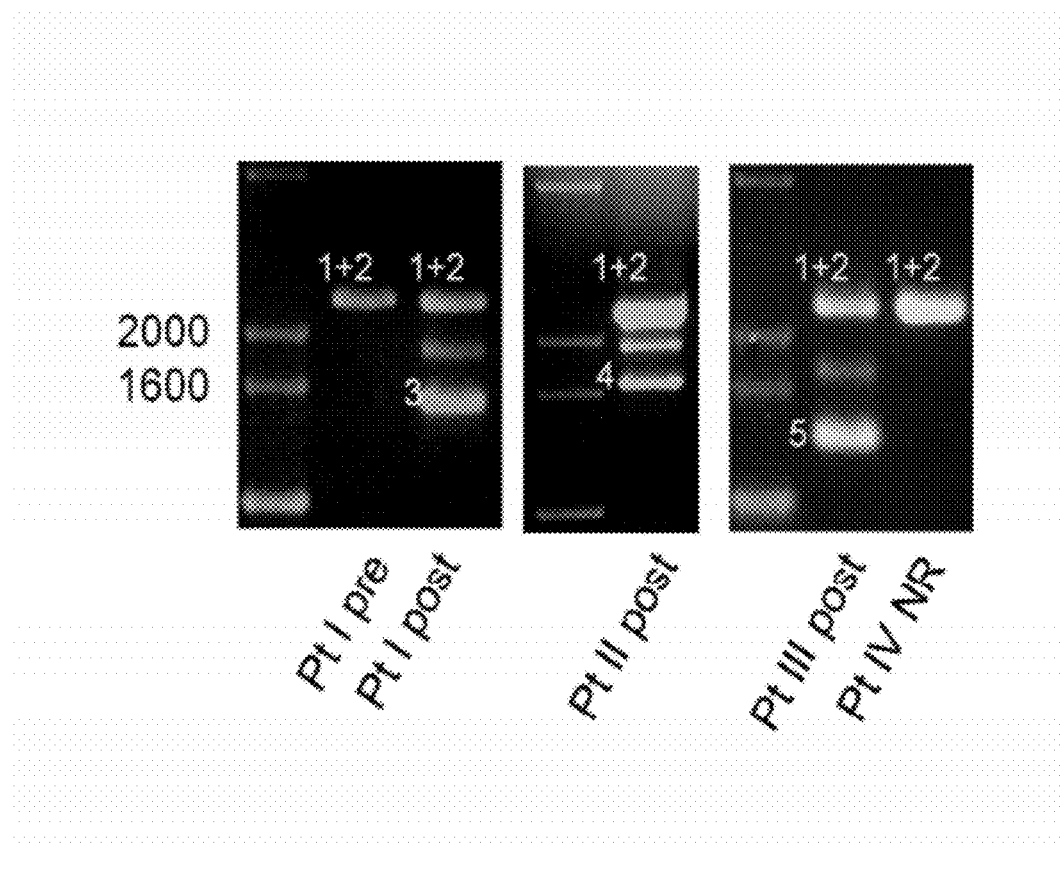
FIGS. 3A-3C illustrates the identification of novel splice variants of BRAF(V600E) in human tumors resistant to PLX4032.
Figure 3B:
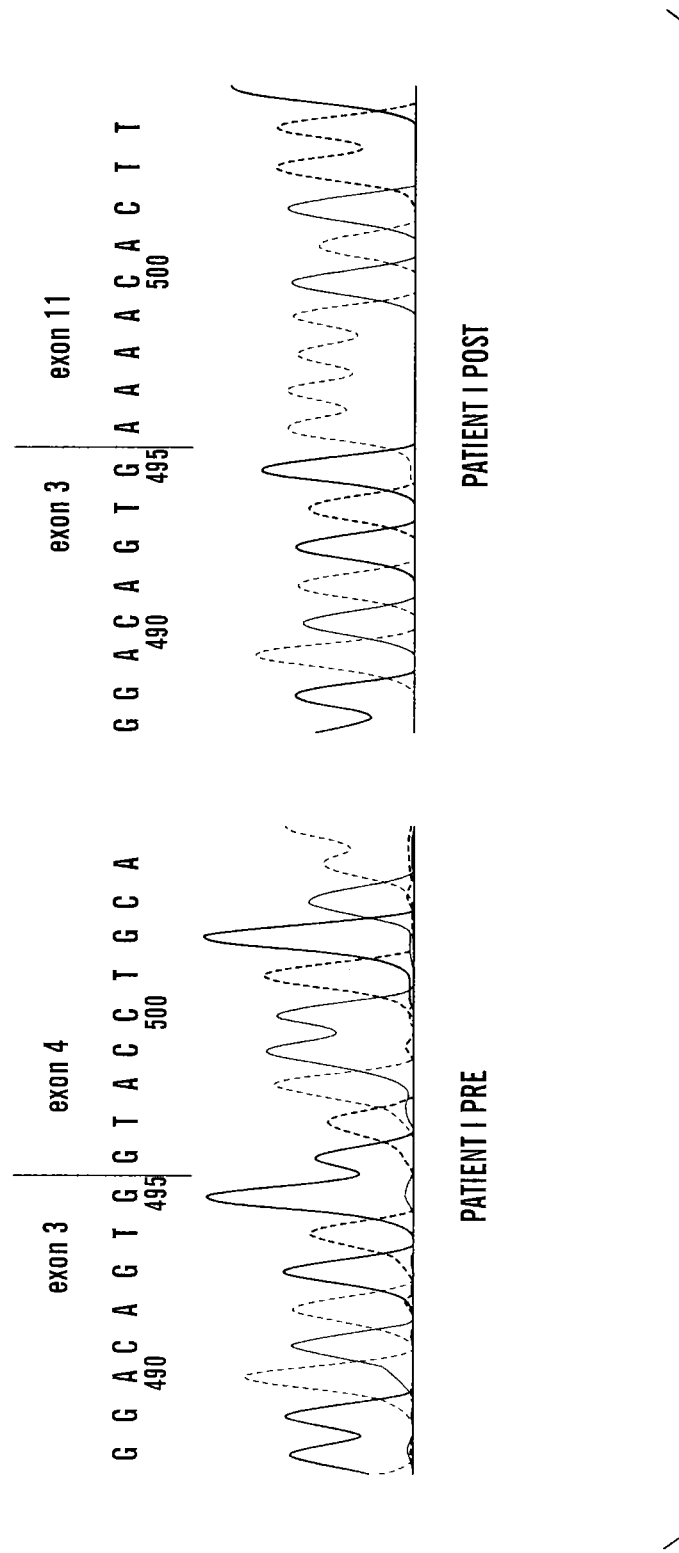
Figure 3C:
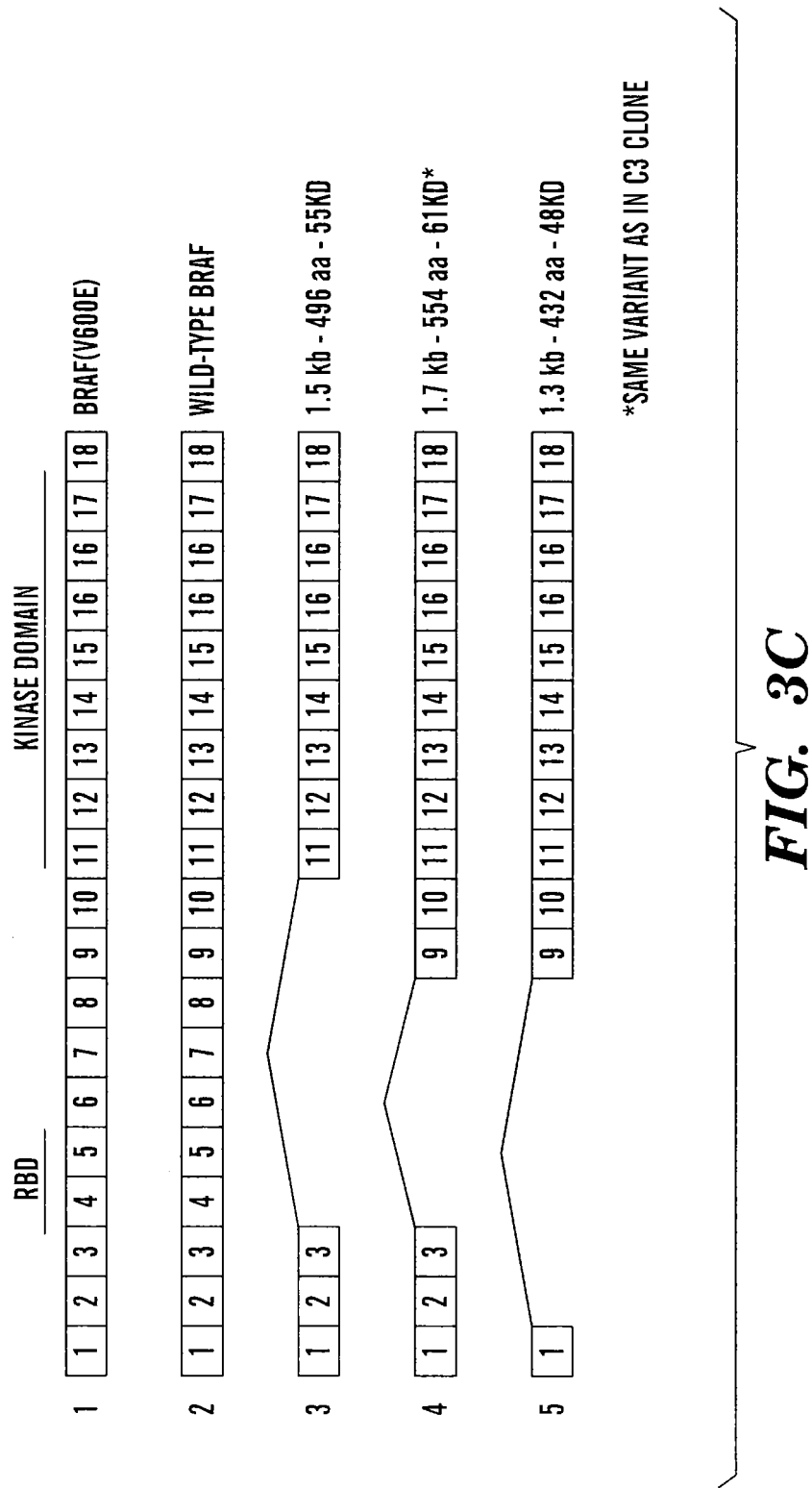

In FIG. 3C, each novel splice variant is shown as a schematic denoting the missing exons. In one BRAF variant (as used herein "BRAF 3_11"), deletion of exons 4-10 gives rise to a new splice junction which has the nucleotide sequence of SEQ ID NO: 7. The full nucleotide sequence for a cDNA generated by the deletion of exons 4-10 is given in SEQ ID NO: 13. Similarly, BRAF variant "BRAF 3_9" is generated by the deletion of exons 4-8. The full length cDNA for BRAF 3_9 is set forth as SEQ ID NO: 15 and the splice junction encompasses SEQ ID NO: 6. The full length sequence for another BRAF variant, "BRAF 1_9," the result of the deletion of exons 2-8, is shown by SEQ ID NO: 14 having a new 1-9 splice junction which encompasses SEQ ID NO: 4.

The resulting in-frame mRNA transcript for the splice variants, when translated, produces truncated BRAF protein monomers which form constitutively active dimers (i.e. RAS-independent dimerization) which drive downstream signaling, promote cancer progression and cause resistance to treatment with BRAF and/or pan-RAF inhibitors.

The availability of a method for detection of these splice variants provides a unique opportunity to identify tumor cells that are likely to be or become resistant to BRAF inhibitors.

Clinical Application

The use of the methods of the present invention to detect BRAF splice variants in patients permits the identification of patients likely to be resistant or become resistant to BRAF and/or pan-RAF inhibitors so that alternative treatment strategies for such resistant patients can be implemented early on. The present invention further provides compositions and methods to screen for novel agents capable of overcoming resistance to BRAF and/or pan-RAF inhibitors driven by the mechanisms of resistance described herein.

Primers and Probes

A number of methods are currently available in the art, which enable the skilled artisan to detect gene products, both protein and nucleic acid, of the BRAF splice variants disclosed herein. These methods include without limitation, for example, PCR and exon-junction microarray (see e.g. Rahman et al., *Differential detection of alternatively spliced variants of Ciz1 in normal and cancer cells using a custom exon junction microarray*. BMC Cancer 10:482 2010). In one aspect, therefore, the present invention provides polymerase chain reaction (as used herein "PCR") primers capable of detecting the novel 5' BRAF splice variants described herein. Methods for the design of primers and probes for use in PCR and microarray analysis are well known in the art (see e.g., Castle et al., *Optimization of oligonucleotide arrays and RNA amplification protocols for analysis of transcript structure and alternative splicing*. Genome Biology 4:R66 2003).

In one embodiment, the invention includes a synthetic oligonucleotide that hybridizes under stringent conditions to a nucleic acid comprising the nucleotide sequence of BRAF exon 1 (SEQ ID NO: 20).

In one aspect, the present invention provides PCR primers, primer pairs and primer sets that hybridize, under suitable conditions, to a sense or anti-sense strand of a BRAF gene or gene product of a BRAF gene. In one embodiment, the first primer of a PCR primer pair hybridizes at any position (in either coding or untranslated region(s)) 5' in each respective strand to a deletion of exon(s), or portions thereof, of a BRAF gene that encodes CR1 and/or CR2 including domains critical for BRAF activation, such as the RBD and/or the CRD, such exon(s) being 5' to exon(s) which encode the catalytic domain of BRAF. The second PCR primer of a PCR primer pair hybridizes to any region on the opposite strand to which said first primer hybridizes whereby said PCR primer pair is effective to provide an amplicon. General primer structures are provided based on SEQ ID NOS: 2, 9 and 3 and may be longer or shorter than SEQ ID NOS: 2, 9 and 3, for example between 10-30 nucleotides or in some embodiments between 18-21; those of skill in the art will recognize a size that is optimal. Primers may also have a certain number of bases in SEQ ID NOS 2, 9 and 3 substituted to other bases to the extent that such substituted primers are capable of providing an amplicon.

In one embodiment of the present invention, the first primer of a PCR primer pair hybridizes to a polynucleotide containing exon 1 of the BRAF gene and the second primer of the PCR primer pair hybridizes to a polynucleotide that contains exon 11 through exon 18 of a BRAF gene. In another embodiment of the present invention, the first primer of said PCR primer pair hybridizes to a polynucleotide containing the 5' untranslated region ("5' UTR") of a BRAF gene and the second primer of said PCR primer pair hybridizes to a polynucleotide containing exon 18 of a BRAF gene.

Another aspect of the present invention provides a PCR primer pair that hybridizes, under suitable conditions, to a sense or anti-sense strand of a BRAF gene 5' to the novel splice junction of the BRAF splice variants described herein wherein the first primer of said PCR primer pair hybridizes to a region surrounding and including the novel splice junction, or portions thereof, and the second primer of said PCR primer pair hybridizes any region on the opposite strand to which said first primer binds whereby said PCR primer pair is effective to provide an amplicon that includes said novel splice junction and wherein said PCR primer pair fails to provide an amplicon that lacks said novel splice junction; such novel splice junction being 5' to exons(s) which encode for the catalytic domain of BRAF. General primer structures are provided based on SEQ ID NOS 4-8 and may be longer or shorter than SEQ ID NOS 4-8 and may also have a certain number of bases in SEQ ID NOS 4-8 substituted to other bases to the extent that such substituted primers are capable of providing an amplicon if the polynucleotide sequence of a BRAF gene contains a novel splice junction(s) described herein but fails to provide an amplicon if the polynucleotide sequence of a BRAF gene lacks a novel splice junction(s).

In one embodiment of the present invention, the first primer of said PCR primer pair contains ~17 base pairs of the 3' end of the 5' exon and ~3 base pairs of the 5' end of the 3' exon that flank the novel splice junction. In another embodiment of the present invention the first primer of said PCR primer pair is chosen from the group comprising i) a PCR primer containing ~17 base pairs of the 3' end of exon 3 and ~3 base pairs of the 5' end of exon 11; ii) a PCR primer containing ~17 base pairs of the 3' end of exon 3 and ~3 base pairs of the 5' end of exon 9; and iii) a PCR primer containing ~17 base pairs of the 3' end of exon 1 and ~3 base pairs of the 5' end of exon 9. See FIG. 13 for schematic representation of the novel splice junction sequence(s) between the 5' exons and the 3' exons that flank such novel splice junctions along with sequence of exemplary first primer(s) of the PCR primer set described herein. In one embodiment of the present invention, the second primer of said PCR primer set hybridizes to polynucleotide sequence of a BRAF gene ~100-1500 base pairs from the first primer of said PCR primer set. In another embodiment of the present invention, the second primer of said PCR primer set hybridizes to a polynucleotide sequence of a BRAF gene ~100-1500 base pairs from the first primer of said PCR primer set and is 3' relative to said first primer.

A further aspect of the present invention provides a method of detecting the novel 5' BRAF splice variants described herein comprising isolating a sample from a subject having or suspected of having cancer, treating the sample, if necessary, to liberate nucleic acids contained therein, contacting said nucleic acids with appropriate pairs of any of the PCR primers described herein, carrying out a PCR reaction under conditions suitable to provide an amplicon, and analyzing such amplicon to determine if it contains the novel 5' BRAF splice variant(s) described herein. In one embodiment, such method uses a pair of PCR primers that is effective to provide an amplicon that includes the novel splice junction of the BRAF splice variants described herein.

Yet another aspect of the present invention provides a method for predicting resistance to the therapeutic effects of BRAF and/or pan-RAF inhibitors (e.g. PLX4302) in a subject suffering from or suspected of having cancer. This method utilizes the composition and methods described herein and concludes that upon detection of any of the novel 5' BRAF splice variant(s) described herein, the subject is predicted to be resistant to treatment with such BRAF and/or pan-RAF inhibitors.

Another aspect of the present invention provides a method for treatment of a subject predicted to be resistant to the therapeutic effects of BRAF and/or pan-RAF inhibitors (e.g. PLX4302) by the methods herein whereby such treatment comprises treatment selected from the group consisting of an inhibitor to BRAF dimerization or inhibitor of signaling molecules downstream of BRAF (e.g. MEK). Such treatment may further comprise a BRAF and/or pan-RAF inhibitor.

A further aspect of the present invention provides isolated polynucleotide sequences of the novel 5' BRAF splice variant(s) described herein and proteins translated from such polynucleotide sequences. In one embodiment of the present invention, such isolated polynucleotide sequence(s) (or protein translated therefrom) are chosen from a group comprising a BRAF mRNA with deletion of exons 4-10, BRAF mRNA with deletion of exons 4-8, and BRAF mRNA with deletion of exons 2-8. Such isolated polynucleotide sequences (and proteins translated therefrom) may further comprise N' terminal or C' terminal tags such as FLAG, V5, MYC, HA, fluorescent moiety(ies) (e.g. GFP, YFP, etc.) etc. The isolated polynucleotide sequences can be cloned into an appropriate expression vector and ectopically expressed in a cell for use in the methods of the present invention for identifying an agent useful for treating cells and/or tumors that are resistant to BRAF inhibition and/or identifying an agent useful for the disruption of RAS-independent BRAF dimers. In one embodiment of the present invention, said expression vector is comprised of pcDNA3.1.

A further aspect of the present invention provides a cell that endogenously or ectopically expresses any of the novel 5' BRAF splice variants described herein. In one embodiment, the cell is chosen from the group comprising SKMEL-239 clone C1, SKMEL-239 clone C3, and SKMEL-239 clone C4. These cells have demonstrated resistance to a BRAF inhibitor following extended exposure of the cells to the BRAF inhibitor.

In another aspect, the invention relates to a cell comprising a recombinant nucleic acid that encodes a BRAF splice variant protein. The nucleic acid has a nucleotide sequence that encodes a BRAF splice variant as described herein and, in some embodiments, is placed in an expression vector for transfection into a cell, for example, a cell chosen from the group comprising SKMEL-239, HT-39, and 293H cells. The cell transfected with the BRAF variant is resistant to a BRAF inhibitor. The process for transfecting a cell with an appropriate nucleic acid is well known in the art.

A further aspect of the present invention therefore, provides a method for identifying an agent useful for treating cells and/or tumors that are resistant to BRAF and/or pan-RAF inhibition comprising contacting a cell that endogenously or ectopically expresses any of the novel 5' BRAF splice variant(s) described herein with a potential agent, measuring the amount of cell death and/or cell growth of said cell, and comparing the amount of cell death and/or cell growth in presence of said potential agent to the amount of cell death and/or cell growth in the absence of said potential agent, wherein increased cell death and/or decreased cell growth in the presence of said potential agent indicates that said potential agent is effective to treat cells and/or tumors that are resistant to said BRAF and/or pan-RAF inhibition. Such contacting may further include contacting with said potential agent in combination with a BRAF and/or pan-RAF inhibitor Such measuring may further comprise measuring ERK activation and comparing the amount of ERK activation in presence of said agent to the amount of ERK activation in the absence of said agent, wherein a decrease in ERK activation in the presence of said agent indicates that said potential agent is effective to treat cells and/or tumors that are resistant to said BRAF and/or pan-RAF inhibition.

Assays for measurement of cell death, both apoptosis and necrosis, are well known in the art and include, without limitation, measurement of accumulation of a sub-G1 peak by FACS, caspase activation assays, TUNEL and DNA fragmentation assays, PARP cleavage assays, Annexin V assays, exclusion of trypan blue, etc. Assays for measurement cell growth are well known in the art and include, without limitation, measurement of absolute cell number, cell cycle analysis via FACS, MTT assay, etc. Assays for measurement of ERK activation are well known in the art and include, without limitation, quantification of phospho-ERK levels, luciferase-based reporter assays, and biomarker signatures of activated ERK, etc. All such assays for measurement are envisioned to be within the scope of preferred embodiment(s) of the present invention. In one embodiment of the present invention, a cell used in the above method endogenously expresses BRAF mRNA with deletion of exons 4-8. In another embodiment of the present invention, said cell is chosen from the group comprising SKMEL-239 clone C1, SKMEL-239 clone C3, and SKMEL-239 clone C4 as described herein. In another embodiment of the present invention, a cell used in the above method that ectopically expresses BRAF mRNA is chosen from the group comprising BRAF mRNA with deletion of exons 4-10, BRAF mRNA deletion of exons 4-8, and BRAF mRNA deletion of exons 2-8. In another embodiment of the present invention said cell is chosen from the group comprising SKMEL-239, HT-39, and 293H.

A further aspect of the present invention provides a method for identifying an agent useful for disrupting RAS-independent BRAF dimers comprising contacting isolated polypeptides translated from of the novel 5' BRAF splice variant(s) described herein with a potential agent, measuring the amount of BRAF dimers, and comparing the amount of BRAF dimers in the presence of said potential agent to the amount of BRAF dimers in the absence of said potential agent, wherein a decrease in the amount of BRAF dimers in the presence of said potential agent indicates such potential agent is effective to disrupt RAS-independent BRAF dimers. Such agent effective to disrupt RAS-independent dimers is useful to re-sensitize resistant cells and/or tumors to BRAF and/or pan-RAF inhibition and can be used as combination treatment with BRAF and pan-RAF inhibitors. Assays to measure the amount of a protein dimer are well known in the art and include, without limitation, FRET based methodologies, immunoprecipitation, non-reducing Western blotting, bimolecular fluorescence complementation etc. Methods for these and other assays suitable for evaluation of dimer formation are known to those of skill in the art. All such assays within the scope of preferred embodiment(s) of the present invention.

A further aspect of the present invention provides an additional kit(s) comprising vessel(s) containing varying combinations of a cell line of the present invention, isolated polynucleotide sequences of the novel 5' BRAF splice variant(s) described herein, purified proteins of the 5' BRAF splice variant(s) described herein and a BRAF and/or pan-RAF inhibitor. Such kit further comprises additional reagents useful for practicing the method of the present invention for identifying an agent useful for treating cells and/or tumors that are resistant to BRAF and/or pan-RAF inhibition and/or identifying an agent useful for disrupting RAS-independent BRAF dimers. Such kit(s) can further contain instructions on practicing the methods of the present invention.

EXAMPLES

Example 1

Acquired Resistance: Generation of Cell Populations Resistant to BRAF Inhibition Via Continued Exposure to PLX4032

Figure 1A:
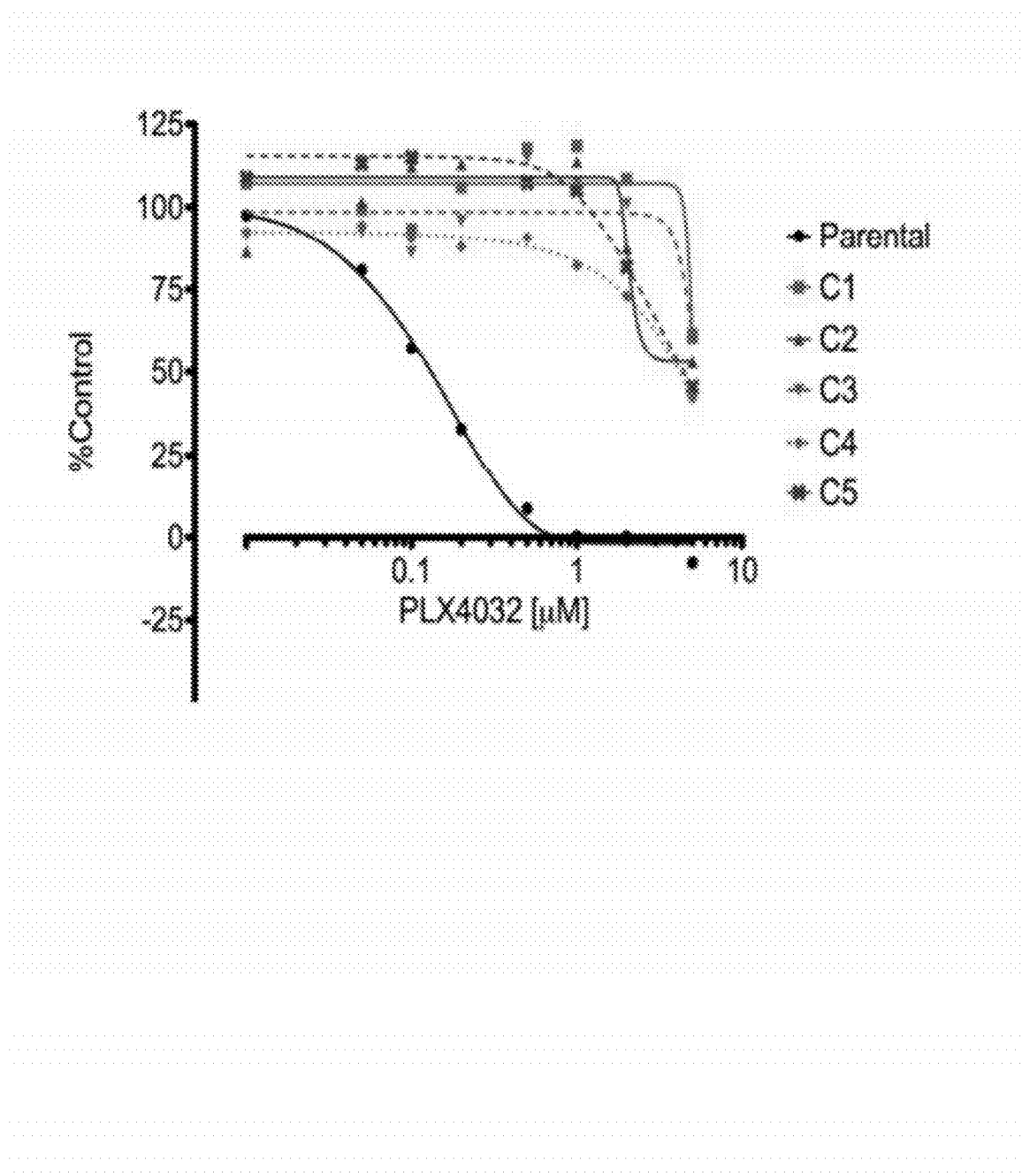
FIGS. 1A-1E show that resistance to the RAF inhibitor PLX4032 is associated with failure of the drug to inhibit ERK signaling.

RAF inhibitors have remarkable clinical activity in mutant BRAF melanomas that is limited by acquisition of resistance to the drug8. In order to identify novel mechanisms of resistance to RAF inhibitors, the inventors of the present invention generated cell lines resistant to PLX4032, a clinically relevant BRAF inhibitor, by exposing the melanoma cell line SKMEL-239 to a set high dose of PLX4032 (2 µM). At this concentration, PLX4032 effectively inhibits ERK signaling in SKMEL-239 which results in accumulation of cells in G1 and a significant induction of cell death (FIG. 1A-C, FIG. 5B and data not shown). Five independent PLX4032-resistant cell populations were generated after approximately 2 months of continuous drug exposure (FIG. 1A). This approach, rather than one of gradual adaptation to increasing concentrations of drug, was chosen since continuous exposure to a high dose of drug more closely represents the clinical situation.

Example 2

Characterization of BRAF Inhibitor Resistant Clones Reveals a Novel Genetic Alteration not Previously Described in Known Mechanisms of Resistance to BRAF Inhibitor(s)

Figure 1B:
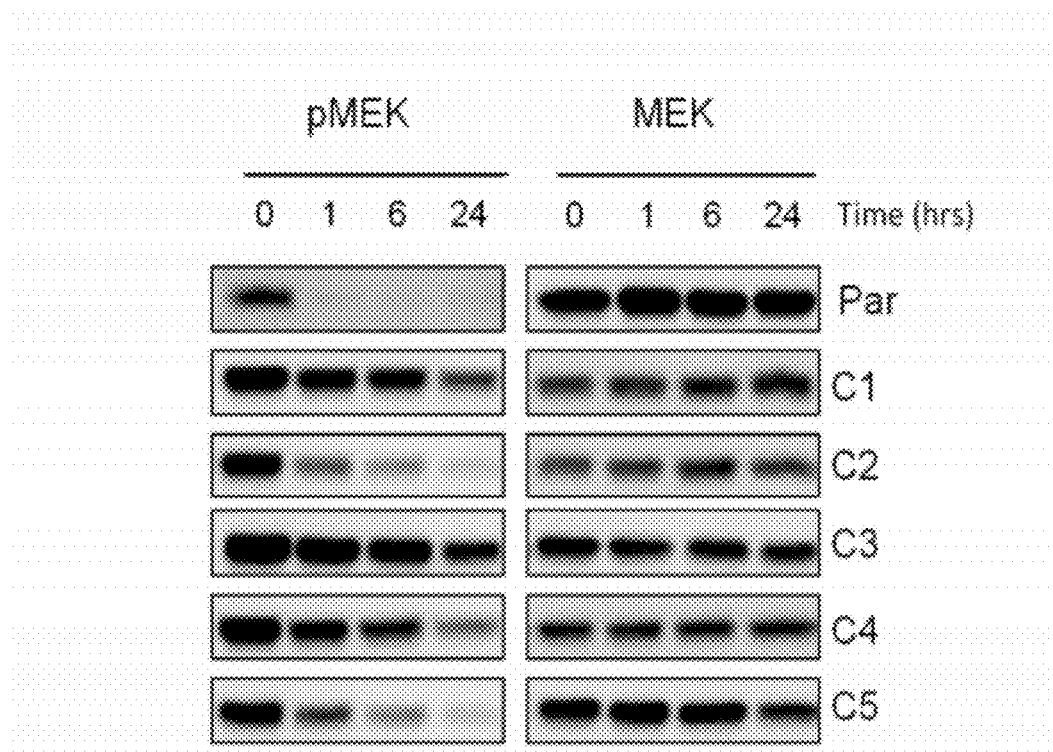
Figure 1C:
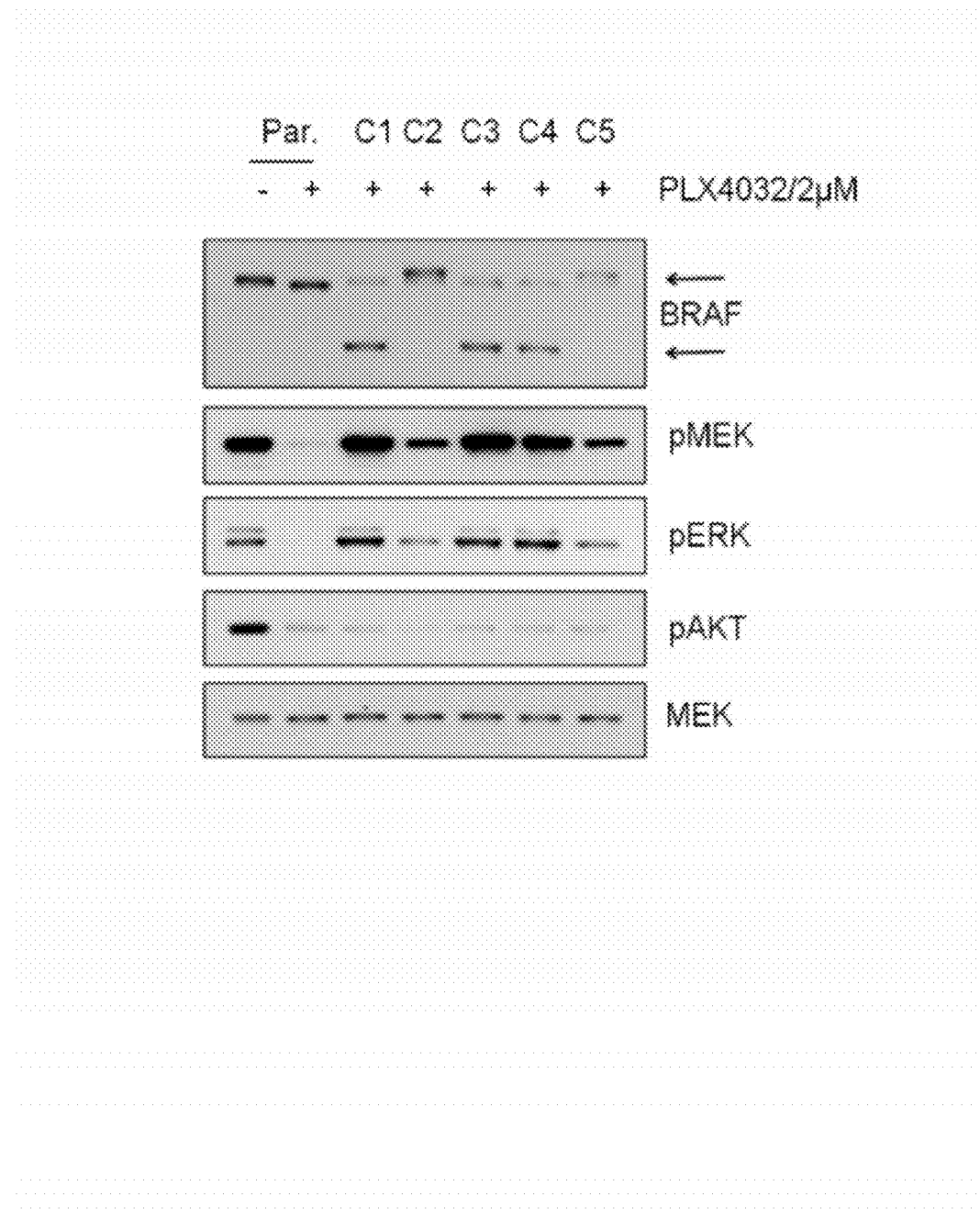
Figure 1D:
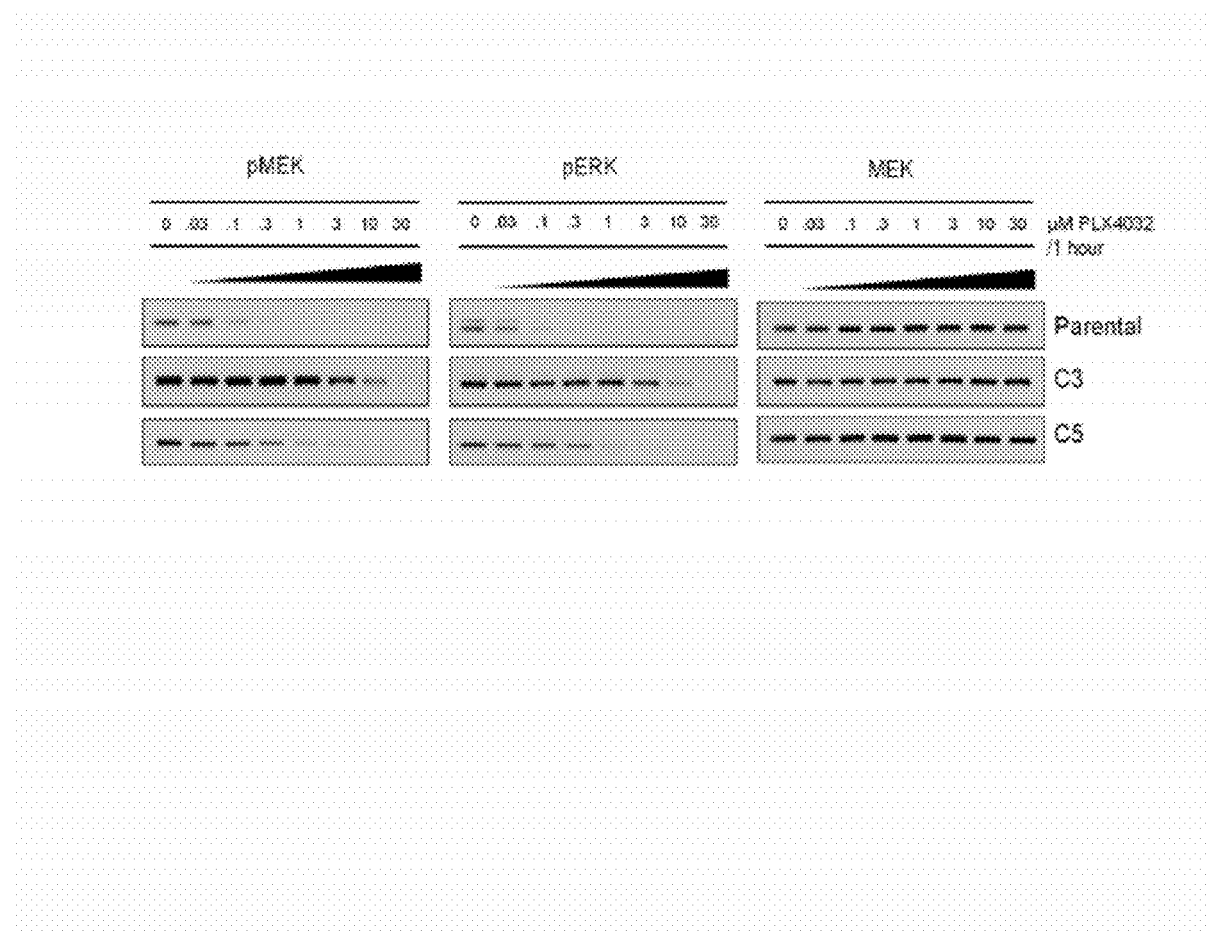
Figure 1E:
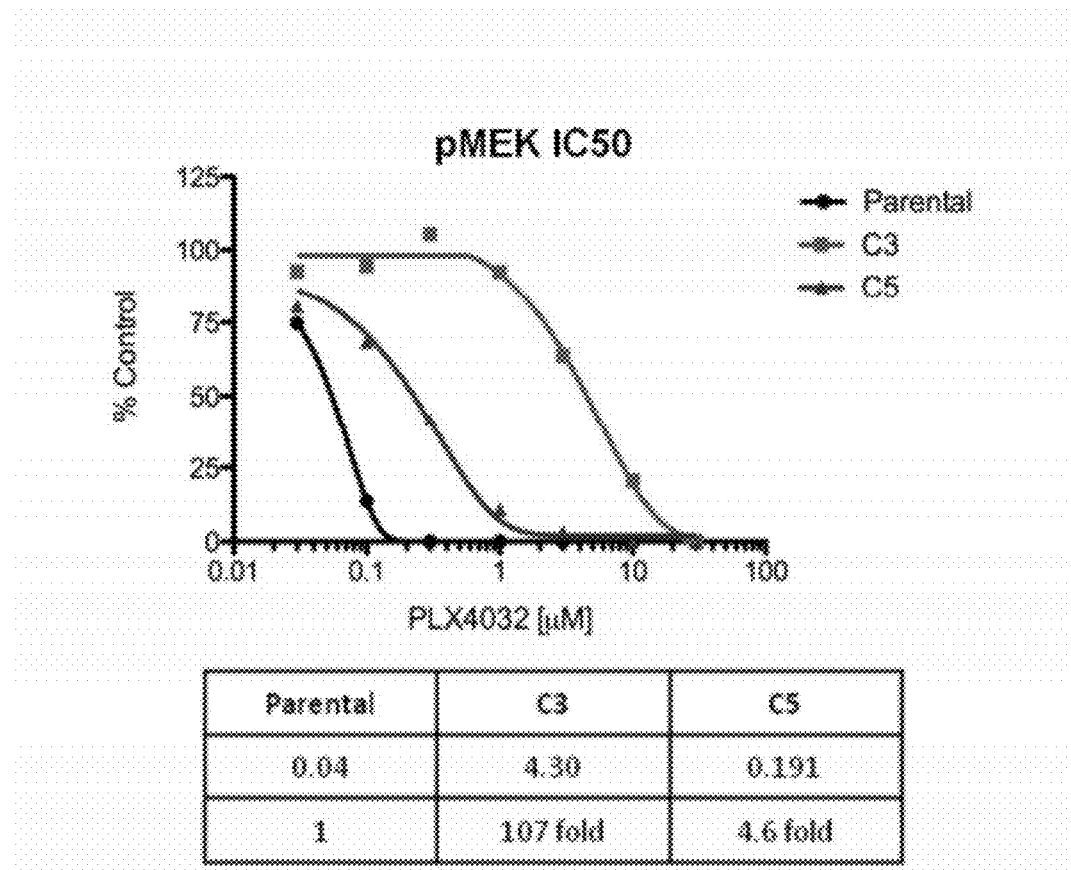

Resistance of SKMEL-239 cells to PLX4032 was associated with decreased sensitivity of ERK signaling to the drug (FIG. 1B-C, FIG. 5A). Analysis revealed the presence of two distinct classes of resistant clones. In the first, exemplified by the C3 clone, the IC50 for pMEK inhibition was more than 100-fold higher than that of the parental cell line (FIG. 1D, E). Despite a similar degree of resistance to the anti-proliferative and pro-apoptotic effects of PLX4032, the second class of clones, exemplified by clone C5, demonstrated only a modest increase in pMEK IC50 (4.5-fold higher than the parental clone). All five resistant clones retained sensitivity to the MEK inhibitor, PD032590113, albeit at slightly higher doses than required to inhibit MEK in the parental cell line (FIG. 6A, B).

Sequence analysis of both DNA and cDNA derived from the five resistant clones showed that all clones retained expression of BRAF(V600E) (FIG. 7). No mutations in BRAF at the gatekeeper site14, RAS mutation(s), or upregulation of receptor tyrosine kinases were detected (FIG. 8 and data not shown), indicating a novel mechanism of resistance to BRAF inhibition. Western blot analysis of BRAF protein expression showed that each of the resistant clones expressed a 90 kd band that co-migrated with the band observed in parental cells. In the C1, C3 and C4 clones, a new more rapidly migrating band was also identified, which ran at an approximate molecular weight of 61 kd, FIG. 1C, FIG. 5A). No band of this size was detected in parental SKMEL-239 cells or in a panel of 14 other melanoma cell lines (FIG. 9) suggesting that its expression is a result of acquired resistance to BRAF inhibition.

PCR analysis of cDNA derived from each resistant cell line using the PCR primers of the present invention [SEQ ID NOS: 2 and 3] revealed the expected single transcript of 2.3 kb, representing full-length BRAF in parental cells and two transcripts of 2.3 kb and 1.7 kb respectively in C3 cells as shown by gel electrophoresis. Sanger sequence analysis of the 1.7 kb PCR product from C3 cells revealed that it was a BRAF transcript that contained the V600E mutation and an in-frame deletion of exons 4-8 (FIG. 2A) (mRNA transcript and resulting translated protein herein referred to individually and collectively as "p61 BRAF(V600E)"). This 1.7 kb transcript is predicted to encode a protein of 554 amino acids and a molecular weight of 61 kd, consistent with the lower band detected by immunoblotting with the anti-BRAF antibody (FIG. 10). Exons 4-8 encodes the majority of CR1 and CR2 of BRAF, which include domains critical for RAF activation, most notably, the RBD and the CRD3. The p61BRAF(V600E) variant identified in C3 was also detected in clones C1 and C4 by real time PCR, with the PCR primers of the present invention that anneal specifically to the 3_9 splice junction [SEQ ID NOS 5-6] (FIG. 10). Inspection of the BRAF locus on chromosome 7q34 by array comparative genomic hybridization data suggested no evidence of an intragenic somatic deletion within the BRAF gene.

Example 3

Figure 2B:
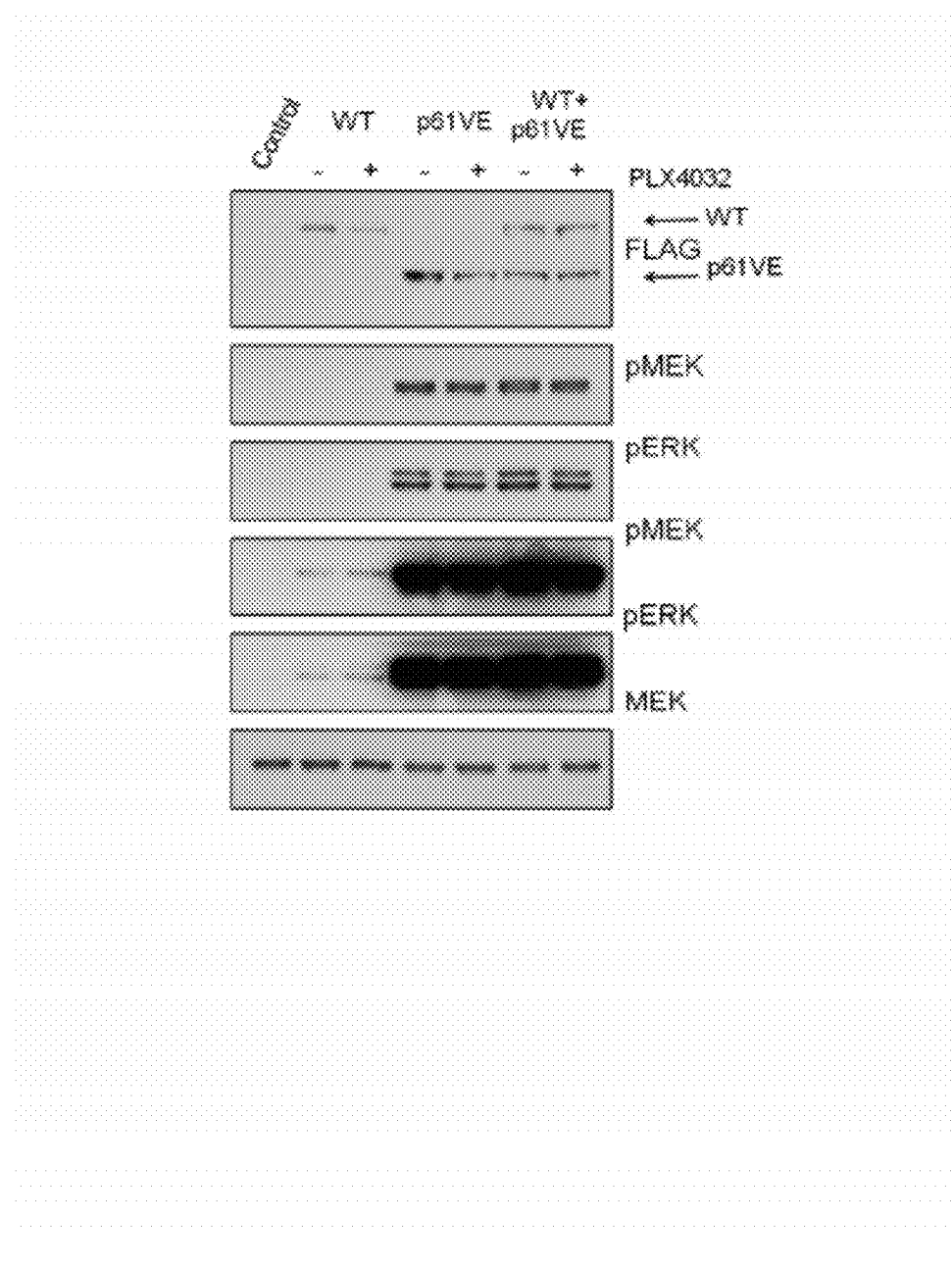

Novel 5' BRAF Splice Variant Lacking Exons 4-8 is Sufficient for Conferring Resistance to BRAF Inhibition The 1.7 kb transcript encoding p61 BRAF(V600E) was cloned into an expression vector and ectopically expressed in 293H cells, alone or together with full-length wild-type BRAF. As shown in FIG. 2B, ERK signaling was resistant to PLX4032 in 293H cells in which p61 BRAF(V600E) was ectopically expressed. Furthermore, expression of p61 BRAF(V600E) in parental SKMEL-239 cells or in the HT-29 colorectal cancer cell line, which endogenously expresses BRAF(V600E), resulted in failure of PLX4032 to effectively inhibit ERK signaling (FIG. 11A, B). PLX4032 has been shown to inhibit the kinase activity of RAF immunoprecipitated from cells, but activates intracellular RAF4. This suggests that the conditions required for transactivation in vivo are not recapitulated in the in vitro assay. The inventors of the present invention tested whether p61 BRAF(V600E) is also sensitive to PLX4032 in vitro. Although the in vitro activity of p61 BRAF(V600E) was slightly higher than full-length BRAF(V600E), similar concentrations of PLX4032 cause inhibition of both p61 BRAF (V600E) and full-length BRAF(V600E) in vitro (FIG. 12). These data suggest that p61 BRAF(V600E) is capable of binding PLX4032 and that resistance of p61 BRAF(V600E) to PLX4032 is not due to its inability to bind the inhibitor.

Example 4

Figure 2C:
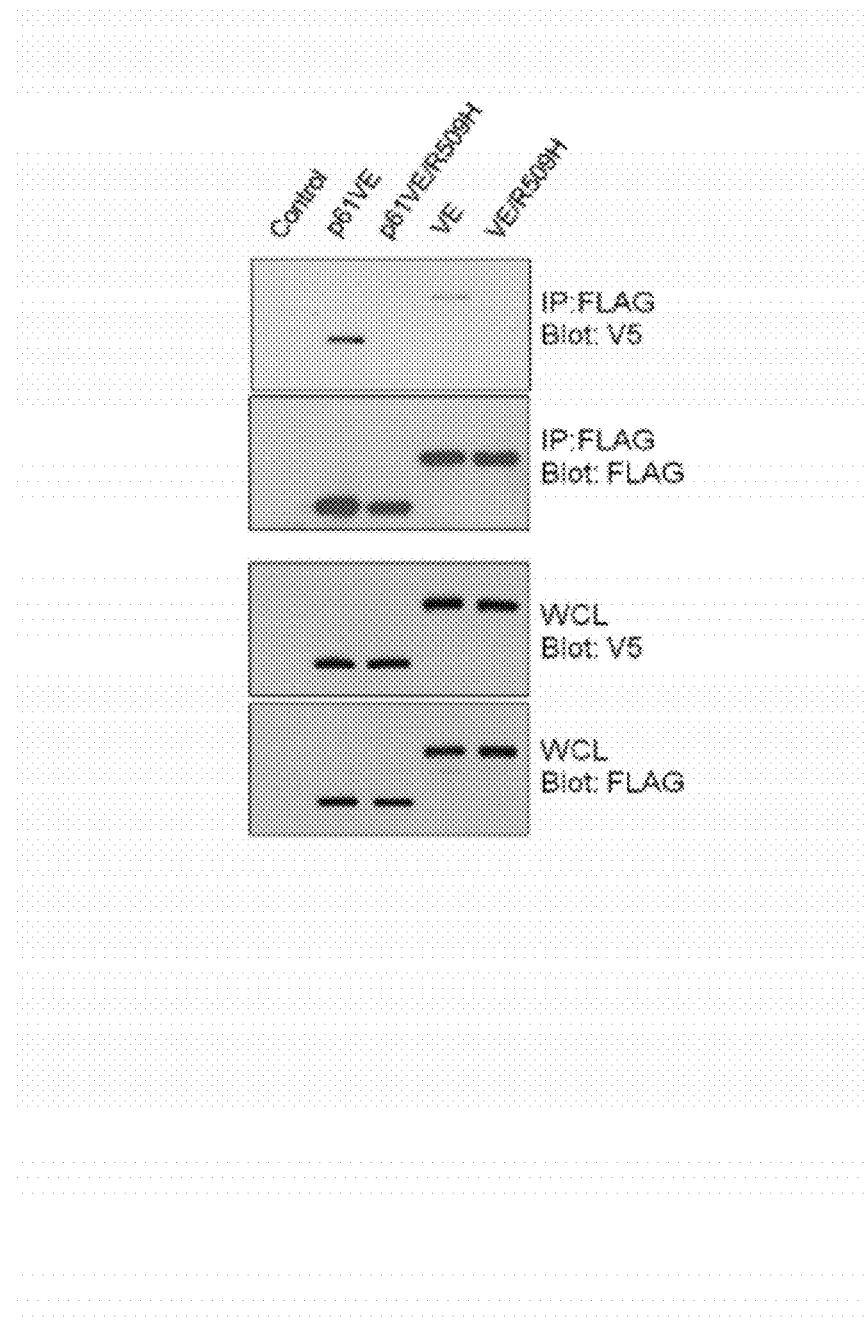
Figure 2D:
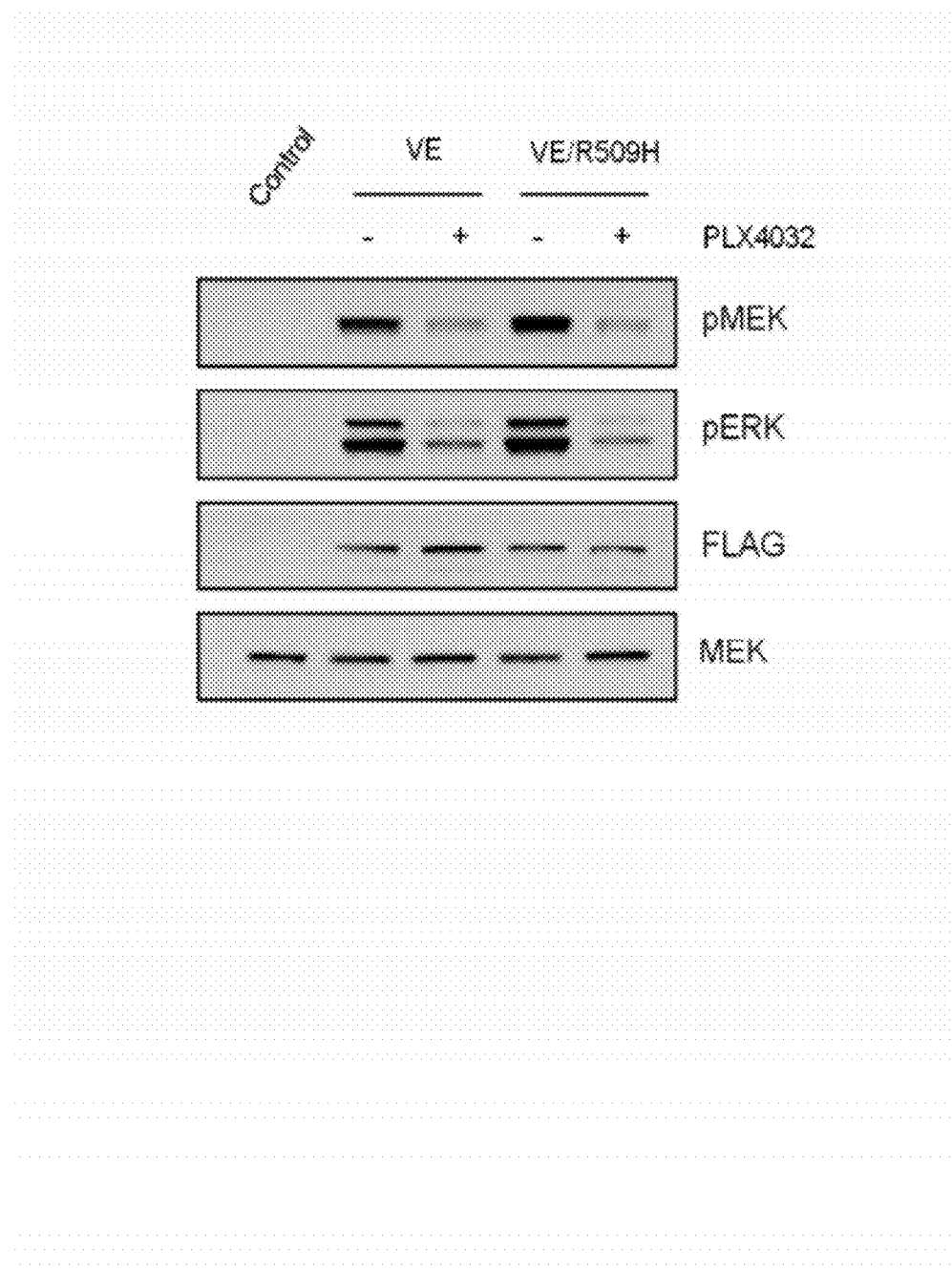

The Novel 5' BRAF Splice Variant(s) Promote Dimerization and Activation of BRAF in the Absence of RAS Signaling The inventors of the present invention then determined whether deletion of exons 4-8 promoted dimerization of p61 BRAF(V600E). To determine levels of dimerization, the inventors ectopically co-expressed two constructs encoding the same protein; either p61 BRAF(V600E) or full-length BRAF(V600E) with different tags (Flag or V5). When ectopically expressed in 293H cells, dimerization of p61 BRAF(V600E) was significantly elevated compared to that of full-length BRAF(V600E) (FIG. 2C). The R509 residue (arginine at amino acid position 509 in BRAF protein) is within the BRAF dimerization interface; mutation of this residue to a histidine abolishes the ability of wild-type BRAF to dimerize and results in loss of its catalytic activity in cells4,16. However, full length BRAF(V600E) with a point mutation converting R509 to H509 (R509H, arginine→histidine at amino acid 509 in BRAF protein (referred to herein as "R509H"), ectopically expressed in 293H cells retained its ability to fully activate ERK signaling and remained sensitive to PLX4032 (FIG. 2D). These data indicate that BRAF(V600E) can signal as a monomer and support the idea that elevated RAS-GTP levels and RAF dimerization are necessary for the activation of wild-type RAF proteins but not that of the BRAF(V600E) mutant.

Figure 2E:
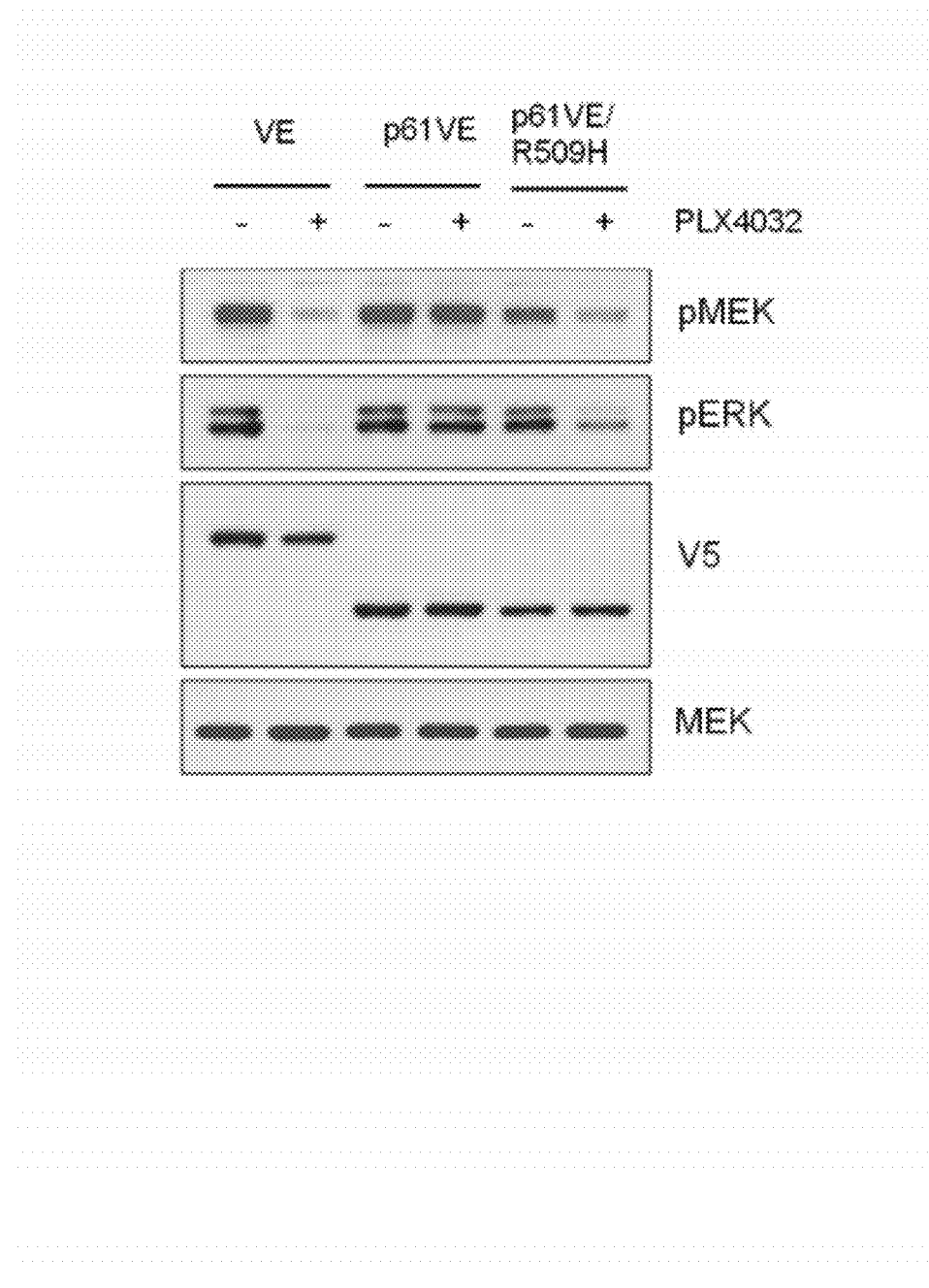
Figure 4:
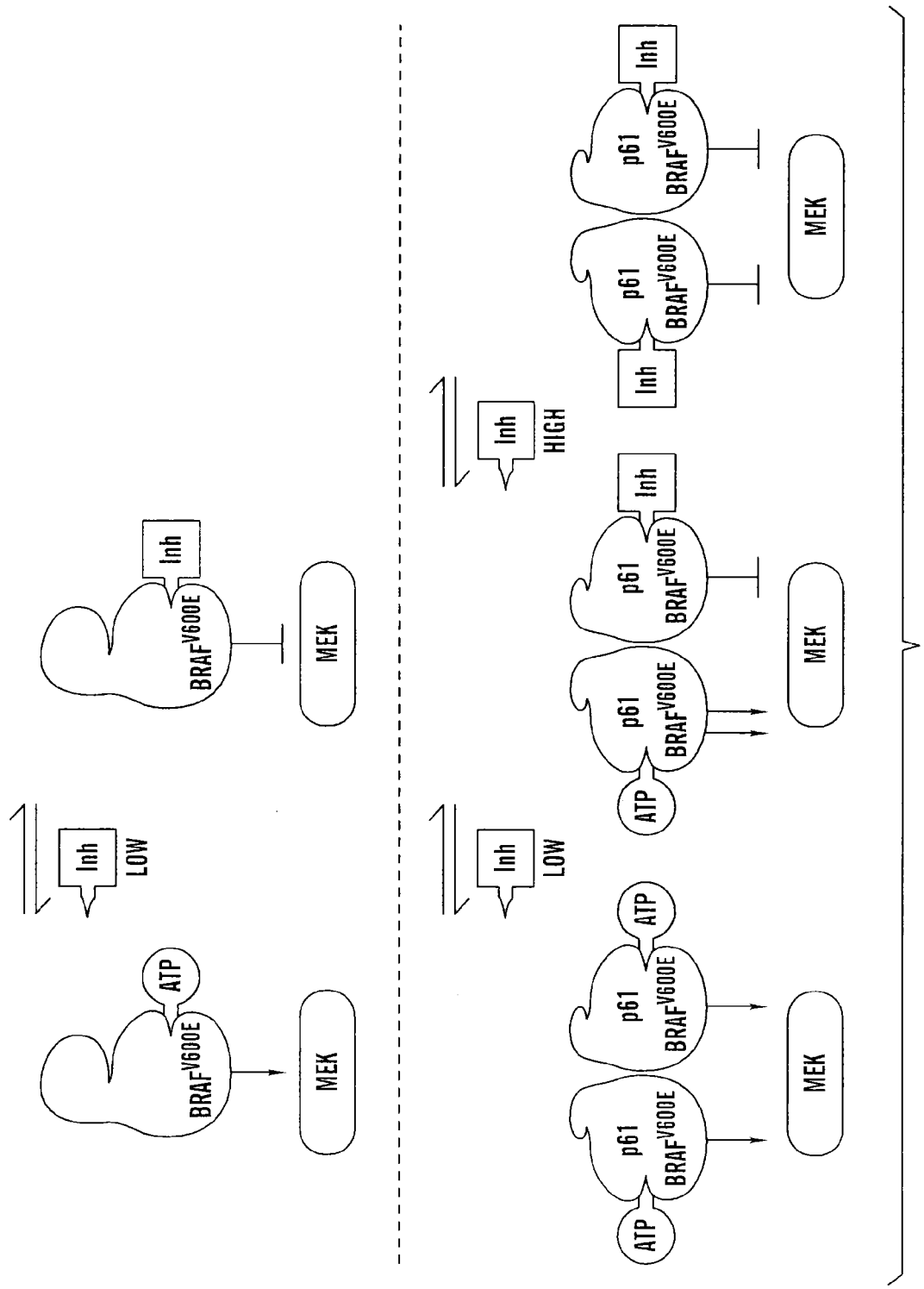
FIG. 4 is a model of p61 BRAF(V600E)-mediated resistance resulting from loss of the RAS-binding domain.

To test directly whether resistance mediated by p61 BRAF(V600E) was the result of elevated dimer formation, the inventors of the present invention introduced the R509H dimerization-deficient mutation into cDNA encoding for p61 BRAF(V600E) (hereinafter referred to as "p61 BRAF (V600E/R509H)"). In 293H cells ectopically expressing p61 BRAF(V600E), phosphorylation of ERK was elevated and was insensitive to PLX4032 (FIG. 2E). ERK activity was also elevated in cells expressing p61 BRAF(V600E/R509H), but to a slightly lesser degree. p61 BRAF(V600E/R509H) does not dimerize in these cells, confirming that the R509H mutation located within the dimerization interface disrupts the formation of p61 RAF(V600E) dimers (FIG. 2C). This monomeric p61 BRAF(V600E/R509H) was sensitive to RAF inhibitors; in cells ectopically expressing the protein, ERK signaling was inhibited by PLX4032 (FIG. 2E). Thus, the R509H mutation both prevents the RAS-independent dimerization of p61 BRAF(V600E) and sensitizes it to the RAF inhibitor. These data confirm that deletion of exons 4-8 from BRAF(V600E) causes it to become insensitive to RAF inhibitors by promoting dimerization in a RAS-independent manner (FIG. 4). These data therefore further suggest that any N' terminal BRAF splice variant that promotes increased RAS-independent BRAF dimerization results in resistance to BRAF inhibition.

Example 5

Analysis of Clinical Samples Confirms that i) the N' Terminal Splice Variant(s) of the Present Invention can be Used to Predict Patient Response to BRAF and/or Pan-RAF Inhibitor(s); and ii) N' Terminal Splice Variants, in Addition to p61BRAF (V600E), are Clinically Relevant To determine whether BRAF splice variants can account for clinical resistance to RAF inhibitors, the inventors of the present invention analyzed tumors from eight melanoma patients with resistance to PLX4032. The inventors performed PCR analysis of cDNA from these tumors using the PCR primers of the present invention [SEQ ID NOS: 2 and 3], and the resulting PCR product were Sanger sequenced. Pre-treatment samples from two patients showed a single band of the expected size (2.3 kb) which, by sequencing, was confirmed to include both BRAF(V600E) and wild-type BRAF transcripts as expected (FIG. 3A and data not shown). In a matching post-treatment sample, the inventors of the present invention identified two PCR amplicons of different sizes as resolved by gel electrophoresis. Sequencing revealed that the larger band encoded both the full-length wild-type BRAF and full-length BRAF(V600E), whereas the smaller band encoded a BRAF(V600E) transcript lacking exons 4-10 with a novel 3_11 splice junction (FIG. 3A-C, Patient I). Similarly, in a another post-treatment sample (patient II) the larger band represented both the full-length wild-type BRAF and full-length BRAF(V600E), whereas the smaller transcript represented a BRAF(V600E) variant lacking exons 4-8 with a novel 3_9 splice junction, a splice variant identical to the variant p61 BRAF(V600E) identified in the C1, C3 and C4 clones (FIG. 3A, C). Finally, in a third post-treatment sample, the inventors identified a transcript encoding a BRAF(V600E) variant that lacked exons 2-8 with a novel 1_9 splice junction (patient III). A single PCR amplicon was identified in three additional post-treatment samples and the two samples derived from patients with intrinsic resistance (patient IV shown) and was shown by sequencing to encode full-length BRAF (FIG. 3A and Table 2).

Example 6

The Presence of the N' Terminal BRAF Splice Variant(s) of the Present Invention Suggest Alternative Treatment Strategies in Subjects Resistant to BRAF Inhibitor(s)

As resistance to PLX4032 resulting from expression of p61 BRAF(V600E) is attributable to attenuation of the ability of the drug to inhibit RAF activation, tumors expressing p61 BRAF(V600E) retain sensitivity to inhibitors of downstream effectors of RAF, such as MEK, which was shown by the inventors of the present invention (FIG. 6). Therefore, MEK inhibitors, when used in combination with BRAF inhibitors such as PLX4032, delay or prevent the onset of this mechanism of resistance. Furthermore, MEK inhibitors can be used as a second-line therapy in subjects that develop resistance to BRAF inhibitors driven by the expression of the novel 5' BRAF splice variants described herein. Additionally, any compound that inhibits the RAS-independent dimerization of the novel 5' BRAF splice variants described herein can be successful alternative treatment strategies in subjects resistant to BRAF inhibitor(s).

Example 7

Novel Model of Resistance Provides Composition and Methods to Predict Patient Response to Treatment with BRAF Inhibitor(s) and Redirection of Treatment Strategy(ies) Following Said Prediction of Response In the tumors from patients that have been analyzed, resistance to PLX4032 is associated with inability of the drug to inhibit ERK signaling. The present invention and the inventors' previous work suggests that this can be due to increased BRAF dimer formation in the cell4. This can happen in at least two ways i) increasing RAS-GTP levels; and/or ii) induction of RAS-independent dimerization. NRAS mutation has now been reported in BRAF inhibitor-resistant tumors9. The present invention discloses novel genetic alteration(s) that causes increased RAS-independent dimerization in patient tumors; namely novel 5' BRAF splice variant(s) lacking exons, or portions thereof, that regulate BRAF dimerization. Other mechanisms of resistance to RAF inhibitors in model systems and in patients have also been reported recently and include activation of the receptor tyrosine kinases PDGFRβ and IGF1R9,11. Another MEK kinase, COT, that can bypass the requirement of BRAF (V600E) for ERK signaling has also been shown to cause resistance to RAF inhibitors as has mutation of MEK1 10,12.

p61BRAF(V600E), and the additional 5' BRAF splice variants described herein, is the first resistance mechanism identified that involves a structural change in BRAF itself. Notably, the 5' BRAF splice variants described herein identified both in the resistant cell lines and patients have all been confined to the mutant BRAF allele (e.g. BRAF (V600E)). This suggests that generation of the 5' BRAF splice variants described herein is likely due to a mutation or epigenetic change that affects BRAF splicing and not to a loss of global splicing fidelity18. In particular, the identification of 5' BRAF splice variants lacking the RAS-binding domain, or portions thereof, in three of six patients with acquired resistance suggests that this mechanism is clinically important. Furthermore, the clarification of such mechanism of resistance permits the predication of patient response to treatment with BRAF inhibitor using the compositions and methods of the present invention and also permits redirection of treatment strategy(ies) following said prediction of response.

Example 8

Chemicals and Plasmids

The BRAF inhibitor, PLX403219 (vemurafenib) was obtained from Plexxikon Inc. PD0325901 was synthesized in the MSKCC Organic Synthesis Core Facility. Flag-tagged BRAF constructs have been described previously4. All other plasmids were created using standard cloning methods, with pcDNA3.1 (Invitrogen) as a vector. Mutations were introduced using the site-directed Mutagenesis Kit (Stratagene). For transfection studies, cells were seeded on 35 mm or 100 mm plates and transfected the following day using Lipofectamine 2000 (Invitrogen). Cells were collected 24 hours later for subsequent analysis. cDNA Preparation and PCR.

The Superscript III First-Strand Synthesis kit (Invitrogen) was used to generate cDNA. Primers designed for the 5'- and 3'- of BRAF mRNA had the following sequences:

```
                              (SEQ ID NO: 2)
F' GGCTCTCGGTTATAAGATGGC
and (SEQ ID NO: 3)
R' ACAGGAAACGCACCATATCC.
```

Sanger sequencing of the products was outsourced to the contract research organization Genewiz. For qPCR analysis, cDNA synthesis was carried out with the High Capacity cDNA Reverse Transcription Kit (Applied Biosystems). qPCR was performed with the iQ SYBR Green RT-PCR Super Mix (BioRad) and the C1000 Thermal Cycler (BioRad). The comparative Ct method was employed to quantify transcripts and delta Ct was measured in triplicate. Primers for the total amount of BRAF:

```
                              (SEQ ID NO: 10)
F' TCAATCATCCACAGAGACCTC
and (SEQ ID NO: 11)
R' GGATCCAGACAACTGTTCAAAC;
```

Primers for the novel splice junctions:
1_9 Splice Junction

```
                              (SEQ ID NO: 4)
F' CTGCCATTCCGGAGGAGGACT
and (SEQ ID NO: 5)
R' TTAGTTAGTGAGCCAGGTAATGA
```

3_9 Splice Junction [SEQ ID NO 6 and 5]:

```
                              (SEQ ID NO: 6)
F' ACAAACAGAGGACAGTGGAC
and (SEQ ID NO: 5)
R' TTAGTTAGTGAGCCAGGTAATGA
```

3_11 Splice Junction [SEQ ID NO 7 and 8]:

```
                              (SEQ ID NO: 7)
F' CAAACAGAGGACAGTGAAA (SEQ ID NO: 8)
R' ACAGGAAACGCACCATATCC
```

Patient Samples.

Melanoma tumor specimens from patients treated with vemurafenib (PLX4032) on an Memorial Sloan-Kettering Cancer Center IRB-approved protocol were flash frozen in liquid nitrogen immediately after resection or biopsy. To determine tumor content, 5 µm sections from frozen patient tumor specimens were cut, stained with hematoxylin and eosin, and scored by a pathologist. If the specimen had >70% tumor content (excluding necrosis), the remainder of the frozen tumor was homogenized using a Bullet Blender (Next Advance, Inc.) with 0.9-2 mm stainless steel beads for 5 min at a speed setting of 10. RNA was then extracted from the tumor homogenate using the RNeasy Mini Kit (Invitrogen) and quantified. Clinical characteristics of the melanoma tumors from patients are shown in Table 2.

Cell Proliferation and Cell Cycle Analysis.

All melanoma cell lines were generated by A. Houghton (MSKCC) or obtained from ATCC. 293H cells were obtained from Invitrogen. Cells were maintained in RPMI (SKMEL-239) or DMEM (293H), supplemented with 2 mM glutamine, antibiotics and 10% fetal bovine serum. The inventors of the present invention confirmed by DNA fingerprinting using methods standard in the art (see ref. 20: PMID 10.1016/j.ccr.2010.11.023 (2010)) that all PLX4032-resistant SKMEL-239 clones were derived from the same patient, thus excluding the possibility of contamination (Table 3).

TABLE 3

| Sample 1 | Sample 2 | p-Value | Bonferroni correction |
|---|---|---|---|
| SKMEL-239 Parental | SKMEL-239 C1 | 8.05037E−15 | 6.85247E−11 |
| SKMEL-239 Parental | SKMEL-239 C2 | 8.05037E−15 | 6.85247E−11 |
| SKMEL-239 Parental | SKMEL-239 C3 | 8.05037E−15 | 6.85247E−11 |
| SKMEL-239 Parental | SKMEL-239 C4 | 8.05037E−15 | 6.85247E−11 |
| SKMEL-239 Parental | SKMEL-239 C5 | 8.05037E−15 | 2.97542E−11 |

For proliferation assays, cells were plated in 6-well plates, and 24 hours later were treated with varying concentrations of inhibitors, or vehicle control, as indicated. IC50 values were calculated using Graph Pad Prism v.5. For cell cycle and apoptosis studies, cells were seeded in 6-well dishes the day prior to drug treatment. For analysis, both adherent and floating cells were harvested and stained with ethidium bromide as described previously 21.

Western blotting and receptor tyrosine kinase (RTK) arrays. Western blot analysis was performed as previously described13. The following antibodies were used: p217/p221-MEK (pMEK), p202/p204-ERK (pERK), MEK, ERK, (Cell Signaling), V5 tag (Invitrogen), BRAF, cyclin Flag tag, β-actin (Sigma). For immunoprecipitations of tagged proteins: anti-Flag M2 affinity gel (Sigma). The Human Phospho-RTK array Kit (R&D Systems) was utilized to detect kinase activation within a panel of RTKs. Briefly, cells were plated in 10 cm dishes and harvested after 24 hours. Following lysis, 500 μg of lysate was applied to a membrane-anchored RTK array and incubated at 4° C. for 24 hours. Membranes were exposed to chemiluminescent reagents and images captured using the ImageQuant LAS 4000 instrument (GE HealthCare).

Immunoprecipitations and kinase assays. Cells were lysed in lysis buffer (50 mM Tris, pH7.5, 1% NP40, 150 mM NaCl, 10% glycerol, 1 mM EDTA) supplemented with protease and phosphatase inhibitor cocktail tablets (Roche). Immunoprecipitations were performed at 4° C. for 4 h, followed by three washes with lysis buffer and, in cases of subsequent kinase assay, one final wash with kinase buffer (25 mM Tris, pH 7.5, 10 mM MgCl2). Kinase assays were conducted in the presence of 200 μM ATP at 30° C. for 20 min with inactive MEK(K97R) (Millipore) as a substrate. The kinase reaction was terminated by adding sample buffer and boiling. Kinase activity was determined by immunoblotting for pMEK.

From the foregoing description, one skilled in the art can easily ascertain the essential characteristics of the present invention, and without departing from the spirit and scope thereof, can make changes and modifications to the present invention to adapt it to various usages and conditions and to utilize the present invention to its fullest extent. The preceding embodiments and examples are to be construed as merely illustrative, and not limiting of the scope of the invention in anyway whatsoever.

REFERENCES 1. 1 Weber, C. K., Slupsky, J. R., Kalmes, H. A. & Rapp, U. R. Active Ras induces heterodimerization of cRaf and BRaf. Cancer Res 61, 3595-3598 (2001).
2. 2 Rushworth, L. K., Hindley, A. D., O'Neill, E. & Kolch, W. Regulation and role of Raf-1/B-Raf heterodimerization. Mol Cell Biol 26, 2262-2272, doi:26/6/2262 [pii]
3. 10.1128/MCB.26.6.2262-2272.2006 (2006).
4. 3 Wellbrock, C., Karasarides, M. & Marais, R. The RAF proteins take centre stage. Nat Rev Mol Cell Biol 5, 875-885, doi:nrm1498 [pii]
5. 10.1038/nrm1498 (2004).
6. 4 Poulikakos, P. I., Zhang, C., Bollag, G., Shokat, K. M. & Rosen, N. RAF inhibitors transactivate RAF dimers and ERK signalling in cells with wild-type BRAF. Nature 464, 427-430, doi:nature08902 [pii]
7. 10.1038/nature08902 (2010).
8. 5 Heidorn, S. J. et al. Kinase-dead BRAF and oncogenic RAS cooperate to drive tumor progression through CRAF. Cell 140, 209-221, doi:S0092-8674(09)01626-2 [pii]
9. 10.1016/j.cell.2009.12.040 (2010).
10. 6 Hatzivassiliou, G. et al. RAF inhibitors prime wild-type RAF to activate the MAPK pathway and enhance growth. Nature 464, 431-435, doi:nature08833 [pii]
11. 10.1038/nature08833 (2010).
12. 7 Joseph, E. W. et al. The RAF inhibitor PLX4032 inhibits ERK signaling and tumor cell proliferation in a V600E BRAF-selective manner. Proc Natl Acad Sci USA 107, 14903-14908, doi:1008990107 [pii]
13. 10.1073/pnas.1008990107 (2010).
14. 8 Flaherty, K. T. et al. Inhibition of mutated, activated BRAF in metastatic melanoma. N Engl J Med 363, 809-819, doi:10.1056/NEJMoa1002011 (2010).
15. 9 Nazarian, R. et al. Melanomas acquire resistance to B-RAF(V600E) inhibition by RTK or N-RAS upregulation. Nature 468, 973-977, doi:nature09626 [pii]
16. 10.1038/nature09626 (2010).
17. 10 Johannessen, C. M. et al. COT drives resistance to RAF inhibition through MAP kinase pathway reactivation. Nature 468, 968-972, doi:nature09627 [pii]
18. 10.1038/nature09627 (2010).
19. 11 Villanueva, J. et al. Acquired resistance to BRAF inhibitors mediated by a RAF kinase switch in melanoma can be overcome by cotargeting MEK and IGF-1R/PI3K. Cancer Cell 18, 683-695, doi:S1535-6108(10)00484-8 [pii]
20. 10.1016/j.ccr.2010.11.023 (2010).
21. 12 Wagle, N. et al. Dissecting Therapeutic Resistance to RAF Inhibition in Melanoma by Tumor Genomic Profiling. J Clin Oncol, doi:JCO.2010.33.2312 [pii]
22. 10.1200/JCO.2010.33.2312 (2011).
23. 13 Solit, D. B. et al. BRAF mutation predicts sensitivity to MEK inhibition. Nature 439, 358-362, doi:nature04304 [pii]
24. 10.1038/nature04304 (2006).
25. 14 Whittaker, S. et al. Gatekeeper mutations mediate resistance to BRAF-targeted therapies. Sci Transl Med 2, 35ra41, doi:2/35/35ra41 [pii]
26. 10.1126/scitranslmed.3000758 (2010).
27. 15 Cutler, R. E., Jr., Stephens, R. M., Saracino, M. R. & Morrison, D. K. Autoregulation of the Raf-1 serine/threonine kinase. Proc Natl Acad Sci USA 95, 9214-9219 (1998).
28. 16 Rajakulendran, T., Sahmi, M., Lefrancois, M., Sicheri, F. & Therrien, M. A dimerization-dependent mechanism drives RAF catalytic activation. Nature 461, 542-545, doi:nature08314 [pii]
29. 10.1038/nature08314 (2009).
30. 17 Poulikakos, P. I. & Rosen, N. Mutant BRAF melanomas—dependence and resistance. Cancer Cell 19, 11-15, doi:S1535-6108(11)00009-2 [pii]
31. 10.1016/j.ccr.2011.01.008 (2011).
32. 18 Luco, R. F., Allo, M., Schor, I. E., Kornblihtt, A. R. & Misteli, T. Epigenetics in alternative pre-mRNA splicing. Cell 144, 16-26, doi:S0092-8674(10)01378-4 [pii]
33. 10.1016/j.cell.2010.11.056 (2011).
34. 19 Bollag, G. et al. Clinical efficacy of a RAF inhibitor needs broad target blockade in BRAF-mutant melanoma. Nature 467, 596-599, doi:nature09454 [pii]
35. 10.1038/nature09454 (2010).

36. 20 Janakiraman, M. et al. Genomic and biological characterization of exon 4 KRAS mutations in human cancer. Cancer Res 70, 5901-5911, doi:0008-5472.CAN-10-0192 [pii]
37. 10.1158/0008-5472.CAN-10-0192 (2010).
38. 21 Nusse, M., Beisker, W., Hoffmann, C. & Tarnok, A. Flow cytometric analysis of G1- and G2/M-phase subpopulations in mammalian cell nuclei using side scatter and DNA content measurements. Cytometry 11, 813-821, doi:10.1002/cyto.990110707 (1990).

We claim:

1. A method for determining resistance of a cell or tissue to a BRAF inhibitor, said method comprising:
   (a) contacting a sample containing a gene product isolated from said cell or tissue with a detectable primer set that binds to a splice variant of BRAF(V600E), said primer set comprising:
      (i) a first primer capable of hybridizing under stringent conditions to an exon 1-9 splice junction of a cDNA encoding a BRAF (V600E) variant; and a second primer that hybridizes to a nucleic acid comprising a nucleotide sequence from exons 11-18 of BRAF (V600E);
      (ii) a third primer capable of hybridizing under stringent conditions to an exon 3-9 splice junction of a cDNA encoding a BRAF (V600E) variant; and a fourth primer that hybridizes to a nucleic acid comprising a nucleotide sequence from exons 11-18 of BRAF(V600E);
      (iii) a fifth primer capable of hybridizing under stringent conditions to an exon 3-11 splice junction of a cDNA encoding a BRAF(V600E) variant and a sixth primer that hybridizes to a nucleic acid comprising a nucleotide sequence from exons 11-18 of BRAF (V600E); or
      (iv) any combination of (i), (ii), and (iii); and
   (b) measuring the amount of detectable primer to determine the presence in said sample of a BRAF(V600E) splice variant, wherein the presence of said splice variant indicates that the cell or tissue is resistant to the BRAF inhibitor.

2. The method of claim 1, wherein said cell or tissue is a melanoma cell or tissue.

3. The method of claim 1, wherein the BRAF inhibitor is vemurafenib.

4. The method of claim 2, wherein the melanoma cell or tissue was previously exposed to the BRAF inhibitor.

5. The method of claim 1, wherein said primer/probe hybridizes under stringent conditions to a nucleic acid comprising nucleotides 549 to 568 of SEQ ID NO: 13 plus 0 to 12 contiguous nucleotides of SEQ ID NO: 13 flanking the 5' or 3' ends thereof.

6. The method of claim 1, wherein said primer/probe hybridizes under stringent conditions to a nucleic acid comprising nucleotides 183 to 203 of SEQ ID NO: 14 with 0 to 12 contiguous nucleotides of SEQ ID NO: 14 flanking the 5' or 3' ends thereof.

7. The method of claim 1, wherein said primer/probe hybridizes under stringent conditions to a nucleic acid comprising nucleotides 610 to 628 of SEQ ID NO: 15 with 0 to 12 contiguous nucleotides of SEQ ID NO: 15 flanking the 5' or 3' ends thereof.

* * * * *